US011376228B2

(12) United States Patent
Zhu et al.

(10) Patent No.: US 11,376,228 B2
(45) Date of Patent: Jul. 5, 2022

(54) POLYSUBSTITUTED BENZENE, PREPARATION METHOD THEREOF, AND METHOD OF USING THE SAME

(71) Applicants: Genifarm Laboratories Inc, Guangzhou (CN); South China University of Technology, Guangzhou (CN)

(72) Inventors: Shifa Zhu, Guangzhou (CN); Tongxiang Cao, Guangzhou (CN); Yongdong Wang, Guangzhou (CN); Zhipeng Huang, Guangzhou (CN)

(73) Assignees: GENIFARM LABORATORIES INC, Guangzhou (CN); SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 0 days.

(21) Appl. No.: 16/986,303

(22) Filed: Aug. 6, 2020

(65) Prior Publication Data

US 2020/0361893 A1 Nov. 19, 2020

Related U.S. Application Data

(63) Continuation-in-part of application No. PCT/CN2018/125074, filed on Dec. 28, 2018.

(30) Foreign Application Priority Data

Feb. 12, 2018 (CN) .......................... 201810148042.8

(51) Int. Cl.
| | | |
|---|---|---|
| *A61K 31/05* | (2006.01) | |
| *C07C 47/57* | (2006.01) | |
| *C07C 45/60* | (2006.01) | |
| *C07D 307/42* | (2006.01) | |
| *C07D 309/26* | (2006.01) | |
| *C07D 333/78* | (2006.01) | |
| *C07J 1/00* | (2006.01) | |
| *C07J 5/00* | (2006.01) | |
| *A61P 35/00* | (2006.01) | |
| *A61K 31/34* | (2006.01) | |
| *A61K 31/381* | (2006.01) | |

(52) U.S. Cl.
CPC .............. *A61K 31/05* (2013.01); *A61K 31/34* (2013.01); *A61K 31/381* (2013.01); *A61P 35/00* (2018.01); *C07C 45/60* (2013.01); *C07C 47/57* (2013.01); *C07D 307/42* (2013.01); *C07D 309/26* (2013.01); *C07D 333/78* (2013.01); *C07J 1/0059* (2013.01); *C07J 5/0053* (2013.01)

(58) Field of Classification Search
CPC ..... A61P 35/00; C07D 307/42; C07D 309/26; C07D 307/78; C07C 307/42; C07C 309/26; A61K 31/05; A61K 31/34; A61K 31/381
See application file for complete search history.

(56) References Cited

U.S. PATENT DOCUMENTS

| 4,500,543 A | 2/1985 | Debernardis et al. |
| 5,385,936 A | 1/1995 | Flack et al. |

FOREIGN PATENT DOCUMENTS

| CN | 101928270 A | 12/2010 |
| CN | 102939286 A | 2/2013 |

OTHER PUBLICATIONS

Cascade Claisen Rearrangement: Rapid Synthesis of Polysubstituted Salicylaldehydes and Total Syntheses of Hemigossypol and Gossypol Tongxiang Cao Yi Kong Kui Luo Dr. Lianfen Chen Prof. Shifa Zhu First published: Apr. 26, 2018.*
Web printout of https://pubchem.ncbi.nlm.nih.gov/compound/4-Allylpyrocatechol, accessed Dec. 18, 2021, pp. 1-26. (Year: 2021).*
Hurd et al, Contribution from the Chemical Laboratory of Northwestern University, published Apr. 7, 1930, vol. 52, pp. 1700-1706. (Year: 1930).*
W. R. Allison et al., Phthalans. Part II. Ultraviolet and infrared spectra, Journal of the Chemical Society, Dec. 1958, pp. 4311-4314, Chemical Society, United Kingdom.
Chandrasekaran Praveen, et al., Regioselective synthesis of phthalans via Cu(OTf)2-catalyzed 5-exo-dig intramolecular hydroalkoxylation of 2-(ethynyl)benzyl alcohols, Tetrahedron Letters, Jul. 2020, pp. 4767-4771, vol. 51, No. 36, Elsevier Science, Netherlands.
Tongxiang Cao, et al., Mechanism-Guided Scaffold Diversification: Perturbing and Trapping the Intermediates of Maltol-Type Cascade Claisen Rearrangement, Organic Letters, Dec. 2018, pp. 90-94, vol. 21, No. 1, American Chemical Society, United States.

(Continued)

*Primary Examiner* — Craig D Ricci
*Assistant Examiner* — Janet L Coppins
(74) *Attorney, Agent, or Firm* — Matthias Scholl P.C.; Matthias Scholl

(57) ABSTRACT

A polysubstituted benzene compound, preparation method thereof, and method of using the same. The compound has a formula I or I', where X represents carbon, sulfur, or oxygen; $R^1$ represents a $C_{1-16}$ alkyl, $C_{2-16}$ alkenyl, or $C_{2-10}$ alkynyl; $R^2$ represents hydrogen, halogen, $C_{1-16}$ alkyl, $C_{2-16}$ alkenyl, or $C_{2-10}$ alkynyl; or an aryl group or a substituted aryl group by 1-5 groups selected from halogen, $C_{1-26}$ alkyl, $C_{1-3}$ halogenated alkyl, O—$C_{1-3}$ alkyl, hydroxyl, amino, nitro, cyano group, aldehyde group and ester group; or a heteroaryl group or a substituted heteroaryl group by 1-5 groups selected from halogen, $C_{1-26}$ alkyl, $C_{1-3}$ halogenated alkyl, O—$C_{1-3}$ alkyl, hydroxyl, amino, nitro, cyano group, aldehyde group and ester group; the heteroaryl group is a 3-10-membered heteroaryl group including N, S, O, or a combination thereof.

7 Claims, No Drawings

(56) References Cited

OTHER PUBLICATIONS

Tongxiang Cao, et al., Cascade Claisen Rearrangement: Rapid Synthesis of Polysubstituted Salicylaldehydes and Total Syntheses of Hemigossypol and Gossypol, Angewandte Chemie International Edition, Jul. 2018, pp. 8702-8707, vol. 57, No. 28, Wiley-VCH, Germany.

Agostino Casapullo, et al., Paniceins and Related Sesquiterpenoids from the Mediterranean Sponge Reniera fulva, Journal of Natural Products, Apr. 1993, pp. 527-533, vol. 56, No. 4, American Chemical Society, United States.

\* cited by examiner

POLYSUBSTITUTED BENZENE, PREPARATION METHOD THEREOF, AND METHOD OF USING THE SAME

CROSS-REFERENCE TO RELATED APPLICATIONS

This application is a continuation-in-part of International Patent Application No. PCT/CN2018/125074 with an international filing date of Dec. 28, 2018, designating the United States, now pending, and further claims foreign priority benefits to Chinese Patent Application No. 201810148042.8 filed Feb. 12, 2018. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

The disclosure relates to a polysubstituted benzene, preparation method thereof, and method of using the same.

The benzene ring is one of the most important structural units in organic chemistry, of which six hydrogen atoms can be replaced by different elements or groups, thus producing benzene derivatives which can be used in the fields of medicine, pesticide, plastics and organic electronic devices, etc.

The polysubstituted benzene is synthesized by substitution reactions, including electrophilic substitution (such as Friedel-Crafts alkylation and Friedel-Crafts acylation), nucleophilic substitution and coupling reactions. These reactions involve harsh reaction conditions, expensive reagents, toxic metal catalysts, and low regioselectivity.

SUMMARY

The disclosure provides a polysubstituted benzene compound, having a formula I or I':

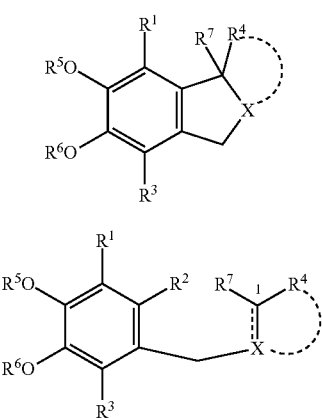

In formula I, $R^4$, $R^7$, X, the carbon atoms connected thereto, and the benzene ring form a fused benzo compound.

In formula I', $R^4$, $R^7$, X, the carbon atoms connected thereto, and the benzene ring form a benzyl compound, benzyl ether compound or benzyl sulfide compound.

The formula I comprises a dotted line referring to $R^4$ connected to X through a group comprising carbon, or no bond and atom connected between $R^4$ and X.

The formula I' comprises a first dotted line referring to a single bond or a double bond between $C^1$ and X, and a second dotted line referring to $R^4$ connected to X through a group comprising carbon, or no bond and atom connected between $R^4$ and X.

Specifically, the fused benzo compound has one of the following two formulas:

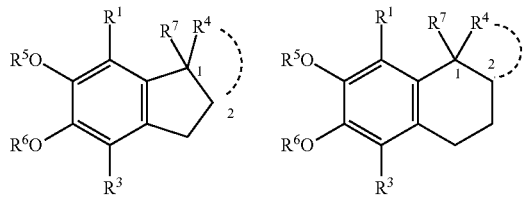

The dotted line in the two formulas means $R^4$ is connected to $C^2$ through a group comprising carbon, or no bond and atom connected between $R^4$ and $C^2$.

The benzyl compound has the following formula:

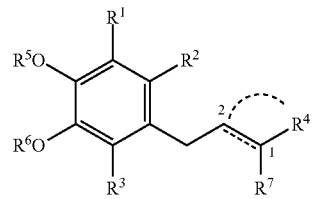

The dotted line between $C^1$ and $C^2$ refers to a single bond or a double bond between $C^1$ and $C^2$; the dotted line between $R^4$ and $C^2$ means $R^4$ is connected to $C^2$ through a group comprising carbon, or no bond and atom connected between $R^4$ and $C^2$.

The benzyl ether compound has the following formula:

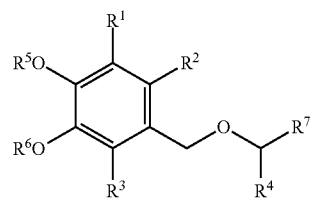

The benzyl sulfide compound has the following formula:

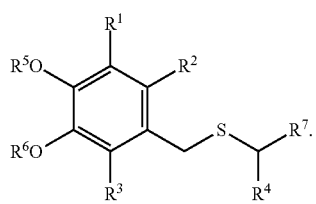

In the formulas, X represents carbon, sulfur, or oxygen;

$R^1$ represents a $C_{1-16}$ alkyl, $C_{2-16}$ alkenyl, or $C_{2-10}$ alkynyl;

$R^2$ represents hydrogen, halogen, $C_{1-16}$ alkyl, $C_{2-16}$ alkenyl, or $C_{2-10}$ alkynyl; or an aryl group or a substituted aryl group by 1-5 groups selected from halogen, $C_{1-26}$ alkyl, $C_{1-3}$ halogenated alkyl, O—$C_{1-3}$ alkyl, hydroxyl, amino, nitro, cyano group, aldehyde group and ester group; or a heteroaryl group or a substituted heteroaryl group by 1-5 groups selected from halogen, $C_{1-26}$ alkyl, $C_{1-3}$ halogenated alkyl, O—$C_{1-3}$ alkyl, hydroxyl, amino, nitro, cyano group, aldehyde group and ester group;

the heteroaryl group is a 3-10-membered heteroaryl group comprising N, S, O, or a combination thereof;

$R^3$ represents $C_{1-6}$ aldehyde group, $C_{2-6}$ acyl group, —COOH, hydroxyl-substituted $C_{1-6}$ alkyl, —$CH_2$O—$C_{1-6}$ alkyl or —$CO_2$—$C_{1-6}$ alkyl;

$R^4$ and $R^7$, at each occurrence, represent hydrogen, a $C_{1-20}$ alkyl, $C_{2-36}$ alkenyl, or $C_{2-10}$ alkynyl; or an aryl group or a substituted aryl group by 1-5 groups selected from halogen, $C_{1-3}$ halogenated alkyl, O—$C_{1-3}$ alkyl, $C_{1-25}$ alkyl, hydroxyl, amino, nitro, cyano group, aldehyde group and ester group;

$R^5$ and $R^6$, at each occurrence, represent hydrogen, $C_{1-6}$ alkyl or $C_{1-6}$ silicon.

Particularly, X represents carbon, sulfur, or oxygen;

$R^1$ represents a $C_{1-4}$ alkyl, $C_{2-4}$ alkenyl, or $C_{3-7}$ alkynyl;

$R^2$ represents hydrogen, halogen, $C_{1-4}$ alkyl, $C_{2-4}$ alkenyl, or $C_{3-7}$ alkynyl; or an aryl group or a substituted aryl group by 1-5 groups selected from halogen, $C_{1-26}$ alkyl, $C_{1-3}$ halogenated alkyl, O—$C_{1-3}$ alkyl, hydroxyl, nitro, cyano group, aldehyde group and ester group; or a heteroaryl group or a substituted heteroaryl group by 1-5 groups selected from halogen, $C_{1-6}$ alkyl, $C_{1-3}$ halogenated alkyl, O—$C_{1-3}$ alkyl, hydroxyl, nitro, cyano group, aldehyde group and ester group;

$R^3$ represents $C_{1-6}$ aldehyde group, $C_{2-6}$ acyl group, —COOH, hydroxyl-substituted $C_{1-4}$ alkyl, —$CH_2$O—$C_{1-4}$ alkyl or —$CO_2$—$C_{1-6}$ alkyl;

$R^4$ and $R^7$, at each occurrence, represent hydrogen, $C_{1-20}$ alkyl, $C_{2-36}$ alkenyl, or $C_{2-10}$ alkynyl; or an aryl group or a substituted aryl group by 1-5 groups selected from halogen, $C_{1-3}$ halogenated alkyl, O—$C_{1-3}$ alkyl, $C_{1-25}$ alkyl, hydroxyl, amino, nitro, cyano group, aldehyde group and ester group; and $R^5$ and $R^6$, at each occurrence, represent hydrogen or $C_{1-4}$ alkyl.

Particularly, X represents carbon, sulfur, or oxygen;

$R^1$ represents a $C_{1-3}$ alkyl, allyl, or $C_{3-4}$ alkynyl;

$R^2$ represents hydrogen, halogen, $C_{1-4}$ alkyl, allyl, or $C_{3-7}$ alkynyl; or an aryl group or a substituted aryl group by 1-5 groups selected from halogen, methyl, methoxyl, $C_{2-26}$ alkyl, hydroxyl, nitro, cyano group, aldehyde group and ester group; or a heteroaryl group or a substituted heteroaryl group by 1-5 groups selected from halogen, $C_{1-6}$ alkyl, $C_{1-3}$ halogenated alkyl, O—$C_{1-3}$ alkyl, hydroxyl, nitro, cyano group, aldehyde group and ester group;

the heteroaryl group is a 5-6-membered heteroaryl group comprising N, S, O, or a combination thereof;

$R^3$ represents a $C_{1-3}$ aldehyde group, $C_{2-4}$ acyl group, —COOH, hydroxyl-substituted $C_{1-4}$ alkyl, —$CH_2$O—$C_{1-4}$ alkyl or —$CO_2$—$C_{1-4}$ alkyl;

$R^4$ and $R^7$, at each occurrence, represent hydrogen, a $C_{1-17}$ alkyl, $C_{2-36}$ alkenyl, or $C_{2-10}$ alkynyl; or an aryl group or a substituted aryl group by 1-5 groups selected from halogen, methoxyl, $C_{1-25}$ alkyl, hydroxyl, nitro, cyano group, aldehyde group and ester group; and $R^5$ and $R^6$, at each occurrence, represent hydrogen or methyl.

Particularly, X represents carbon, sulfur, or oxygen;

$R^1$ represents a $C_{1-3}$ alkyl, allyl, or $C_{3-4}$ alkynyl;

$R^2$ represents hydrogen, halogen, $C_{1-4}$ alkyl, allyl, or $C_{3-7}$ alkynyl; or an aryl group or a substituted aryl group by 1-5 groups selected from halogen, methyl, methoxyl, $C_{2-26}$ alkyl, hydroxyl, nitro, cyano group, aldehyde group and ester group;

$R^3$ represents $C_{1-3}$ aldehyde group, acetyl group, —COOH, hydroxyl-substituted $C_{1-4}$ alkyl, —$CH_2$O—$C_{1-4}$ alkyl or —$CO_2$—$C_{1-4}$ alkyl;

$R^4$ and $R^7$, at each occurrence, represent hydrogen, $C_{1-17}$ alkyl, $C_{2-36}$ alkenyl, or $C_{2-10}$ alkynyl; or an aryl group or a substituted aryl group by 1-5 groups selected from halogen, methoxyl, $C_{1-25}$ alkyl, hydroxyl, nitro, cyano group, aldehyde group and ester group; and $R^5$ and $R^6$, at each occurrence, represent hydrogen or methyl.

Particularly, X represents carbon, sulfur, or oxygen;

$R^1$ represents a $C_{1-3}$ alkyl, allyl, or $C_{3-4}$ alkynyl;

$R^2$ represents hydrogen, halogen, $C_{1-4}$ alkyl, allyl, or $C_{3-7}$ alkynyl; or an aryl group or a substituted aryl group by 1-5 groups selected from halogen, methyl, methoxyl, $C_{2-26}$ alkyl, hydroxyl, nitro, cyano group, aldehyde group and ester group; or a heteroaryl group or a substituted heteroaryl group by 1-5 groups selected from halogen, $C_{1-6}$ alkyl, $C_{1-3}$ halogenated alkyl, O—$C_{1-3}$ alkyl, hydroxyl, nitro, cyano group, aldehyde group and ester group;

the heteroaryl group is a 5-6-membered heteroaryl group comprising N, S, O, or a combination thereof;

$R^3$ represents formyl, acetyl, —COOH, hydroxyl-substituted $C_{1-2}$ alkyl, —$CH_2$O—$C_1$-2 alkyl or —$CO_2$—$C_{1-4}$ alkyl;

$R^4$ and $R^7$, at each occurrence, represent hydrogen, $C_{1-17}$ alkyl, $C_{2-36}$ alkenyl, or $C_{2-10}$ alkynyl; or an aryl group or a substituted aryl group by 1-5 groups selected from halogen, methoxyl, $C_{1-25}$ alkyl, hydroxyl, nitro, cyano group, aldehyde group and an ester group; and $R^5$ and $R^6$, at each occurrence, represent hydrogen or methyl.

Particularly, the polysubstituted benzene is one of the following compounds:
I-1
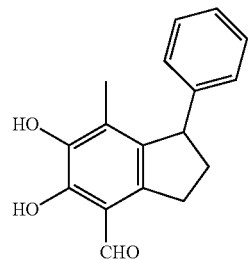
I-2
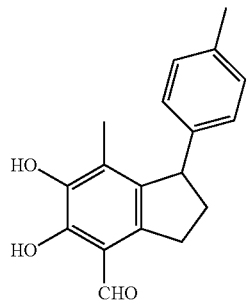
I-3
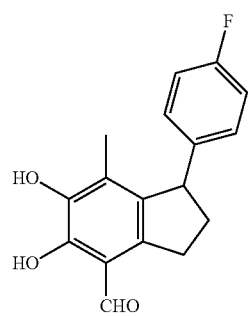
I-4
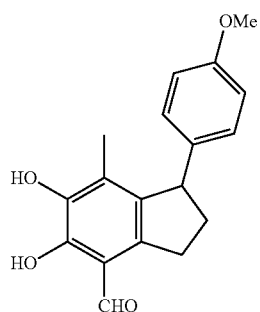
I-5
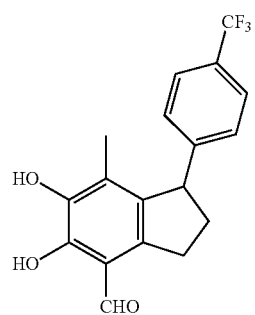
I-6
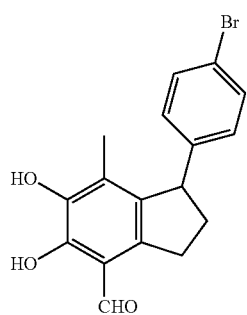
I-7
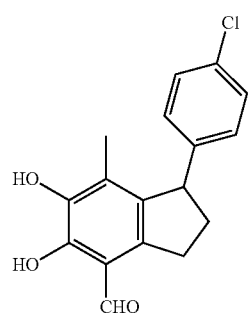
I-8
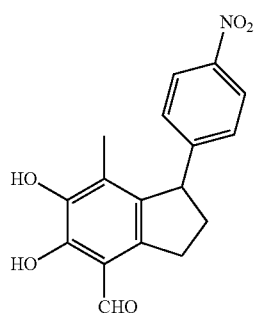
I-9
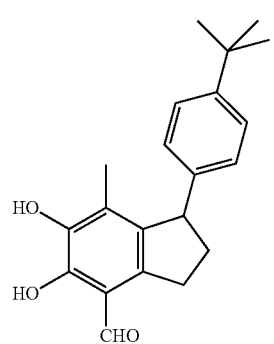
I-10
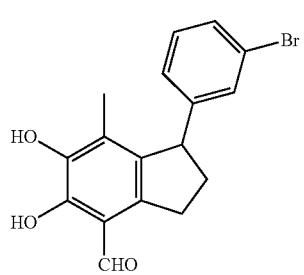

-continued
I-11
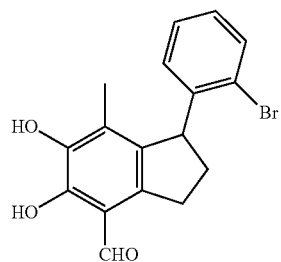
I-12
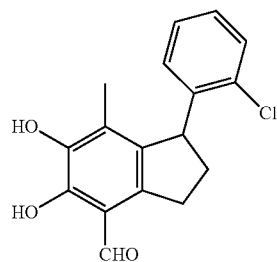
I-13
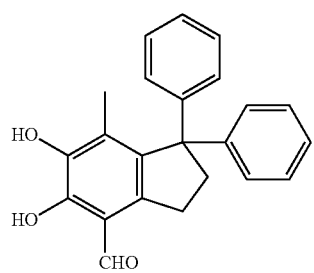 [SMILES: Cc1c(O)c(O)c(C=O)c2c1C(c1ccccc1)(c1ccccc1)CC2]
I-14
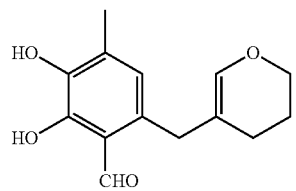 [SMILES: Cc1cc(CC2=COCCC2)c(C=O)c(O)c1O]
I-15
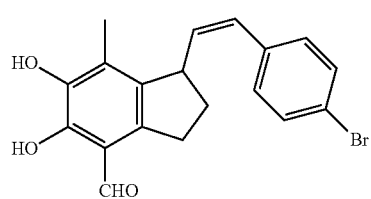
I-16
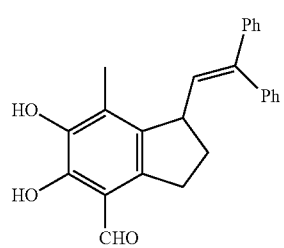
I-17
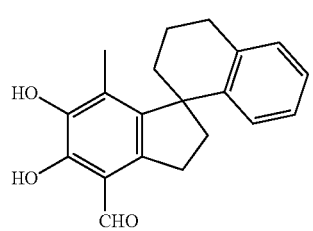
I-18
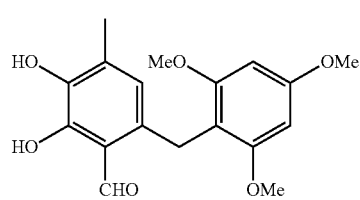 [SMILES: COc1cc(OC)c(Cc2cc(C)c(O)c(O)c2C=O)c(OC)c1]
I-19
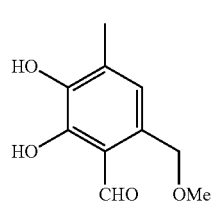
I-20
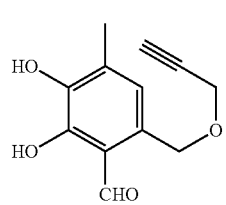 [SMILES: C#CCOCc1cc(C)c(O)c(O)c1C=O]
I-21
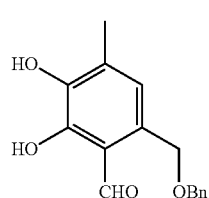 [SMILES: Cc1cc(COCc2ccccc2)c(C=O)c(O)c1O]
I-22
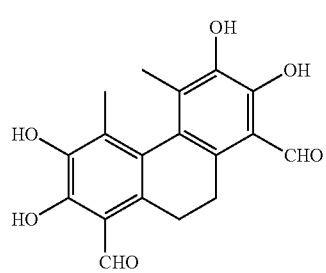 [SMILES: Cc1c(O)c(O)c(C=O)c2c1-c1c(C)c(O)c(O)c(C=O)c1CC2]

-continued
| | |
|---|---|
| 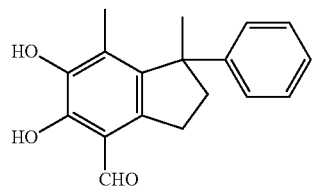 [SMILES: Cc1c(O)c(O)c(C=O)c2c1C(C)(c1ccccc1)CC2] I-23 | 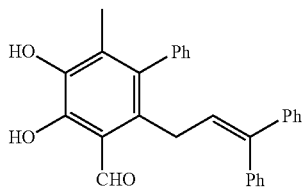 [SMILES: Cc1c(O)c(O)c(C=O)c(CC=C(c2ccccc2)c2ccccc2)c1-c1ccccc1] I-24 |
| 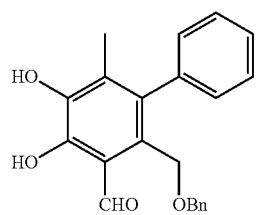 [SMILES: Cc1c(O)c(O)c(C=O)c(COCc2ccccc2)c1-c1ccccc1] I-25 | 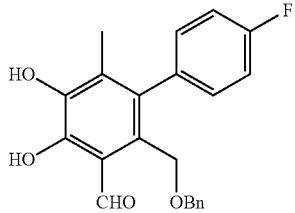 [SMILES: Cc1c(O)c(O)c(C=O)c(COCc2ccccc2)c1-c1ccc(F)cc1] I-26 |
| 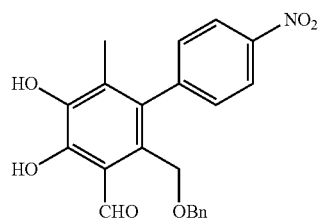 [SMILES: Cc1c(O)c(O)c(C=O)c(COCc2ccccc2)c1-c1ccc([N+](=O)[O-])cc1] I-27 | 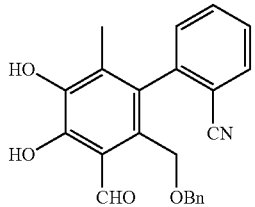 [SMILES: Cc1c(O)c(O)c(C=O)c(COCc2ccccc2)c1-c1ccccc1C#N] I-28 |
| 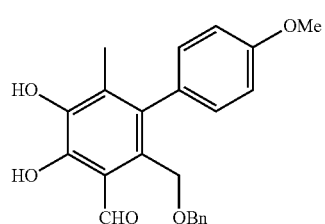 [SMILES: COc1ccc(-c2c(C)c(O)c(O)c(C=O)c2COCc2ccccc2)cc1] I-29 | 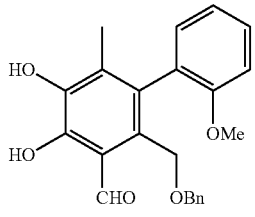 [SMILES: COc1ccccc1-c1c(C)c(O)c(O)c(C=O)c1COCc1ccccc1] I-30 |
| 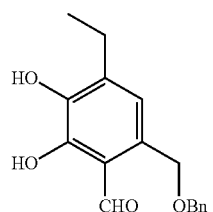 [SMILES: CCc1cc(COCc2ccccc2)c(C=O)c(O)c1O] I-31 | 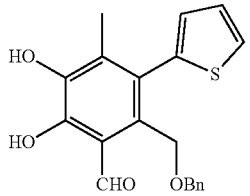 I-32 |
| 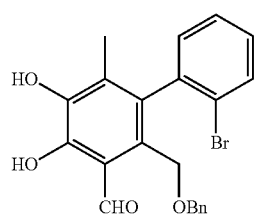 [SMILES: Cc1c(O)c(O)c(C=O)c(COCc2ccccc2)c1-c1ccccc1Br] I-33 | 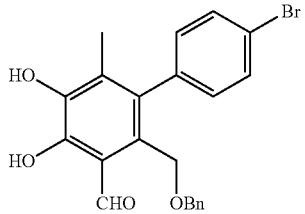 [SMILES: Cc1c(O)c(O)c(C=O)c(COCc2ccccc2)c1-c1ccc(Br)cc1] I-34 |
| 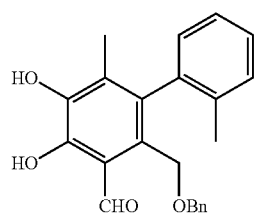 [SMILES: Cc1ccccc1-c1c(C)c(O)c(O)c(C=O)c1COCc1ccccc1] I-35 | 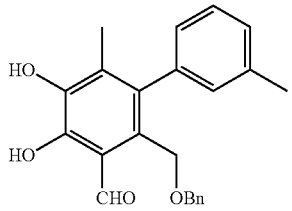 [SMILES: Cc1cccc(-c2c(C)c(O)c(O)c(C=O)c2COCc2ccccc2)c1] I-36 |

-continued
I-37
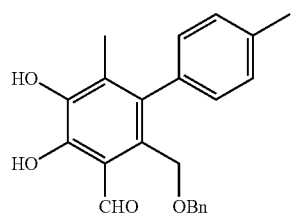 [SMILES: Cc1ccc(-c2c(C)c(O)c(O)c(C=O)c2COCc2ccccc2)cc1]
I-38
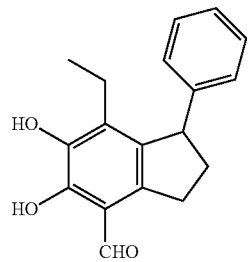
I-39
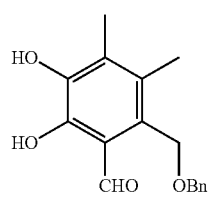 [SMILES: Cc1c(C)c(COCc2ccccc2)c(C=O)c(O)c1O]
I-40
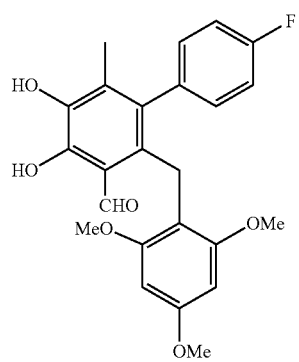
I-41
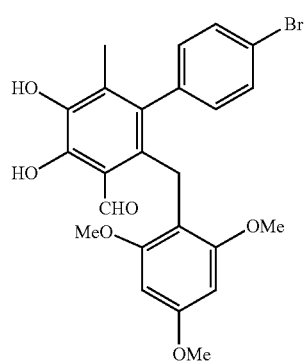
I-42
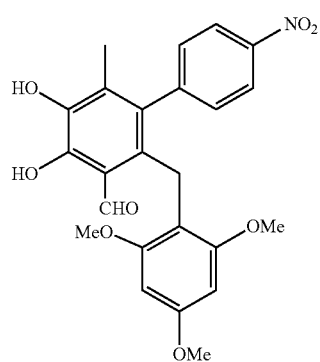
I-43
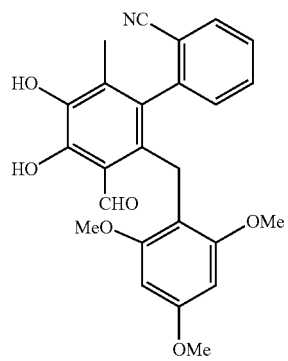
I-44
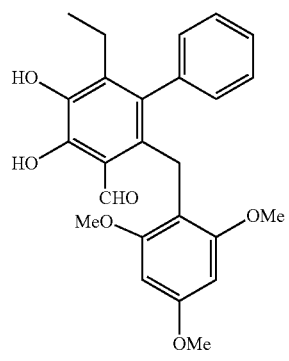
I-45
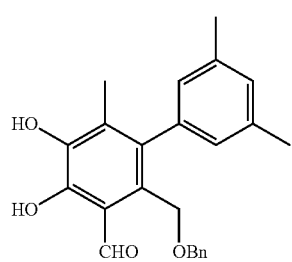 [SMILES: Cc1cc(C)cc(-c2c(C)c(O)c(O)c(C=O)c2COCc2ccccc2)c1]
I-46
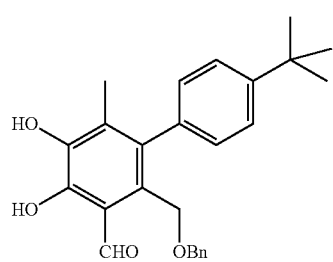

-continued
I-47
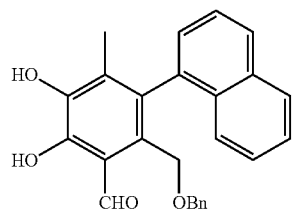 [SMILES: Cc1c(O)c(O)c(C=O)c(COCc2ccccc2)c1-c1cccc2ccccc12]
I-48
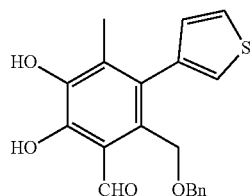
I-49
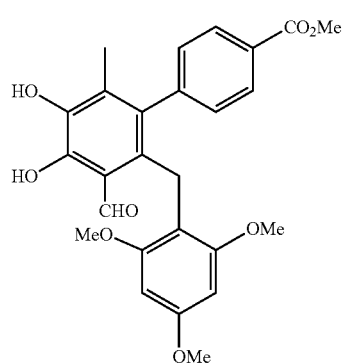
I-50
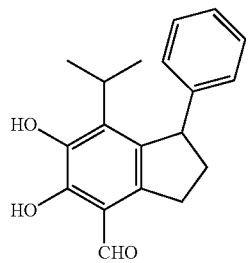
I-51
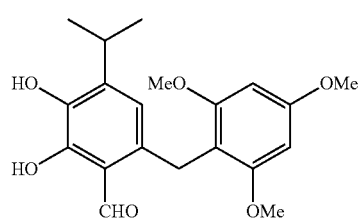 [SMILES: COc1cc(OC)c(Cc2cc(C(C)C)c(O)c(O)c2C=O)c(OC)c1]
I-52
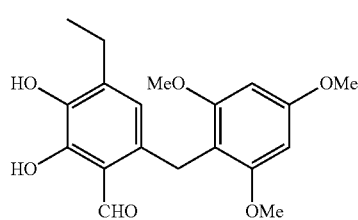 [SMILES: CCc1cc(Cc2c(OC)cc(OC)cc2OC)c(C=O)c(O)c1O]
I-53
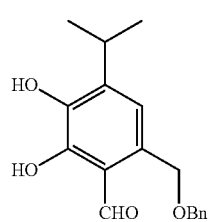
I-54
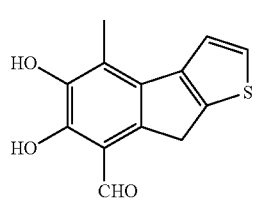 [SMILES: Cc1c(O)c(O)c(C=O)c2c1-c1ccsc1C2]
I-55
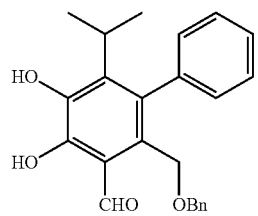 [SMILES: CC(C)c1c(O)c(O)c(C=O)c(COCc2ccccc2)c1-c1ccccc1]
I-A1
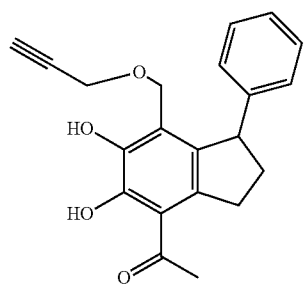
I-A2
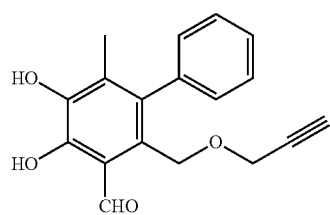 [SMILES: C#CCOCc1c(C=O)c(O)c(O)c(C)c1-c1ccccc1]
I-A3
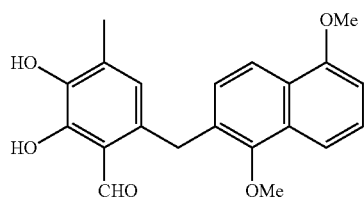 [SMILES: COc1cccc2c(OC)c(Cc3cc(C)c(O)c(O)c3C=O)ccc12]

-continued
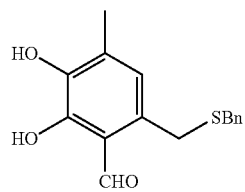
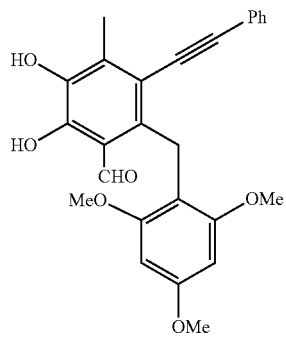
I-A4
I-A5
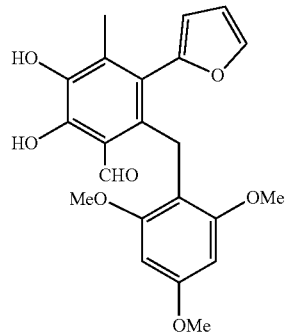
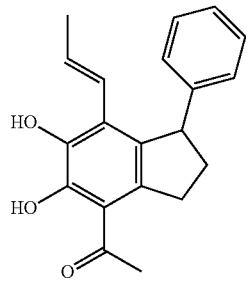
I-A6
I-A7
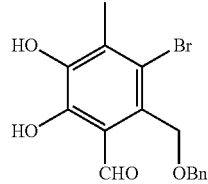
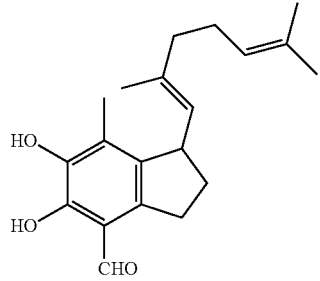
I-A8
I-65
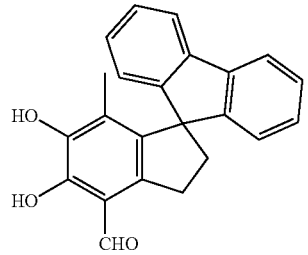
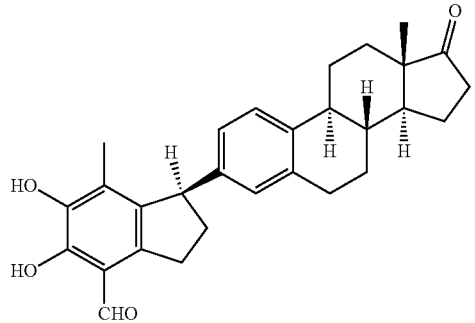
I-66
I-67
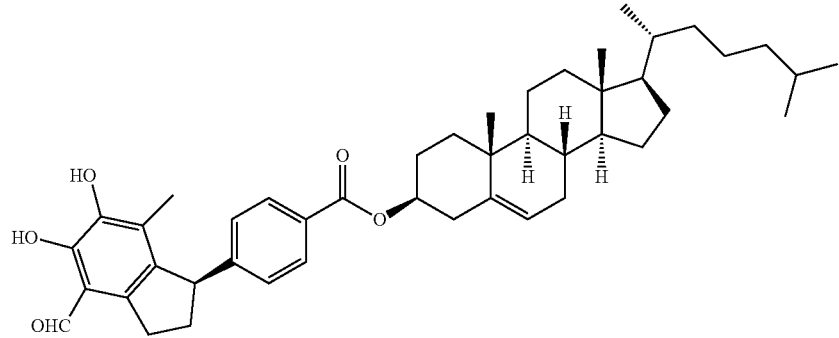
I-68

-continued
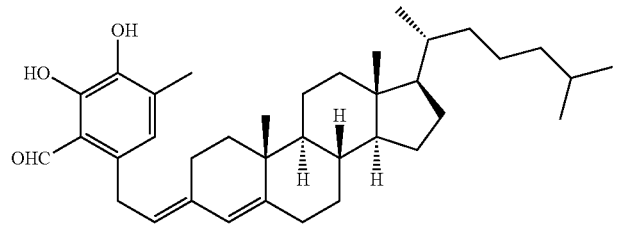
I-69
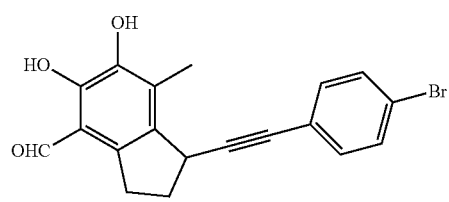
I-70
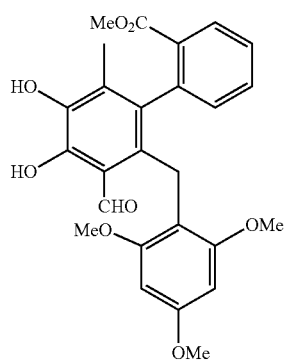
I-71
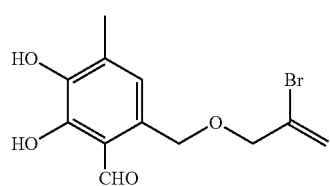
I-72
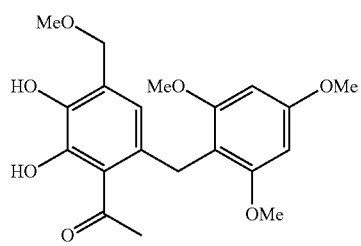
I-73
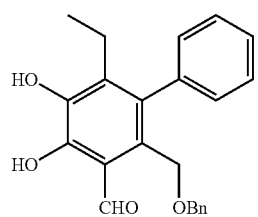
I-74
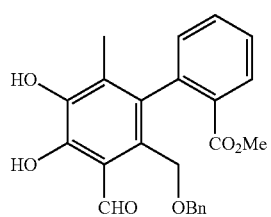
I-75
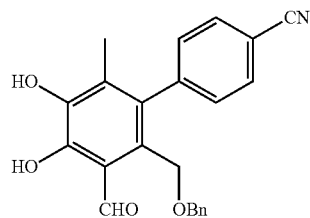
I-76
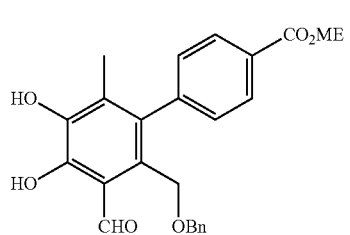
I-77
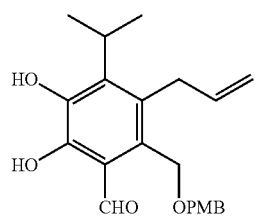
I-78
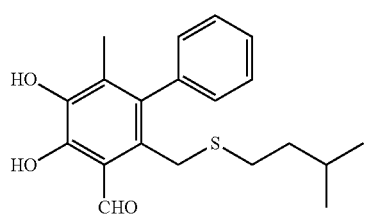
I-79

-continued

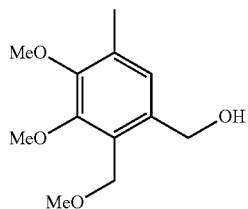
I-94

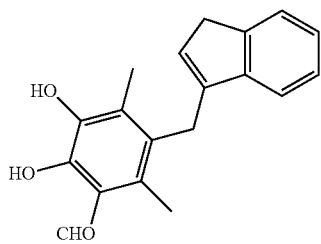
I-95

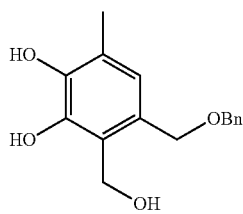
I-96

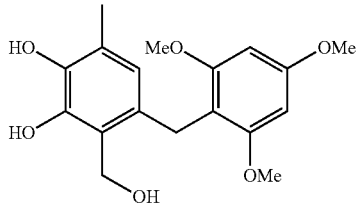
I-97

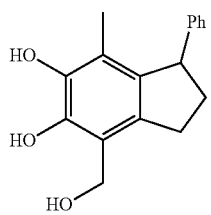
I-98

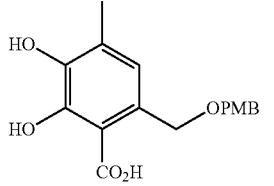
I-99

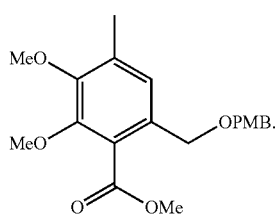
I-100

Hereinafter are the definitions of related groups of the abovementioned formulas:

Alkyl: a linear, branched or cyclic alkyl having 1-26 carbon atoms, comprising methyl, ethyl, propyl, isopropyl, butyl, isobutyl, tertiary butyl, sec-butyl, amyl, new amyl, hexyl, heptyl, octyl, cyclopropyl or cyclohexyl, particularly a linear or branched alkyl having 1-4 carbon atoms, particularly, methyl, ethyl, or isopropyl.

Halogen: fluorine, chlorine, bromine or iodine.

Halogenated alkyl refers to an alkyl substituted by one or more halogens, for example, monohalogenated alkyl, polyhalogenated alkyl, and fully halogenated alkyl; the monohalogenated alkyl refers to an alkyl having only one halogen atom; the polyhalogenated alkyl refers to an alkyl having two or more halogen atoms, including and not limited to fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

$C_{2-16}$ alkenyl: linear or branched alkyl group having 2-16 carbon atoms and comprising at least one carbon-carbon double bond, including and but not limited to vinyl, allyl, butenyl, and hexenyl group.

$C_{2-10}$ alkynyl: linear or branched alkyl group having 2-10 carbon atoms and comprising at least one carbon-carbon triple bond, including and but not limited to ethynyl, propargyl, butynyl and pentynyl.

$C_{1-6}$ aldehyde group: linear or branched alkyl group having 1-6 carbon atoms and comprising at least one formyl group, including but not limited to formaldehyde group, acetaldehyde group and hexaldehyde group.

Aryl group: single or bicyclic aromatic hydrocarbons with 6-14 carbon atoms in the ring part, or aromatic ring comprising non-aromatic hydrocarbon, including but not limited to phenyl, indanyl, naphthyl and 1,2,3,4-tetrahydronaphthalyl.

Heteroaryl group: 3-10-membered heteroaryl group comprising N, S, O, or a combination thereof, including saturated, partially saturated, or unsaturated aromatic groups, monocyclic ring, fused-ring, and bridged-ring, and including but not limited to furan, pyrrole, pyrrolidine, pyrazole, imidazole, triazole, isotriazole, tetrazole, thiadiazole, isothiazole, oxadiazole, pyridine, piperidine, pyrazine, oxazole, pyrazine, pyridazine, pyrimidine, piperazine, pyrrolidine, pyrrolidone, morpholine, triazine, oxazine, tetrahydrofuran, tetrahydrothiophene, tetrahydrothiapyran, tetrahydropyran, 1,4-dioxane, 1,4-oxothiocyclohexane, indazole, quinoline, indole, 8-aza-bicyclo (3.2.1) octane, 2,3-dihydrobenzofuran and 2,3-dihydrobenzothiazole.

Alkoxy: linear or branched chains having 1-6 carbon atoms, including but not limited to methoxy, ethoxy, propoxy, isopropoxy, butoxy, isobutyoxy, tert-butoxy, sec-butoxy, pentyloxy, neopentyloxy or hexyloxy, particularly linear or branched alkoxy having 1-4 carbon atoms, and more particularly, methoxy.

The bioactive polysubstituted benzene comprises one or more amino and carboxyl groups, or the like, so an acid and/or alkali salt thereof is formed, for example, a pharmaceutical salt having the biological effectiveness and properties of the bioactive polysubstituted benzene compound.

Also provided is a method for preparing the bioactive polysubstituted benzene compound. The preparation process is as follows:

Specifically, the method comprises:

1) adding 1 equivalent of compound VII, 1-5 equivalents of a base, and 1-3 equivalents of a compound VI to an organic solvent, thereby yielding a first mixture; heating and stirring the first mixture; filtering the first mixture and evaporating the organic solvent to yield a first product, separating and purifying the first product, thereby yielding a first intermediate product V;

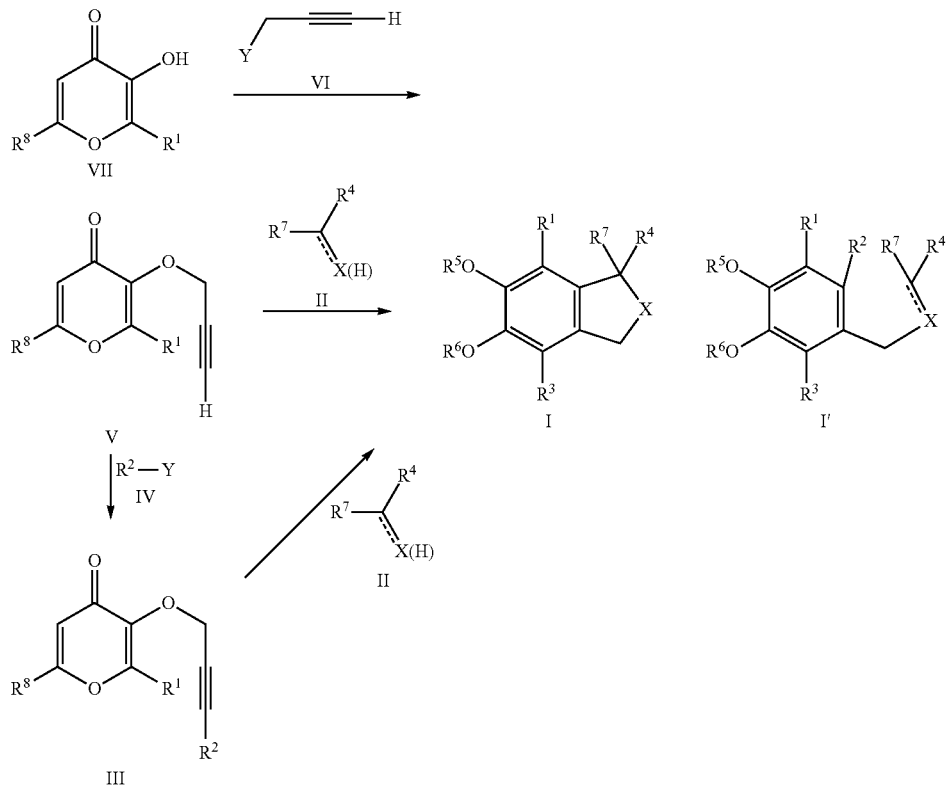

where: Y is halogen, particularly bromine; $R^8$ represents hydrogen or $C_{1-6}$ alkyl;

when X represents carbon, the compound II is an alkyl alkene, aryl alkene, arene, substituted arene, heteroarene or substituted heteroarene, comprising styrene, alkyl substituted styrene, halogen substituted styrene, diphenylethylene, naphthalene ethylene, 1-phenyl-1,3-butadiene, benzene, naphthalene, toluene, ethylbenzene, anisole, phenetole, 2,4,6-trimethoxybenzene, 1,2,4-trimethoxybenzene, 1,5-dimethoxynaphthalene, furan, pyran, thiophene, estrone derived alkene, and cholesterol derived alkene;

when X represents sulfur, the compound II is a mercaptan compound selected from methylmercaptan, ethanethiol, isoamyl mercaptan or benzyl mercaptan;

when X represents oxygen, the compound II is an alcoholic compound selected from methanol, ethanol, isopropanol, butanol, allyl alcohol, propargyl alcohol, isoamyl alcohol, benzyl alcohol, substituted benzyl alcohol, 2-bromo-2-propene-1-ol, 1-vinyl-phenylethanol, geraniol or dehydroepiandrosterone.

Specifically, the compound VII reacts with the compound VI to yield the compound V; the compound V further reacts with the compound IV to yield the compound III; thereafter, the carbon rearrangement of the compound V or compound III is captured by the compound II, thereby yielding the compound I or I'.

2) adding 1 equivalent of the first intermediate product V, 1-3 equivalents of a compound IV, 5% equivalent of copper iodide, 30% equivalent of bis(triphenylphosphine)palladium chloride, and 0.5 equivalent of sodium iodide to the organic solvent, thereby yielding a second mixture; stirring the second mixture, thereby yielding a second intermediate product III; and 3) dissolving the first intermediate product V or the second intermediate product III, and a compound II in the organic solvent, thereby yielding a third mixture; heating the third mixture; evaporating the organic solvent to yield a third product, separating and purifying the third product, thereby yielding a compound I or I'.

Particularly, in 1) and 2), the base is selected from the group consisting of lithium hydroxide, sodium hydroxide, potassium hydroxide, calcium hydroxide, sodium carbonate, potassium carbonate, calcium carbonate, sodium bicarbonate, potassium bicarbonate, sodium tert-butoxide, potassium tert-butoxide, potassium phosphate, dipotassium phosphate, cesium carbonate, lithium carbonate, pyridine, triethylamine, tributylamine, or a mixture thereof.

Particularly, in 1) and 2), the base is lithium hydroxide or potassium tert-butoxide.

Particularly, in 1), the reaction temperature of the compound VII and the compound VI is 30-80° C. for 5-24 hours.

Particularly, in 2), the first intermediate product V reacts with the compound IV at room temperature for 5-24 hours.

Particularly, in 3), the carbon arrangement of the first intermediate product V and the second intermediate product III occurs at 80-180° C. for 5-24 hours.

Particularly, in 1)-3), the organic solvent is selected from the group consisting of methanol, ethanol, isopropanol, tetrahydrofuran, 1,4-dioxane, ethyl acetate, cyclohexane, toluene, xylene, ethylbenzene, chlorobenzene, bromobenzene, dichloromethane, dichloroethane, trichloromethane, carbon tetrachloride, acetonitrile, acetone, N, N-dimethylacetamide, N, N-dimethylformamide, dimethyl sulfoxide, or a mixture thereof.

Particularly, in 1)-3), the organic solvent is chlorobenzene or acetonitrile.

The operations of separation and purification comprise silica gel column chromatography, recrystallization, thin layer chromatography, preparative chromatography or distillation.

The disclosure also provides a use of the polysubstituted benzene for preparation of an antitumor pharmaceutical composition, and a use of the polysubstituted benzene for preparation of a pharmaceutical composition for treatment of gastric cancer, ovarian cancer, lung cancer, or prostate cancer.

Compared with the technology in the prior art, advantages of the polysubstituted benzene according to embodiments of the disclosure are summarized as follows:

(1) The compound of the disclosure has good biological activity, has the activity of inhibiting the proliferation of tumor cells, and the inhibitory effect on tumor cells is better than or equal to that of the natural product gossypol I-A9. The compound can be used for the research and development of new drugs, for the preparation of anti-tumor drugs, gastric cancer drugs, ovarian cancer drugs, lung cancer drugs or prostate cancer drugs.

(2) The preparation method is easy to operate, the raw materials involved therein are easily available, and the method has step economy, mild reaction conditions, low cost, and can be easily scaled-up to an industrial process.

DETAILED DESCRIPTION

To further illustrate the invention, embodiments detailing a polysubstituted benzene are described below. It should be noted that the following embodiments are intended to describe and not to limit the disclosure.

In certain embodiments, unless otherwise stated, the involved materials were purchased commercially or prepared by those skilled in the art through conventional experimental methods, and the salt used were prepared by compounds through conventional methods, In certain embodiments, gossypol I-A9, a natural product used as a comparison compound, has the following structural formula:

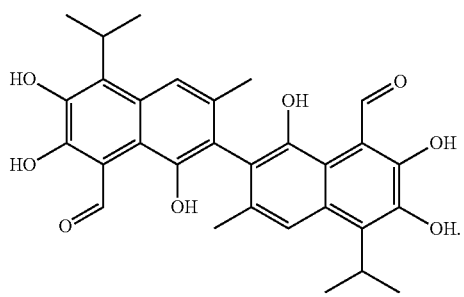

Example 1

Preparation of 2-methyl-3-(propyl-2-alkyne-1-oxy)-4H-pyran-4-one (Compound V-1)

The synthetic route is as follows:

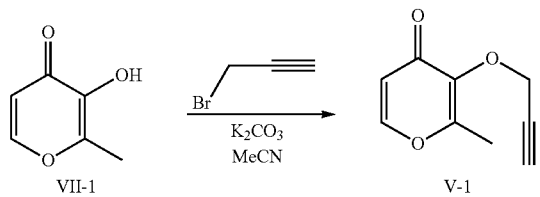

Specifically, 1.5 g of 3-hydroxy-2-methyl-4-pyrone (compound WI-1), 3 equivalents of potassium carbonate and 1.2 equivalents of propargyl bromide were added to 300 mL of acetonitrile. The mixture was heated to 80° C. and held for 12 hours. Thereafter, the mixture was filtered using a silica gel column; the solvent was evaporated under reduced pressure. The remaining solution was separated through column chromatography, thereby obtaining 17.2 g of the compound V-1, with a yield of 88%. $^1$H NMR (400 MHz, CDCl$_3$) δ 7.63 (d, J=5.6 Hz, 1H), 6.39-6.30 (m, 1H), 4.88 (d, J=2.4 Hz, 2H), 2.44 (t, J=2.4 Hz, 1H), 2.38 (s, 3H). $^{13}$C NMR (101 MHz, CDCl$_3$) δ 174.84, 160.82, 153.77, 143.02, 117.29, 79.19, 75.75, 58.85, 15.42.

Example 2

Preparation of 5,6-dihydroxy-7-methyl-1-phenyl-2,3-dihydro-1H-indene-4-carbaldehyde (Compound I-2)

The synthetic route is as follows:

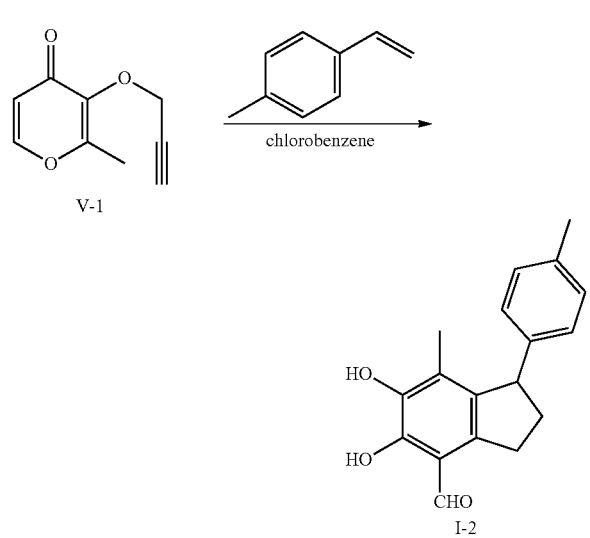

Specifically, 0.25 mmol of Compound v-1, 3.5 equivalents of p-methylphenylene and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 50.1 mg of yellow solid, that is, Compound I-2, with a yield of 70%.

Example 3

Preparation of 1-(3-bromophenyl)-5,6-dihydroxy-7-methyl-2,3-dihydro-1H-indene-4-carbaldehyde (Compound I-10)

The synthetic route is as follows:

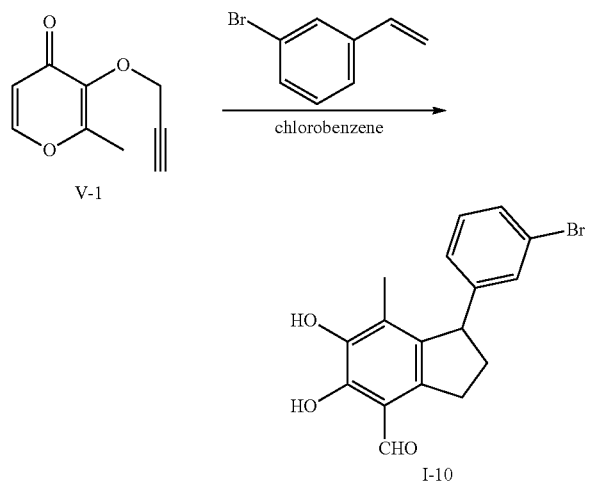

Specifically, 0.25 mmol of Compound v-1, 3.5 equivalents of 3-bromostyrene and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 45 mg of yellow solid, that is, Compound I-10, with a yield of 52%.

Example 4

Preparation of 6-((3,4-dihydro-2H-pyran-5-yl)methyl)-2,3-dihydroxy-4-methylbenzaldehyde (Compound I-14)

The synthetic route is as follows:

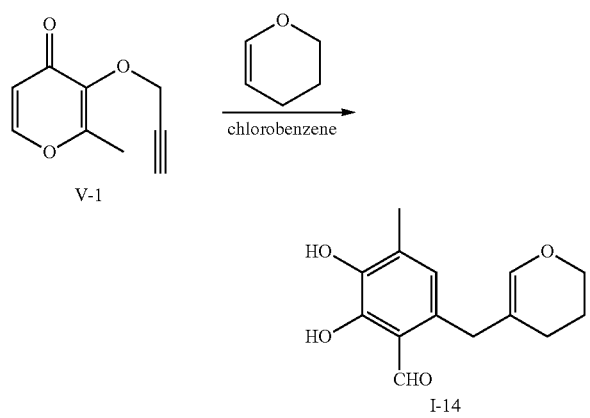

Specifically, 0.25 mmol of Compound V-1, 3.5 equivalents of 3,4-dihydro-2H-pyran and 1 mL of chlorobenzene were added to a Schlenk tube. The mixture was heated to 180° C. and held for 5 hours under nitrogen atmosphere. Thereafter, the mixture was cooled to room temperature, spin-dried, and separated using column chromatography, thereby obtaining 24 mg of yellow solid, that is, Compound I-14, with a yield of 38%.

Example 5

Preparation of 5,6-dihydroxy-7-isopropyl-1-phenyl-2,3-dihydro-1H-indene-4-carbaldehyde (Compound I-50)

The synthetic route is as follows:

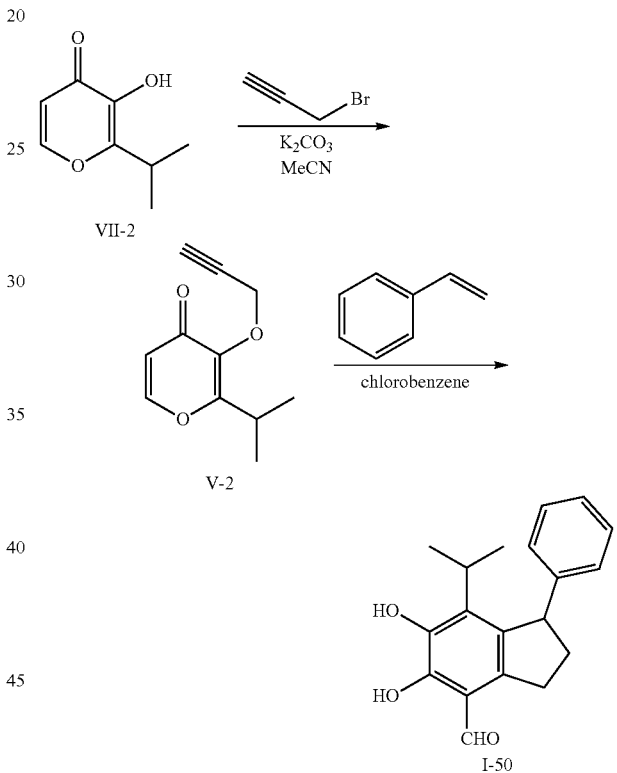

Specifically, 6.8 g of 3-hydroxy-2-isopropyl-4-pyrone (Compound VII-2), 3.0 equivalents of potassium carbonate and 1.2 equivalents of propargyl bromide were added to 150 mL of acetonitrile. The mixture was heated to 80° C. and held for 5 hours. Thereafter, the mixture was filtered using a silica gel column; the solvent was evaporated under reduced pressure. The remaining solution was separated through column chromatography, thereby obtaining 8.0 g of Compound V-2, with a yield of 94%.

0.2 mmol of Compound V-2, 3.5 equivalents of styrene and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 30 mg of yellow solid, that is, Compound I-50, with a yield of 50%.

Example 6

Preparation of 5,6-dihydroxy-4-methyl-8H-indeno(2,1-b) thiophene-7-carbaldehyde (Compound I-54)

The synthetic route is as follows:

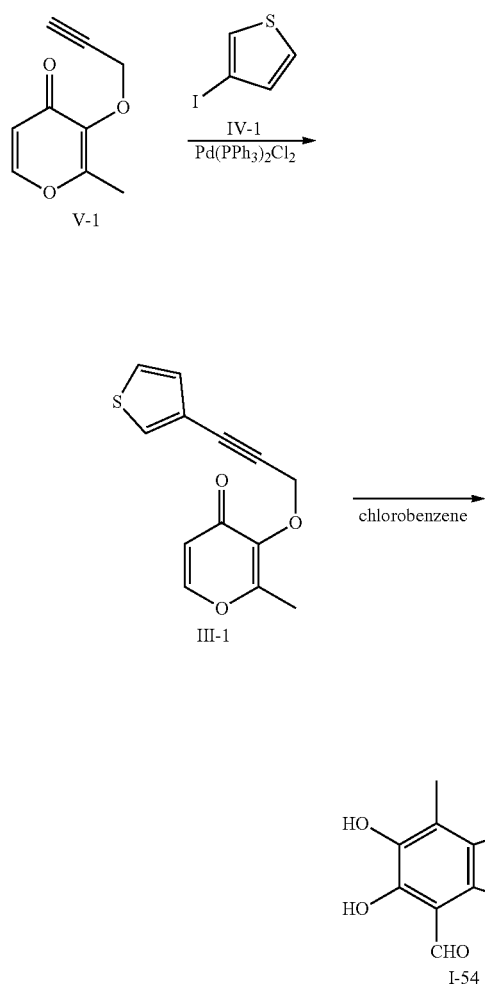

(1) Specifically, 1 mmol of Compound V-1, 0.05 mmol of copper (I) iodide, 0.03 mmol of Bis(triphenylphosphine) palladium(II) dichloride, 20 mL of tetrahydrofuran (THF), 2 mL of triethylamine and 1.2 mmol of Compound IV-1 were added sequentially to a 50 mL Schlenk tube under nitrogen atmosphere. The mixture was stirred at 30° C. until TLC analysis confirmed complete conversion of the raw materials. Thereafter, the mixture was filtered, spin-dried, dry-loaded onto a column, and separated using column chromatography, thereby obtaining 126 mg of yellow solid, that is, Compound III-1, with a yield of 51%.

(2) 0.25 mmol of Compound III-1 and 1 mL of chlorobenzene were added to a Schlenk tube. The mixture was heated to 80° C., held for 24 hours under nitrogen atmosphere. Thereafter, the mixture was cooled to room temperature, spin-dried, and separated using column chromatography, thereby obtaining 38 mg of yellow solid, that is, Compound I-54, with a yield of 60%.

Example 7

Preparation of 1-(5,6-dihydroxy-1-phenyl-7-((prop-2-yn-1-yloxy) methyl)-2,3-dihydro-1H-inden-4-yl) ethan-1-one (Compound I-A1)

The synthetic route is as follows:

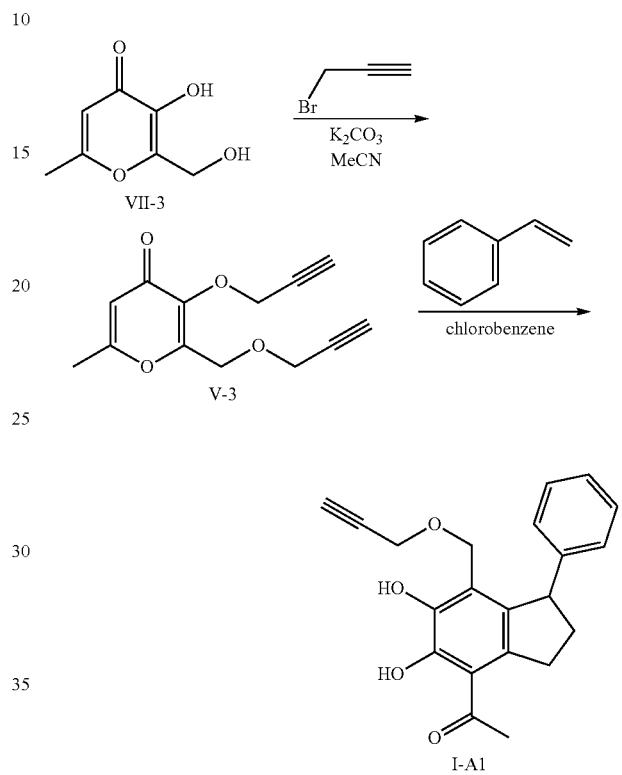

(1) Specifically, 0.8 g of Compound VII-3, 4.0 equivalents of potassium carbonate and 2.0 equivalents of propargyl bromide were added to 15 mL of acetonitrile. The mixture was heated to 80° C. and held for 12 hours. Thereafter, the mixture was filtered using a silica gel column; the solvent was evaporated under reduced pressure. The remaining solution was separated through column chromatography, thereby obtaining 0.64 g of Compound V-3, with a yield of 54%.

(2) 0.25 mmol of Compound V-3, 3.5 equivalents of styrene and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 25 mg of yellow solid, that is, Compound I-A1, with a yield of 30%.

Example 8

Preparation of (3S, 8S, 9S, 10R, 13R, 14S, 17R)-10,13-dimethyl-17-((R)-6-methylhept-2-yl)-2, 3, 4, 7, 8, 9, 10, 11, 12, 13, 14, 15, 16, 17-tetrahydro-1H-cyclopenta (a) phenanthrene-3-yl 4-((R)-4-formyl-5, 6-dihydroxy-7-methyl-2,3-dihydro-1H-inden-1-yl) methyl benzoate (Compound I-68)

The synthetic route is as follows:

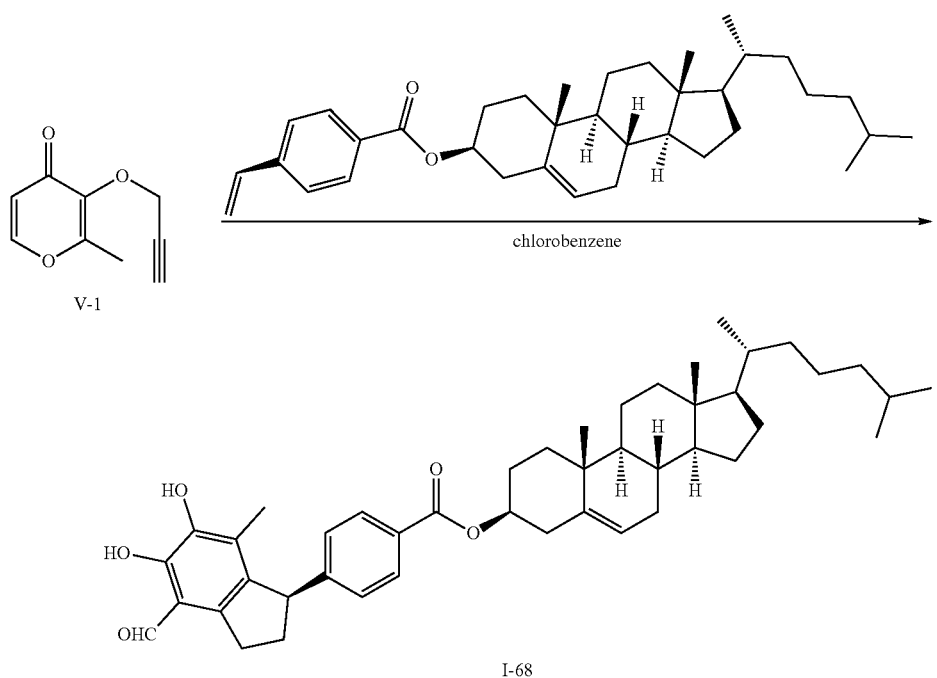

Specifically, 0.20 mmol of cholesterol derived 4-vinyl-benzoic acid, 3.0 equivalents of the Compound V-I and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 56 mg of yellow solid, that is, Compound I-68, with a yield of 41%.

Example 9

Preparation of 1-((4-bromophenyl) ethynyl)-5,6-dihydroxy-7-methyl-2,3-dihydro-1H-indene-4-carbaldehyde (Compound I-68)

The synthetic route is as follows:

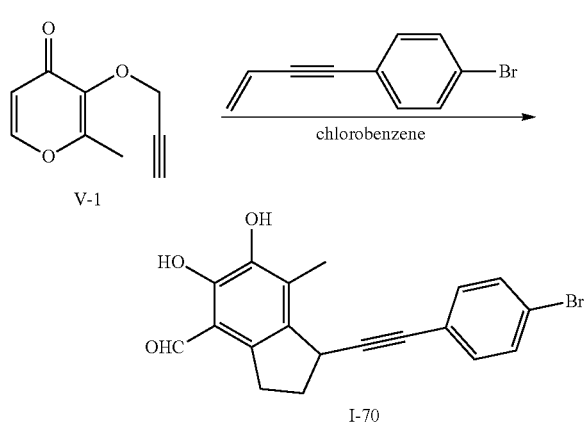

Specifically, 0.25 mmol of the Compound V-I, 3.5 equivalents of 1-bromo-4-buteneynyl benzene and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 56 mg of yellow solid, that is, Compound I-70, with a yield of 60%.

Example 10

Preparation of 2,3-dihydroxy-6-(methoxymethyl)-4-methylbenzaldehyde (Compound I-19)

The synthetic route is as follows:

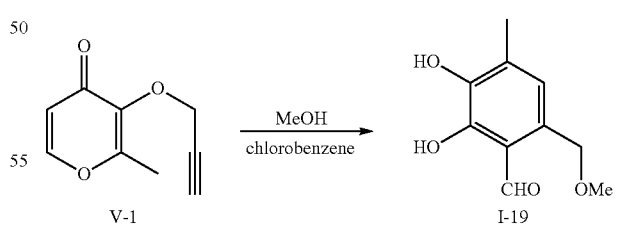

Specifically, 0.25 mmol of the Compound V-I, 3.5 equivalents of methanol and 1 mL of toluene were added to a Schlenk tube. The mixture was heated to 120° C. and held for 20 hours under nitrogen atmosphere. Thereafter, the mixture was cooled to room temperature, spin-dried, and separated using column chromatography, thereby obtaining 20 mg of yellow solid, that is, Compound I-19, with a yield of 40%.

Example 11

Preparation of 6-((benzyloxy) methyl)-2,3-dihydroxy-4-methylbenzaldehyde (Compound I-21)

The synthetic route is as follows:

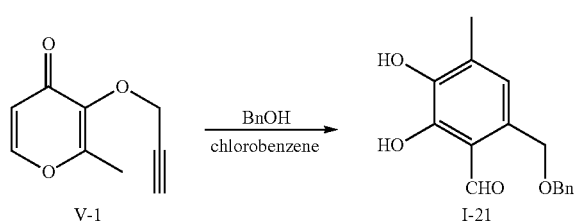

Specifically, 0.25 mmol of Compound V-I, 3.5 equivalents of benzyl alcohol and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 47 mg of yellow solid, that is, Compound I-21, with a yield of 64%.

Example 12

Preparation of 2-((benzyloxy) methyl)-3-bromo-5,6-dihydroxy-4-methylbenzaldehyde (Compound I-A8)

The synthetic route is as follows:

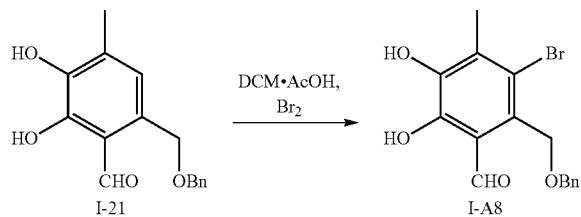

Specifically, 0.2 mmol of Compound I-21 was dissolved in a mixed solution containing 0.5 mL of dichloromethane and 0.5 mL of acetic acid, followed by a slow drop of 2.0 equivalents of liquid bromine. The mixture was rested at room temperature for 10 h, quenched with saturated sodium thiosulfate, and extracted with dichloromethane. Thereafter, the mixture was washed sequentially with saturated sodium bicarbonate solution and saturated brine, spin-dried, and separated using column chromatography, thereby obtaining 41 mg of yellow solid, that is, Compound I-A8, with a yield of 58%.

Example 13

Preparation of 2'-((benzyloxy) methyl)-3'-formyl-4',5'-dihydroxy-6'-methyl-(1,1'-biphenyl)-4-carboxylic acid methyl ester (Compound I-77)

The synthetic route is as follows:

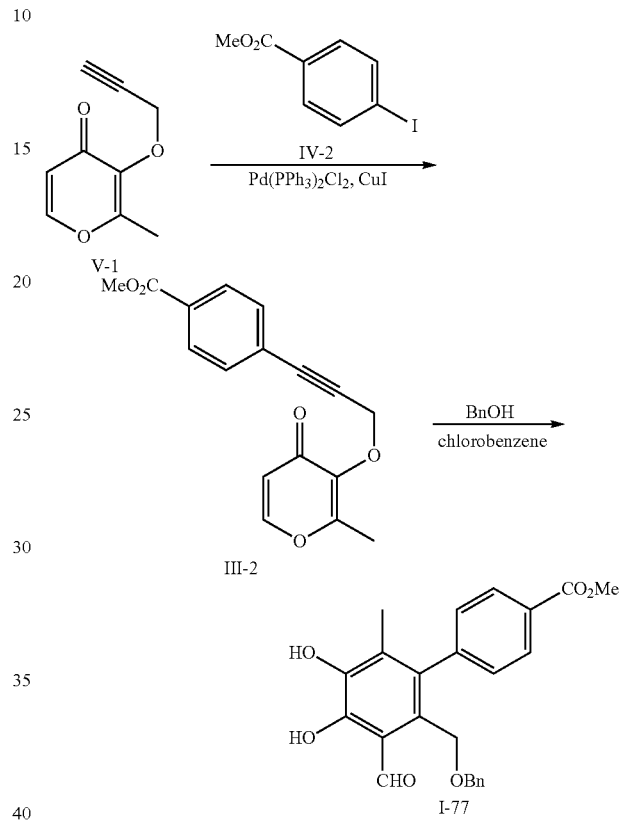

(1) Specifically, 1 mmol of Compound V-1, 0.05 mmol of copper (I) iodide, 0.03 mmol of Bis(triphenylphosphine) palladium(II) dichloride, 20 mL of tetrahydrofuran (THF), 2 mL of triethylamine and 1.2 mmol of Compound IV-1 were added sequentially to a 50 mL Schlenk tube under nitrogen atmosphere. The mixture was stirred at room temperature until TLC analysis confirmed complete conversion of the raw materials. Thereafter, the mixture was filtered, spin-dried, dry-loaded onto a column, and separated using column chromatography, thereby obtaining 233 mg of yellow solid, that is, Compound III-2, with a yield of 78%.

(2) 0.2 mmol of Compound III-2, 3.5 equivalents of benzyl alcohol and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 29 mg of yellow solid, that is, Compound I-77, with a yield of 35%.

Example 14

Preparation of 6-((((3S, 8R, 9S, 10R, 13S, 14S)-10, 13-dimethyl-17-oxo 2, 3, 4, 7, 8, 9, 10, 11, 12, 13, 14,15, 16, 17-tetrahydro-1H-cyclopenta (a) phenanthrene-3-yl) oxy) methyl)-2,3-dihydroxy-4-methylbenzene (Compound I-83)

The synthetic route is as follows:

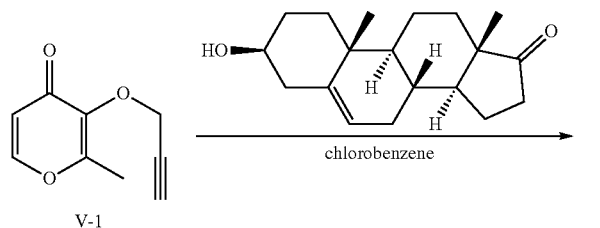

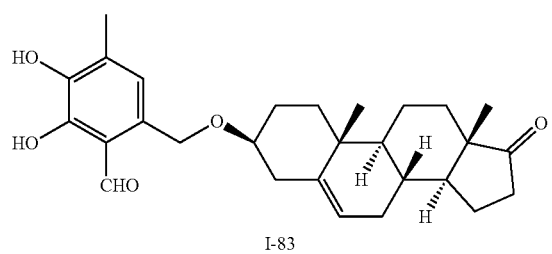

Specifically, 0.20 mmol of dehydroepiandrosterone, 3.0 equivalents of Compound V-1 and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 48 mg of yellow solid, that is, Compound I-83, with a yield of 52%.

Example 15

Preparation of 3'-formyl-4', 5'-dihydroxy-2'-((isopentyloxy) methyl)-6'-methyl-(1,1'-biphenyl)-4-carbaldehyde (Compound I-86)

The synthetic route is as follows:

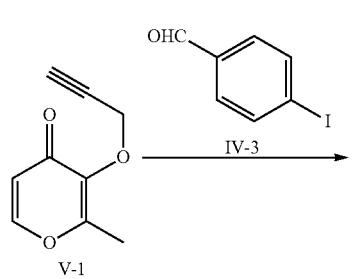

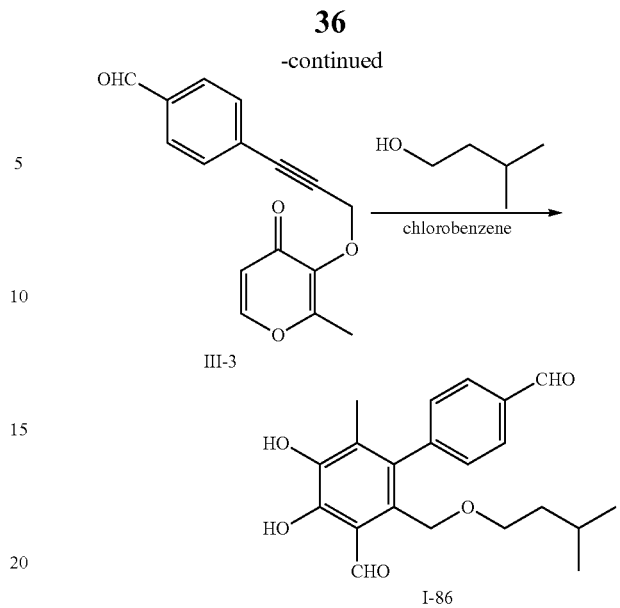

(1) Specifically, 1 mmol of Compound V-1, 0.05 mmol of copper (I) iodide, 0.03 mmol of Bis(triphenylphosphine) palladium(II) dichloride, 20 mL of tetrahydrofuran (THF), 2 mL of triethylamine and 1.2 mmol of Compound IV-3 were added sequentially to a 50 mL Schlenk tube under nitrogen atmosphere. The mixture was stirred at room temperature until TLC analysis confirmed complete conversion of the raw materials. Thereafter, the mixture was filtered, spin-dried, dry-loaded onto a column, and separated using column chromatography, thereby obtaining 185 mg of yellow solid, that is, Compound III-3, with a yield of 69%.

(2) 0.25 mmol of Compound III-6, 3.5 equivalents of isoamyl alcohol and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 49 mg of yellow solid, that is, Compound I-86, with a yield of 68%.

Example 16

Preparation of 2,3-dihydroxy-6-(((4-methoxybenzyl) oxy) methyl)-4-methylbenzaldehyde (Compound I-87)

The synthetic route is as follows:

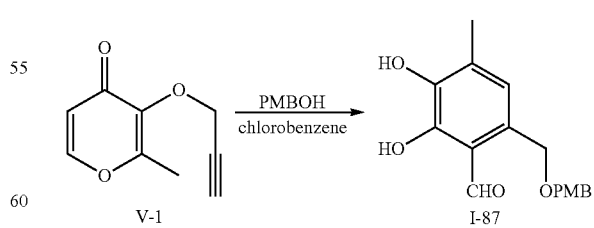

Specifically, 6.3 g of Compound V-1, 3.5 equivalents of p-methoxybenzyl alcohol and 80 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 6.0 g of yellow solid, that is, Compound I-87, with a yield of 51%.

Example 17

Preparation of 2-((benzyloxy) methyl)-3-(((tert-butyldimethylsilyl) oxy) methyl)-5,6-dihydroxy-4-methylbenzaldehyde (Compound I-89)

The synthetic route is as follows:

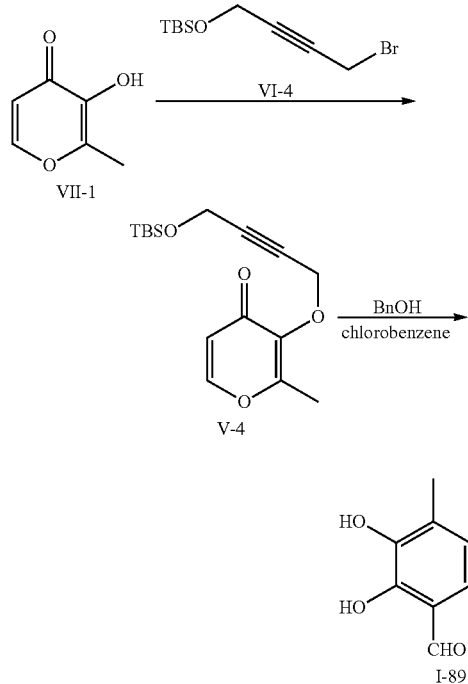

(1) Specifically, 1 mmol of 3-hydroxy-2-methyl-4-pyrone (compound WI-1), 3.0 equivalents of potassium carbonate and 1.2 equivalents of propargyl bromide (Compound VI-4) were added to 5 mL of acetonitrile. The mixture was heated to 80° C. and held for 12 hours. Thereafter, the mixture was filtered using a silica gel column; the solvent was evaporated under reduced pressure. The remaining solution was separated through column chromatography, thereby obtaining 154 mg of the compound V-4, with a yield of 50%.

(2) 0.25 mmol of Compound V-4, 3.5 equivalents of benzyl alcohol and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 40 mg of yellow solid, that is, Compound I-89, with a yield of 38%.

Example 18

Preparation of 3-allyl-2-((benzyloxy) methyl)-5,6-dihydroxy-4-isopropylbenzaldehyde (Compound I-91)

The synthetic route is as follows:

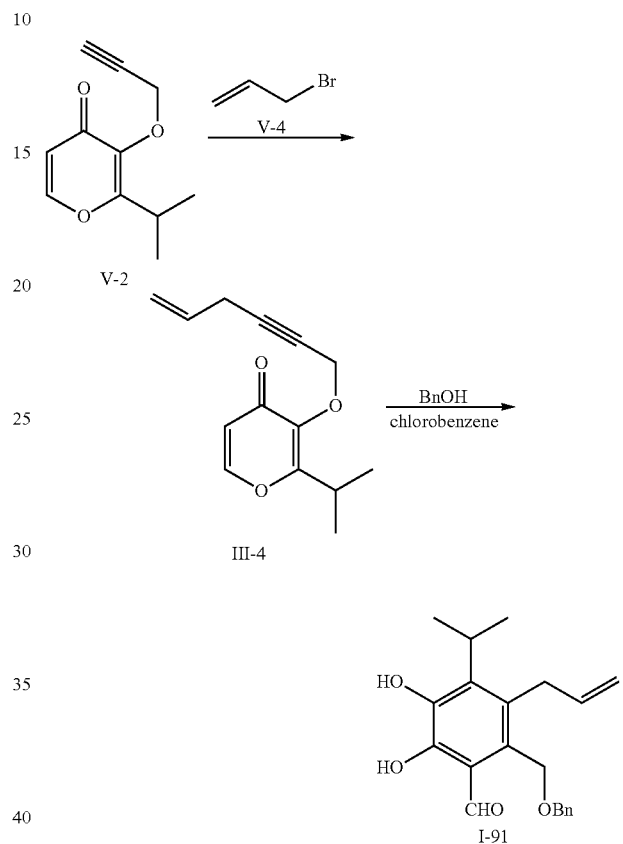

(1) Specifically, 8.0 g of Compound V-2, 0.1 eq of copper (I) iodide, 0.5 eq of sodium iodide, 120 mL of acetone, 1.2 eq of Compound IV-4 and 3.0 eq of potassium carbonate were added sequentially to a 250 mL round-bottom flask. The mixture was stirred at room temperature until TLC analysis confirmed complete conversion of the raw materials. Thereafter, the mixture was filtered, spin-dried, dry-loaded onto a column, and separated using column chromatography, thereby obtaining 8.2 g of yellow solid, that is, Compound III-4, with a yield of 85%.

(2) 5.2 g of Compound III-4, 3.5 equivalents of benzyl alcohol and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 3.35 g of yellow solid, that is, Compound I-91, with a yield of 40%.

Example 19

Preparation of 4,5-dihydroxy-6-methyl-4'-nitro-2-(2,4,6-trimethoxybenzyl)-(1,1'-biphenyl)-3-carbaldehyde (Compound I-42)

The synthetic route is as follows:

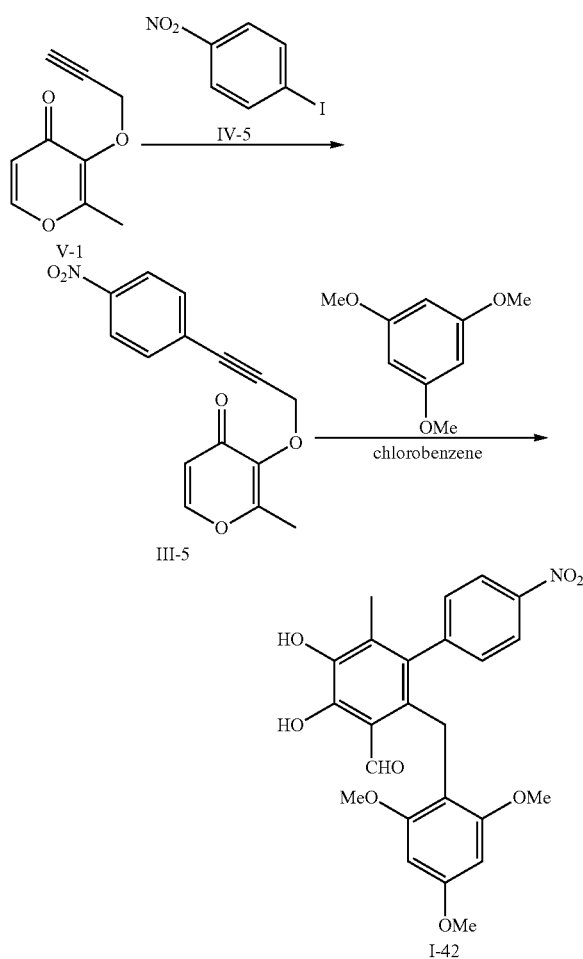

(1) Specifically, 1 mmol of Compound V-1, 0.05 mmol of copper (I) iodide, 0.03 mmol of Bis(triphenylphosphine) palladium(II) dichloride, 20 mL of tetrahydrofuran (THF), 2 mL of triethylamine and 1.2 mmol of Compound IV-5 were added sequentially to a 50 mL Schlenk tube under nitrogen atmosphere. The mixture was stirred at room temperature until TLC analysis confirmed complete conversion of the raw materials. Thereafter, the mixture was filtered, spin-dried, dry-loaded onto a column, and separated using column chromatography, thereby obtaining 191 mg of yellow solid, that is, Compound III-5, with a yield of 67%.

(2) 0.2 mmol of Compound III-5, 3.5 equivalents of 1,3,5-trimethoxybenzene and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 70 mg of yellow solid, that is, Compound I-42, with a yield of 76%.

Example 20

Preparation of 6-ethyl-4,5-dihydroxy-2-(2,4,6-trimethoxybenzyl-(1,1'-biphenyl)-3-carbaldehyde (Compound I-44)

The synthetic route is as follows:

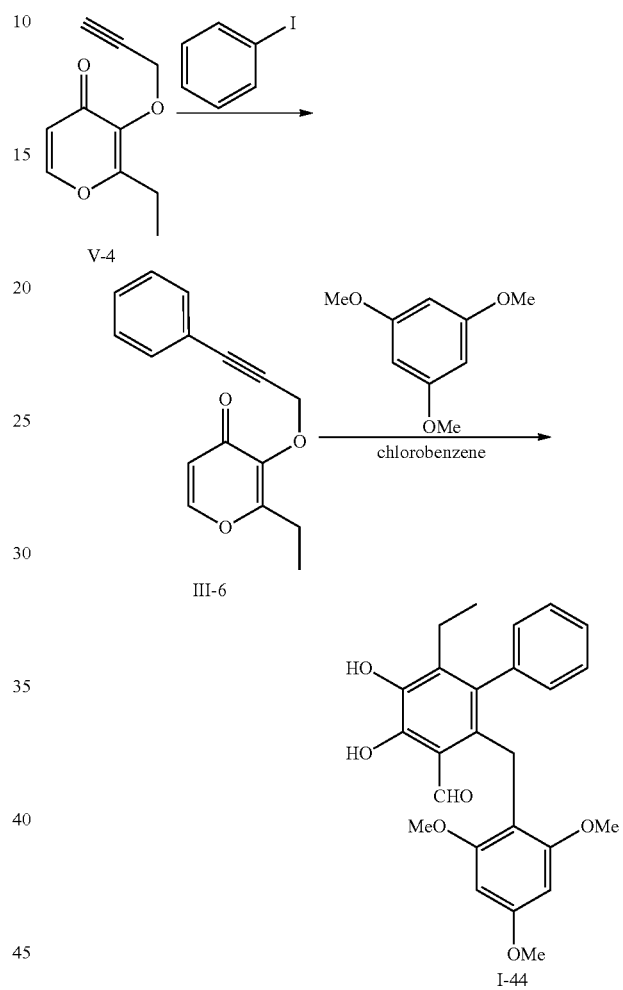

(1) Specifically, 1 mmol of Compound V-4, 0.05 mmol of copper (I) iodide, 0.03 mmol of Bis(triphenylphosphine) palladium(II) dichloride, 20 mL of tetrahydrofuran (THF), 2 mL of triethylamine and 1.2 mmol of iodobenzene were added sequentially to a 50 mL Schlenk tube under nitrogen atmosphere. The mixture was stirred at room temperature until TLC analysis confirmed complete conversion of the raw materials. Thereafter, the mixture was filtered, spin-dried, dry-loaded onto a column, and separated using column chromatography, thereby obtaining 180 mg of yellow solid, that is, Compound III-6, with a yield of 71%.

(2) 0.2 mmol of Compound III-6, 3.5 equivalents of 1,3,5-trimethoxybenzene and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 56 mg of yellow solid, that is, Compound I-44, with a yield of 65%.

Example 21

Preparation of 6-((1,5-dimethoxynaphthalen-2-yl)methyl)-2,3-dihydroxy-4-methylbenzaldehyde (Compound I-43)

The synthetic route is as follows:

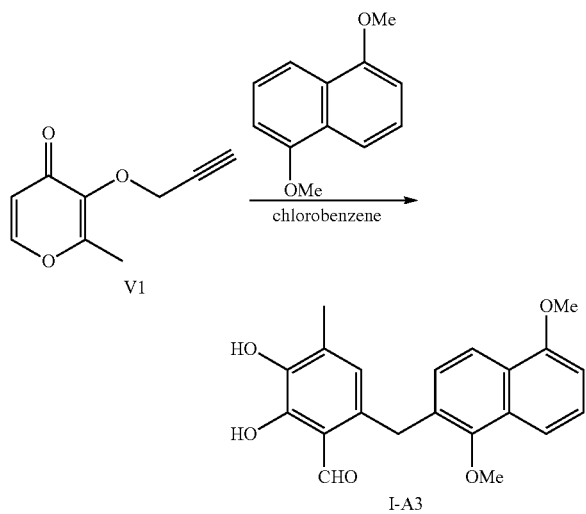

0.25 mmol of Compound V-1, 3.5 equivalents of 1,5-dimethoxynaphthalene and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 25 mg of yellow solid, that is, Compound I-43, with a yield of 28%.

Example 22

Preparation of 3-(furan-2-yl)-5,6-dihydroxy-4-methyl-2-(2,4,6-trimethoxybenzyl) benzaldehyde (Compound I-A6)

The synthetic route is as follows:

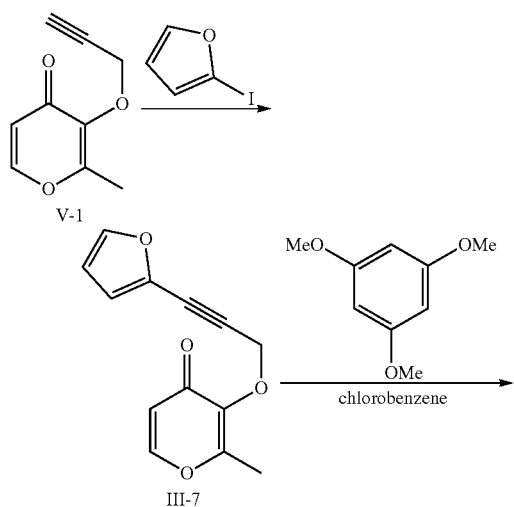

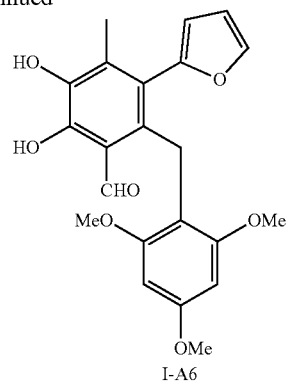

(1) Specifically, 1 mmol of Compound V-1, 0.05 mmol of copper (I) iodide, 0.03 mmol of Bis(triphenylphosphine)palladium(II) dichloride, 20 mL of tetrahydrofuran (THF), 2 mL of triethylamine and 1.2 mmol of 2-iodofuran were added sequentially to a 50 mL Schlenk tube under nitrogen atmosphere. The mixture was stirred at room temperature until TLC analysis confirmed complete conversion of the raw materials. Thereafter, the mixture was filtered, spin-dried, dry-loaded onto a column, and separated using column chromatography, thereby obtaining 194 mg of yellow solid, that is, Compound III-7, with a yield of 41%.

(2) 0.16 mmol of Compound III-7, 3.5 equivalents of 1,3,5-trimethoxybenzene and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 14 mg of yellow solid, that is, Compound I-A6, with a yield of 22%.

Example 23

Preparation of 4,5-dihydroxy-2-((isopentyloxy)methyl)-6-methyl-(1,1'-biphenyl)-3-carbaldehyde (Compound I-79)

The synthetic route is as follows:

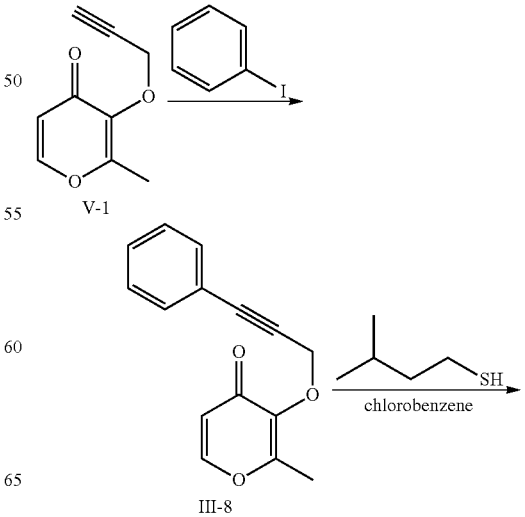

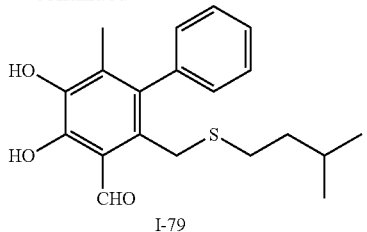
I-79

(1) Specifically, 1 mmol of Compound V-1, 0.05 mmol of copper (I) iodide, 0.03 mmol of Bis(triphenylphosphine) palladium(II) dichloride, 20 mL of tetrahydrofuran (THF), 2 mL of triethylamine and 1.2 mmol of iodobenzene were added sequentially to a 50 mL Schlenk tube under nitrogen atmosphere. The mixture was stirred at room temperature until TLC analysis confirmed complete conversion of the raw materials. Thereafter, the mixture was filtered, spin-dried, dry-loaded onto a column, and separated using column chromatography, thereby obtaining 178 mg of yellow solid, that is, Compound III-8, with a yield of 74%.

(2) 0.25 mmol of Compound III-8, 3.5 equivalents of isoamyl mercaptan and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 23 mg of yellow solid, that is, Compound I-79, with a yield of 27%.

Example 24

Preparation of 2,3,6,7-tetrahydroxy-4,5-dimethyl-9,10-dihydrophenanthrene-1,8-dicarbaldehyde (Compound I-22)

The synthetic route is as follows:

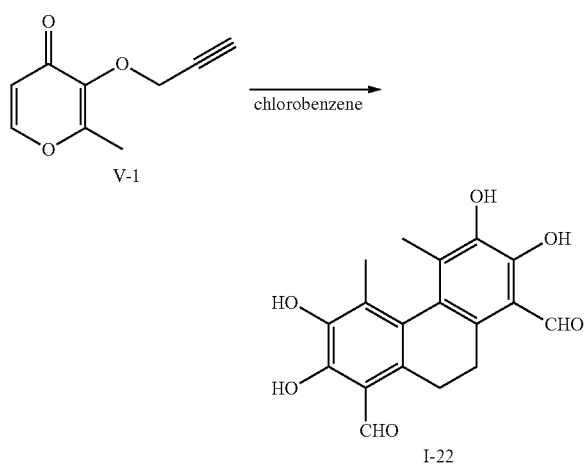

0.25 mmol of Compound V-1 and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 31 mg of yellow solid, that is, Compound I-22, with a yield of 75%.

Example 25

Preparation of 3-((1H-inden-3-yl) methyl)-5,6-dihydroxy-2,4-dimethylbenzaldehyde (Compound I-95)

The synthetic route is as follows:

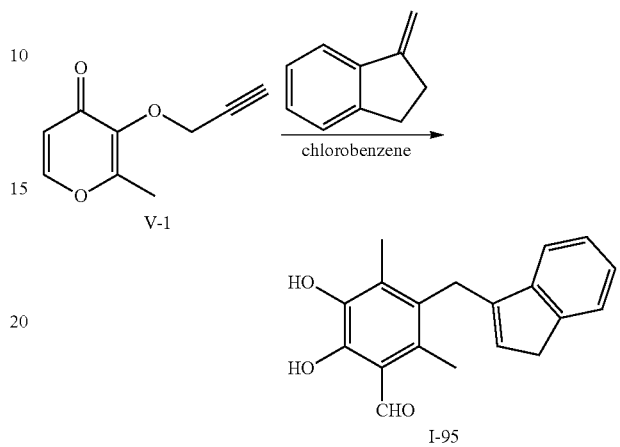

0.25 mmol of Compound V-1, 3.5 equivalents of 1-methylene-2,3-dihydroindene and 1 mL of chlorobenzene were added to a Schlenk tube. The mixture was heated to 150° C. and held for 13 hours under nitrogen atmosphere. Thereafter, the mixture was cooled to room temperature, spin-dried, and separated using column chromatography, thereby obtaining 12 mg of yellow solid, that is, Compound I-95, with a yield of 16%.

Example 26

Preparation of 4-(hydroxymethyl)-7-methyl-1-phenyl-2,3-dihydro-1H-indene-5,6-diol (Compound I-98)

The synthetic route is as follows:

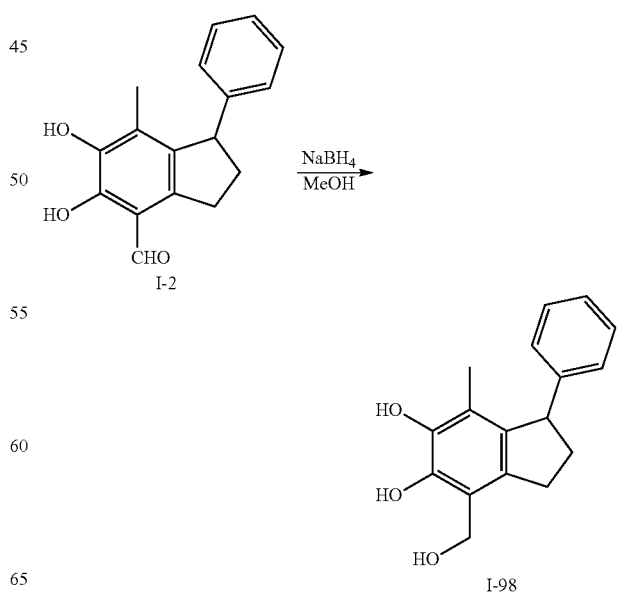

0.5 mmol of Compound I-2 was dissolved in 5 mL of methanol, and the temperature was reduced to 0° C., followed by an addition of 1.2 equivalents of sodium borohydride. After reaction for 1 h, the resulting solution was quenched with 10 mL of saturated ammonium chloride solution, rotated and evaporated to remove methanol, and extracted with ethyl acetate. The organic layers were combined together, spin-dried, and separated using column chromatography by addition of petroleum ether: ethyl acetate=1:3 (V/V), thereby obtaining 95 mg of Compound I-98, with a yield of 70%.

Example 27

Preparation of 2,3-dihydroxy-6-(((4-methoxybenzyl) oxy) methyl)-p-toluic acid (Compound I-99)

The synthetic route is as follows:

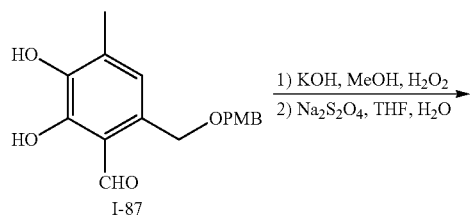

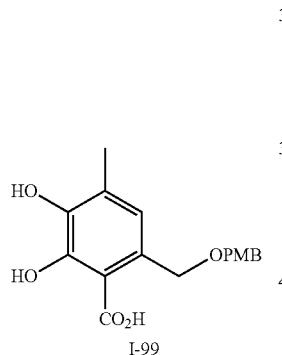

1 mmol of Compound I-87 was slowly dropped into 10 mL of methanol containing 3.0 eq of potassium hydroxide and 5.0 eq of hydrogen peroxide. The solution was rested at room temperature for 4 h, and neutralized with dilute hydrochloric acid to acidity, extracted with ethyl acetate and spin-dried. The resulting product was dissolved in tetrahydrofuran (THF) and 2 mL of saturated $Na_2S_2O_4$ solution was added. The mixture was rested at room temperature for 2 h, neutralized with dilute hydrochloric acid to acidity, extracted with ethyl acetate, dried and spin-dried, thereby obtaining 125 mg of white solid, that is, Compound I-99, with a yield of 39%.

Example 28

Preparation of methyl-2,3-dimethoxy-6-((4-methoxybenzyl) oxy) methyl)-4-methylbenzoate (Compound I-100)

The synthetic route is as follows:

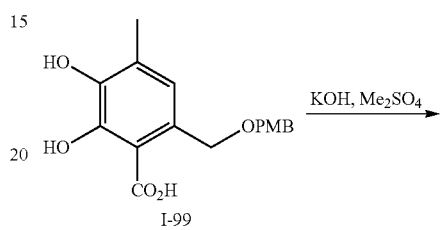

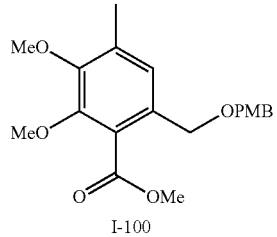

Specifically, 0.2 mmol of the compound 1-99 was dissolved in 2 mL of tetrahydrofuran, and then 5.0 eq. potassium hydroxide solution (0.5 mL) was added. The mixture was stirred and 10.0 eq. dimethyl sulfate was added. The solution was rested at room temperature until all the raw materials disappeared. The solution was neutralized with dilute hydrochloric acid, extracted with acetate, spin-dried, and separated using column chromatography, thereby obtaining 33 mg of the compound 1-100, with a yield of 46%.

The structural formulas and characterization data of the compounds prepared in Examples 1 to 28 are as follows:

| Structure and number | Characterization data $^1$HNMR, $^{13}$CNMR, Mass |
|---|---|
| | I-1 $^1$H NMR (400 MHz, CDCl$_3$) δ 11.51 (s, 1H), 10.09 (s, 1H), 7.25 (t, J = 7.3 Hz, 2H), 7.20-7.15 (m, 1H), 7.00 (d, J = 7.1 Hz, 2H), 5.66 (s, 1H), 4.37 (dd, J = 9.0, 3.2 Hz, 1H), 3.30-3.09 (m, 2H), 2.65 (dq, J = 12.9, 8.9 Hz, 1H), 2.14-2.04 (m, 1H), 1.94 (s, 3H). $^{13}$C NMR (101 MHz, CDCl$_3$) δ 195.08, 148.17, 145.32, 141.93, 137.74, 137.12, 130.71, 128.71, 127.31, 126.38, 114.56, 49.68, 35.94, 28.47, 13.37. HR-MS (ESI) calcd. for $(C_{17}H_{16}O_3 + Na)^+$ 291.0992, found: 291.0987. |

| Structure and number | Characterization data ¹HNMR, ¹³CNMR, Mass |
|---|---|
| I-2 | I-2 ¹H NMR (400 MHz, CDCl₃) δ 11.54 (s, 1H), 10.12 (s, 1H), 7.10 (d, J = 7.9 Hz, 2H), 6.92 (d, J = 8.0 Hz, 2H), 5.65 (s, 1H), 4.38 (dd, J = 9.0, 3.1 Hz, 1H), 3.33-3.10 (m, 2H), 2.67 (dq, J = 12.9, 8.9 Hz, 1H), 2.34 (s, 3H), 2.11 (ddt, J = 11.7, 8.1, 3.5 Hz, 1H), 1.99 (s, 3H).<br>¹³C NMR (101 MHz, CDCl₃) δ 195.11, 148.10, 142.26, 141.88, 137.71, 137.28, 135.89, 130.71, 129.40, 127.19, 114.55, 49.25, 36.05, 28.43, 21.12, 13.37.<br>HR-MS (ESI) calcd. for $(C_{18}H_{18}O_3 + Na)^+$ 305.1148, found: 305.1143. |
| I-3 | I-3 ¹H NMR (400 MHz, CDCl₃) δ 11.51 (s, 1H), 10.09 (s, 1H), 6.99-6.89 (m, 4H), 5.65 (s, 1H), 4.37 (dd, J = 9.0, 3.2 Hz, 1H), 3.29-3.06 (m, 2H), 2.65 (dq, J = 13.0, 8.9 Hz, 1H), 2.05 (ddt, J = 12.9, 8.0, 3.7 Hz, 1H), 1.93 (s, 3H).<br>¹³C NMR (101 MHz, CDCl₃) δ 195.04, 162.78, 160.35, 148.27, 142.05, 141.02, 140.99, 137.58, 136.93, 130.50, 128.71, 128.64, 115.61, 115.40, 114.58, 48.92, 35.98, 28.36, 13.34.<br>¹⁹F NMR (376 MHz, CDCl₃) δ −116.95.<br>HR-MS (ESI) calcd. for $(C_{17}H_{15}FO_3 + H)^+$ 287.1078, found: 287.1074. |
| I-4 | I-4 ¹H NMR (400 MHz, CDCl₃) δ 11.50 (s, 1H), 10.09 (s, 1H), 6.94-6.88 (m, 2H), 6.82-6.77 (m, 2H), 5.61 (s, 1H), 4.33 (dd, J = 8.9, 3.2 Hz, 1H), 3.77 (s, 3H), 3.28-3.08 (m, 2H), 2.62 (dq, J = 12.9, 8.8 Hz, 1H), 2.10-2.01 (m, 1H), 1.95 (s, 3H).<br>¹³C NMR (101 MHz, CDCl₃) δ 195.09, 158.17, 148.10, 141.90, 137.60, 137.41, 137.38, 130.69, 128.24, 114.55, 114.08, 55.36, 48.84, 36.06, 28.38, 13.32.<br>HR-MS (ESI) calcd. for $(C_{18}H_{18}O_4 + Na)^+$ 321.1097, found: 321.1093. |
| I-5 | I-5 ¹H NMR (400 MHz, CDCl₃) δ 11.53 (s, 1H), 10.10 (s, 1H), 7.51 (d, J = 8.1 Hz, 2H), 7.12 (d, J = 8.1 Hz, 2H), 5.66 (s, 1H), 4.45 (dd, J = 9.1, 3.1 Hz, 1H), 3.32-3.13 (m, 2H), 2.70 (dq, J = 13.0, 8.9 Hz, 1H), 2.13-2.02 (m, 1H), 1.93 (s, 3H).<br>¹³C NMR (101 MHz, CDCl₃) δ 195.00, 149.47, 148.45, 142.16, 137.70, 136.22, 130.35, 127.62, 125.74 (q, J = 3.7 Hz), 114.61, 49.48, 35.78, 28.45, 13.46.<br>¹⁹F NMR (376 MHz, CDCl₃) δ −62.35.<br>HR-MS (ESI) calcd. for $(C_{18}H_{15}F_3O_3 + Na)^+$ 359.0865, found: 359.0862. |
| I-6 | I-6 ¹H NMR (400 MHz, CDCl₃) δ 11.54 (s, 1H), 10.11 (s, 1H), 7.40 (d, J = 8.4 Hz, 2H), 6.90 (d, J = 8.4 Hz, 2H), 5.66 (s, 1H), 4.37 (dd, J = 9.0, 3.2 Hz, 1H), 3.32-3.11 (m, 2H), 2.68 (dq, J = 13.0, 8.9 Hz, 1H), 2.07 (ddd, J = 16.5, 7.6, 3.6 Hz, 1H), 1.96 (s, 3H).<br>¹³C NMR (101 MHz, CDCl₃) δ 195.00, 148.32, 144.37, 142.06, 137.63, 136.50, 131.82, 130.42, 129.05, 120.13, 114.56, 49.10, 35.82, 28.39, 13.42.<br>HR-MS (ESI) calcd. for $(C_{17}H_{15}BrO_3 + Na)^+$ 369.0097, found: 369.0092. |

| Structure and number | Characterization data ¹HNMR, ¹³CNMR, Mass |
|---|---|
| I-7 | I-7 ¹H NMR (400 MHz, CDCl₃) δ 11.54 (s, 1H), 10.11 (s, 1H), 7.27-7.22 (m, 2H), 6.99-6.92 (m, 2H), 5.66 (s, 1H), 4.38 (dd, J = 9.0, 3.2 Hz, 1H), 3.30-3.13 (m, 2H), 2.68 (dq, J = 13.0, 8.9 Hz, 1H), 2.07 (ddd, J = 16.4, 7.6, 3.7 Hz, 1H), 1.96 (s, 3H). ¹³C NMR (101 MHz, CDCl₃) δ 195.01, 148.31, 143.84, 142.05, 137.63, 136.59, 132.09, 130.44, 128.86, 128.64, 114.57, 49.04, 35.88, 28.39, 13.40. HR-MS (ESI) calcd. for (C₁₇H₁₅ClO₃ + Na)⁺ 325.0602, found: 325.0602. |
| I-8 | I-8 ¹H NMR (400 MHz, CDCl₃) δ 11.55 (s, 1H), 10.10 (s, 1H), 8.13 (d, J = 8.8 Hz, 2H), 7.18 (d, J = 8.7 Hz, 2H), 5.64 (s, 1H), 4.50 (dd, J = 9.2, 3.3 Hz, 1H), 3.33-3.16 (m, 2H), 2.74 (dq, J = 13.1, 8.9 Hz, 1H), 2.14-2.02 (m, 1H), 1.92 (s, 3H). ¹³C NMR (101 MHz, CDCl₃) δ 194.91, 153.16, 148.62, 146.78, 142.31, 137.61, 135.68, 130.06, 128.11, 124.16, 114.64, 49.54, 35.71, 28.50, 13.53. HR-MS (ESI) calcd. for (C₁₇H₁₅NO₅ + Na)⁺ 336.0842, found: 336.0843. |
| I-9 | I-9 ¹H NMR (400 MHz, CDCl₃) δ 11.42 (s, 1H), 10.00 (s, 1H), 7.17 (d, J = 8.4 Hz, 2H), 6.83 (d, J = 8.3 Hz, 2H), 5.57 (s, 1H), 4.26 (dd, J = 9.0, 3.0 Hz, 1H), 3.21-3.00 (m, 2H), 2.54 (dq, J = 12.9, 8.9 Hz, 1H), 2.02 (ddt, J = 12.8, 8.1, 3.4 Hz, 1H), 1.87 (s, 3H), 1.20 (s, 9H). ¹³C NMR (101 MHz, CDCl₃) δ 195.11, 149.13, 148.09, 142.07, 141.84, 137.67, 137.44, 130.78, 126.93, 125.50, 114.55, 49.11, 35.88, 34.47, 31.50, 28.48, 13.40. HR-MS (ESI) calcd. for (C₂₁H₂₄O₃ + Na)⁺ 347.1618, found: 347.1617. |
| I-10 | I-10 ¹H NMR (400 MHz, CDCl₃) δ 11.52 (s, 1H), 10.09 (s, 1H), 7.32 (ddd, J = 7.9, 1.9, 1.0 Hz, 1H), 7.15 (t, J = 1.8 Hz, 1H), 7.12 (t, J = 7.8 Hz, 1H), 6.92 (d, J = 7.7 Hz, 1H), 5.64 (s, 1H), 4.34 (dd, J = 9.1, 3.2 Hz, 1H), 3.28-3.12 (m, 2H), 2.66 (dq, J = 13.0, 9.0 Hz, 1H), 2.07 (ddt, J = 13.0, 8.0, 3.7 Hz, 1H), 1.95 (s, 3H). ¹³C NMR (101 MHz, CDCl₃) δ 195.01, 148.39, 147.80, 142.07, 137.69, 136.25, 130.41, 130.31, 129.60, 125.95, 122.96, 114.58, 49.38, 35.81, 28.41, 13.46. HR-MS (ESI) calcd. for (C₁₇H₁₅BrO₃ + Na)⁺ 369.0097, found: 369.0091. |
| I-11 | I-11 ¹H NMR (400 MHz, CDCl₃) δ 11.53 (s, 1H), 10.09 (s, 1H), 7.59 (dd, J = 7.7, 1.5 Hz, 1H), 7.10 (td, J = 7.4, 1.4 Hz, 1H), 7.05 (td, J = 7.6, 1.9 Hz, 1H), 6.56 (d, J = 6.9 Hz, 1H), 5.67 (s, 1H), 4.79 (dd, J = 9.2, 2.9 Hz, 1H), 3.24-3.07 (m, 2H), 2.69 (dq, J = 13.1, 9.1 Hz, 1H), 2.12-1.99 (m, 1H), 1.92 (s, 3H). ¹³C NMR (101 MHz, CDCl₃) δ 195.00, 148.36, 143.87, 142.08, 138.28, 136.29, 133.13, 130.47, 128.05, 127.72, 124.41, 114.64, 48.69, 34.15, 28.13, 13.45. HR-MS (ESI) calcd. for (C₁₇H₁₅BrO₃ + Na)⁺ 369.0097, found: 369.0091. |

| Structure and number | Characterization data $^1$HNMR, $^{13}$CNMR, Mass |
|---|---|
| I-12 | I-12 $^1$H NMR (400 MHz, CDCl$_3$) δ 11.53 (s, 1H), 10.09 (s, 1H), 7.40 (dd, J = 7.9, 1.3 Hz, 1H), 7.13 (td, J = 7.6, 1.7 Hz, 1H), 7.06 (td, J = 7.5, 1.2 Hz, 1H), 6.58 (dd, J = 7.7, 1.5 Hz, 1H), 5.66 (s, 1H), 4.82 (dd, J = 9.2, 2.8 Hz, 1H), 3.26-3.07 (m, 2H), 2.69 (dq, J = 13.1, 9.1 Hz, 1H), 2.12-2.01 (m, 1H), 1.93 (s, 3H).<br>$^{13}$C NMR (101 MHz, CDCl$_3$) δ 195.03, 148.35, 142.20, 142.07, 138.27, 136.17, 133.63, 130.48, 129.80, 127.86, 127.74, 127.07, 114.65, 45.99, 34.06, 28.22, 13.38.<br>HR-MS (ESI) calcd. for (C$_{17}$H$_{15}$ClO$_3$ + Na)$^+$ 325.0602, found: 325.0600. |
| I-13 | I-13 $^1$H NMR (400 MHz, CDCl$_3$) δ 11.52 (s, 1H), 10.09 (s, 1H), 7.32-7.16 (m, 10H), 5.62 (s, 1H), 3.02 (dd, J = 10.5, 3.6 Hz, 2H), 2.91 (dd, J = 10.5, 3.7 Hz, 2H), 1.57 (s, 3H).<br>$^{13}$C NMR (101 MHz, CDCl$_3$) δ 195.15, 147.90, 145.44, 142.17, 139.99, 138.15, 132.28, 129.03, 128.16, 126.43, 114.64, 62.42, 48.82, 27.58, 13.58.<br>HR-MS (ESI) calcd. for (C$_{23}$H$_{20}$O$_3$ + Na)$^+$ 367.1305, found: 367.1298. |
| I-14 | I-14 $^1$H NMR (400 MHz, CDCl$_3$) δ 12.11 (s, 1H), 10.22 (s, 1H), 6.55 (s, 1H), 6.16 (s, 1H), 5.65 (s, 1H), 3.95-3.85 (m, 2H), 3.42 (s, 2H), 2.30 (s, 3H), 1.96-1.80 (m, 4H).<br>$^{13}$C NMR (101 MHz, CDCl$_3$) δ 195.37, 149.76, 141.61, 141.19, 133.45, 132.54, 123.85, 116.50, 113.13, 108.52, 65.52, 35.38, 23.50, 22.49, 16.37.<br>HR-MS (ESI) calcd. for (C$_{14}$H$_{16}$O$_4$ + Na)$^+$ 271.0941, found: 271.0939. |
| I-15 | I-15 $^1$H NMR (400 MHz, CDCl$_3$) δ 11.47 (s, 1H), 10.08 (s, 1H), 7.42 (d, J = 8.4 Hz, 2H), 7.19 (d, J = 8.5 Hz, 2H), 6.23 (s, 1H), 5.63 (d, J = 4.9 Hz, 1H), 4.02-3.92 (m, 1H), 3.19 (dd, J = 8.6, 3.2 Hz, 2H), 2.51-2.41 (m, 1H), 2.25 (s, 3H), 2.18-2.07 (m, 1H).<br>$^{13}$C NMR (101 MHz, CDCl$_3$) δ 194.88, 147.84, 141.63, 137.12, 136.18, 135.86, 132.78, 131.60, 131.52, 130.42, 130.30, 128.03, 127.67, 120.89, 114.65, 46.68, 32.79, 28.10, 13.05.<br>HR-MS (ESI) calcd. for (C$_{19}$H$_{17}$BrO$_3$ + Na)$^+$ 395.0253, found: 395.0250. |
| I-16 | I-16 $^1$H NMR (400 MHz, CDCl$_3$) δ 11.42 (s, 1H), 10.01 (s, 1H), 7.43 (ddd, J = 7.5, 4.4, 1.2 Hz, 2H), 7.38-7.34 (m, 1H), 7.29-7.26 (m, 2H), 7.24-7.17 (m, 5H), 5.99 (d, J = 10.5 Hz, 1H), 5.61 (s, 1H), 3.92-3.82 (m, 1H), 3.26 (dt, J = 16.1, 8.1 Hz, 1H), 3.07 (ddd, J = 16.0, 9.1, 4.9 Hz, 1H), 2.47-2.36 (m, 1H), 2.18-2.06 (m, 1H), 2.10 (s, 3H).<br>$^{13}$C NMR (101 MHz, CDCl$_3$) δ 194.97, 147.84, 142.33, 141.73, 140.96, 140.10, 137.41, 136.85, 131.96, 130.66, 130.02, 128.50, 128.29, 127.42, 127.39, 127.31, 114.62, 44.30, 33.43, 28.61, 13.06.<br>HR-MS (ESI) calcd. for (C$_{25}$H$_{22}$O$_3$ + Na)$^+$ 393.1461, found: 393.1458. |
| I-17 | I-17 $^1$H NMR (400 MHz, CDCl$_3$) δ 12.11 (s, 1H), 10.10 (s, 1H), 7.22 (d, J = 7.5 Hz, 1H), 7.15 (d, J = 7.2, 1H), 7.11-7.02 (m, 2H), 6.49 (s, 1H), 3.29 (m, 1H), 3.14-3.04 (m, 1H), 3.04-2.98 (m, 2H), 2.86 (m, 2H), 2.75-2.66 (m, 1H), 2.53 (m, 1H), 2.27 (s, 3H), 1.88 (m, 1H), 1.84-1.75 (m, 1H) s..<br>$^{13}$C NMR (101 MHz, CDCl$_3$) δ 195.07, 147.70, 142.45, 136.64, 135.10, 134.32, 130.30, 128.55, 128.02, 127.07, 125.77, 123.20, 122.43, 43.93, 36.43, 33.25, 27.21, 23.11, 21.20, 16.36.<br>HR-MS (ESI) calcd. for (C$_{20}$H$_{22}$O$_3$ + Na)$^+$ 331.1305, found: 331.1302. |

| Structure and number | Characterization data $^1$HNMR, $^{13}$CNMR, Mass |
|---|---|
| I-18 | $^1$H NMR (400 MHz, CDCl$_3$) δ 12.24 (s, 1H), 10.53 (s, 1H), 6.51 (s, 1H), 6.14 (s, 2H), 5.53 (s, 1H), 4.11 (s, 2H), 3.81 (s, 3H), 3.78 (s, 6H), 2.19 (s, 3H).<br>$^{13}$C NMR (101 MHz, CDCl$_3$) δ 196.87, 160.20, 158.80, 149.11, 140.74, 136.27, 132.44, 122.74, 116.38, 109.29, 90.89, 55.74, 55.48, 23.17, 16.51.<br>HR-MS (ESI) calcd. for (C$_{18}$H$_{20}$O$_6$ + Na)$^+$ 355.1152, found: 355.1152. |
| I-19 | $^1$H NMR (400 MHz, CDCl$_3$) δ 12.12 (s, 1H), 10.23 (s, 1H), 6.65 (s, 1H), 5.82 (s, 1H), 4.59 (s, 2H), 3.37 (s, 3H), 2.29 (s, 3H).<br>$^{13}$C NMR (101 MHz, CDCl$_3$) δ 196.17, 150.06, 143.23, 131.64, 131.01, 123.68, 116.37, 72.04, 57.98, 16.22.<br>HR-MS (ESI) calcd. for (C$_{10}$H$_{12}$O$_4$ + H)$^+$ 197.0808, found: 197.0810. |
| I-20 | $^1$H NMR (400 MHz, CDCl$_3$) δ 12.14 (s, 1H), 10.27 (s, 1H), 6.69 (s, 1H), 5.79 (s, 1H), 4.75 (s, 2H), 4.17 (d, J = 2.4 Hz, 2H), 2.50 (t, J = 2.4 Hz, 1H), 2.30 (s, 3H).<br>$^{13}$C NMR (101 MHz, CDCl$_3$) δ 196.19, 150.10, 143.48, 131.66, 130.02, 124.15, 116.39, 79.23, 75.38, 68.61, 57.18, 16.22.<br>HR-MS (ESI) calcd. for (C$_{12}$H$_{12}$O$_4$ + Na)$^+$ 243.0628, found: 243.0624. |
| I-21 | $^1$H NMR (400 MHz, CDCl$_3$) δ 12.12 (s, 1H), 10.23 (s, 1H), 7.40-7.25 (m, 5H), 6.64 (s, 1H), 5.88 (s, 1H), 4.66 (s, 2H), 4.53 (s, 2H), 2.28 (s, 3H).<br>$^{13}$C NMR (101 MHz, CDCl$_3$) δ 196.20, 150.06, 143.23, 137.68, 131.68, 130.97, 128.63, 128.06, 128.04, 123.79, 116.40, 72.35, 69.41, 16.22.<br>HR-MS (ESI) calcd. for (C$_{16}$H$_{16}$O$_4$ + Na)$^+$ 295.0941, found: 295.0941. |
| I-22 | $^1$H NMR (400 MHz, CDCl$_3$) δ 11.96 (s, 2H), 10.37 (s, 2H), 5.73 (s, 2H), 3.41 (d, J = 10.3 Hz, 2H), 2.50 (d, J = 10.4 Hz, 2H), 2.18 (s, 6H).<br>$^{13}$C NMR (101 MHz, CDCl$_3$) δ 194.88, 147.33, 141.79, 134.89, 131.87, 126.73, 115.31, 24.40, 16.06.<br>HR-MS (ESI) calcd. for (C$_{18}$H$_{16}$O$_6$ + Na)$^+$ 351.0839, found: 351.0839. |
| I-23 | $^1$H NMR (400 MHz, CDCl$_3$) δ 11.48 (s, 1H), 10.11 (s, 1H), 7.32-7.26 (m, 2H), 7.23-7.16 (m, 3H), 5.57 (s, 1H), 3.26-3.09 (m, 2H), 2.33-2.25 (m, 2H), 1.77 (s, 3H), 1.68 (s, 3H).<br>$^{13}$C NMR (101 MHz, CDCl$_3$) δ 195.13, 149.16, 147.77, 142.29, 141.38, 137.15, 130.66, 128.50, 126.29, 126.02, 114.47, 52.32, 46.22, 27.49, 24.64, 12.84.<br>HR-MS (ESI) calcd. for (C$_{18}$H$_{18}$O$_3$ + Na)$^+$ 305.1148, found: 305.1147. |
| I-24 | $^1$H NMR (400 MHz, CDCl$_3$) δ 12.33 (s, 1H), 9.77 (s, 1H), 7.43-7.28 (m, 6H), 7.24-7.19 (m, 3H), 7.11 (d, J = 6.5 Hz, 4H), 7.03 (d, J = 7.6 Hz, 2H), 5.93 (t, J = 6.7 Hz, 1H), 5.79 (s, 1H), 3.45 (d, J = 6.7 Hz, 2H), 1.95 (s, 3H).<br>$^{13}$C NMR (101 MHz, CDCl$_3$) δ 196.87, 149.25, 142.15, 141.44, 141.20, 139.28, 139.16, 134.68, 132.79, 132.07, 129.93, 128.93, 128.80, 128.51, 128.26, 127.64, 127.62, 127.40, 127.36, 116.00, 29.39, 14.82.<br>HR-MS (ESI) calcd. for (C$_{29}$H$_{24}$O$_3$ + Na)$^+$ 443.1618, found: 443.1611. |

| Structure and number | Characterization data ¹HNMR, ¹³CNMR, Mass |
|---|---|
| I-25 | I-25 ¹H NMR (400 MHz, CDCl$_3$) δ 12.25 (s, 1H), 10.25 (s, 1H), 7.43-7.36 (m, 3H), 7.31-7.24 (m, 3H), 7.22-7.17 (m, 2H), 7.13 (dd, J = 7.5, 1.7 Hz, 2H), 5.91 (s, 1H), 4.39 (s, 2H), 4.33 (s, 2H), 1.98 (s, 3H).<br>¹³C NMR (101 MHz, CDCl$_3$) δ 197.14, 149.13, 142.94, 138.53, 137.74, 135.64, 131.00, 130.05, 128.89, 128.55, 128.46, 128.01, 127.95, 127.51, 116.27, 72.74, 65.72, 14.61.<br>HR-MS (ESI) calcd. for (C$_{22}$H$_{20}$O$_4$ + Na)$^+$ 371.1254, found: 371.1253. |
| I-26 | I-26 ¹H NMR (400 MHz, CDCl$_3$) δ 12.25 (s, 1H), 10.23 (s, 1H), 7.33-7.26 (m, 3H), 7.22-7.17 (m, 2H), 7.11-7.04 (m, 4H), 5.94 (s, 1H), 4.35 (s, 2H), 4.35 (s, 2H), 1.97 (s, 3H).<br>¹³C NMR (101 MHz, CDCl$_3$) δ 197.01, 162.27 (d, J = 246.5 Hz), 149.23, 143.02, 137.55, 134.51, 134.32 (d, J = 3.6 Hz), 131.64 (d, J = 7.9 Hz), 131.05, 129.06, 128.58, 128.08, 128.06, 116.30, 115.42 (d, J = 21.3 Hz), 72.88, 65.44, 14.58.<br>¹⁹F NMR (376 MHz, CDCl$_3$) δ −114.83.<br>HR-MS (ESI) calcd. for (C$_{22}$H$_{19}$FO$_4$ + Na)$^+$ 389.1160, found: 389.1155. |
| I-27 | I-27 ¹H NMR (400 MHz, CDCl$_3$) δ 12.28 (s, 1H), 10.23 (s, 1H), 8.20 (d, J = 8.6 Hz, 2H), 7.32-7.26 (m, 5H), 7.22-7.15 (m, 2H), 6.04 (bro, 1H), 4.37 (s, 2H), 4.27 (s, 2H), 1.95 (s, 3H).<br>¹³C NMR (101 MHz, CDCl$_3$) δ 196.73, 149.64, 147.37, 145.56, 143.34, 137.12, 133.22, 131.09, 129.96, 128.61, 128.40, 128.30, 128.25, 123.62, 116.41, 73.05, 64.89, 14.53.<br>HR-MS (ESI) calcd. for (C$_{22}$H$_{19}$NO$_6$ + Na)$^+$ 416.1105, found: 416.1100. |
| I-28 | I-28 ¹H NMR (400 MHz, CDCl$_3$) δ 12.32 (s, 1H), 10.25 (s, 1H), 7.73 (d, J = 7.6 Hz, 1H), 7.60 (t, J = 7.4 Hz, 1H), 7.47 (t, J = 7.5 Hz, 1H), 7.27 (dd, J = 10.4, 4.9 Hz, 4H), 7.20-7.15 (m, 2H), 6.03 (s, 1H), 4.52 (d, J = 11.3 Hz, 1H), 4.34 (q, J = 11.8 Hz, 2H), 4.11 (d, J = 11.3 Hz, 1H), 1.96 (s, 3H).<br>¹³C NMR (101 MHz, CDCl$_3$) δ 196.79, 150.03, 143.41, 142.60, 137.40, 132.90, 132.80, 131.31, 131.28, 130.37, 129.19, 128.54, 128.34, 127.99, 117.53, 116.49, 114.18, 72.76, 65.24, 14.14.<br>HR-MS (ESI) calcd. for (C$_{23}$H$_{19}$NO$_4$ + Na)$^+$ 396.1206, found: 396.1211. |
| I-29 | I-29 ¹H NMR (400 MHz, CDCl$_3$) δ 12.27 (s, 1H), 10.27 (s, 1H), 7.35-7.28 (m, 3H), 7.26-7.21 (m, 2H), 7.09-7.05 (m, 2H), 6.98-6.93 (m, 2H), 5.92 (s, 1H), 4.44 (s, 2H), 4.38 (s, 2H), 3.90 (s, 3H), 2.02 (s, 3H).<br>¹³C NMR (101 MHz, CDCl$_3$) δ 197.17, 158.96, 149.04, 142.89, 137.78, 135.33, 131.45, 131.11, 130.66, 129.25, 128.54, 128.06, 127.94, 116.26, 113.85, 72.75, 65.73, 55.43, 14.66.<br>HR-MS (ESI) calcd. for (C$_{23}$H$_{22}$O$_5$ + Na)$^+$ 401.1359, found: 401.1360. |
| I-30 | I-30 ¹H NMR (400 MHz, CDCl$_3$) δ 12.27 (s, 1H), 10.28 (s, 1H), 7.40-7.35 (m, 1H), 7.30-7.23 (m, 3H), 7.20-7.15 (m, 2H), 7.07-6.94 (m, 3H), 5.89 (s, 1H), 4.54 (d, J = 11.3 Hz, 1H), 4.31 (s, 2H), 4.30 (d, J = 11.3 Hz, 1H), 3.71 (s, 3H), 1.95 (s, 3H).<br>¹³C NMR (101 MHz, CDCl$_3$) δ 197.20, 157.15, 149.26, 142.86, 137.96, 131.86, 131.71, 129.41, 128.48, 127.88, 127.81, 126.98, 120.73, 116.41, 110.82, 72.43, 66.09, 55.51, 14.08.<br>HR-MS (ESI) calcd. for (C$_{23}$H$_{22}$O$_5$ + Na)$^+$ 401.1359, found: 401.1360. |

| Structure and number | Characterization data ¹HNMR, ¹³CNMR, Mass |
|---|---|
| I-31 | I-31 ¹H NMR (400 MHz, CDCl$_3$) δ 12.12 (s, 1H), 10.24 (s, 1H), 7.42-7.26 (m, 5H), 6.66 (s, 1H), 5.82 (s, 1H), 4.68 (s, 2H), 4.54 (s, 2H), 2.69 (q, J = 7.5 Hz, 2H), 1.22 (t, J = 7.5 Hz, 3H).<br>¹³C NMR (101 MHz, CDCl$_3$) δ 196.25, 150.12, 142.80, 137.66, 137.46, 131.16, 128.65, 128.11, 128.07, 122.25, 116.37, 72.38, 69.55, 23.50, 13.59.<br>HR-MS (ESI) calcd. for (C$_{17}$H$_{18}$O$_4$ + Na)$^+$ 309.1097, found: 309.1100. |
| 32 | 32 ¹H NMR (400 MHz, CDCl$_3$) δ 12.31 (s, 1H), 10.25 (s, 1H), 7.39 (dd, J = 5.2,1.1 Hz, 1H), 7.34-7.26 (m, 3H), 7.25-7.21 (m, 2H), 7.08 (dd, J = 5.2, 3.4 Hz, 1H), 6.85 (dd, J = 3.4, 1.1 Hz, 1H), 5.88 (s, 1H), 4.51 (s, 2H), 4.40 (s, 2H), 2.09 (s, 3H).<br>¹³C NMR (101 MHz, CDCl$_3$) δ 197.09, 149.90, 142.95, 138.71, 137.73, 132.71, 131.47, 128.58, 128.46, 128.08, 127.99, 127.34, 127.16, 126.43, 116.32, 72.82, 65.74, 14.49.<br>HR-MS (ESI) calcd. for (C$_{23}$H$_{22}$O$_4$ + Na)$^+$ 385.1410, found: 385.1413. |
| I-33 | I-33 ¹H NMR (400 MHz, CDCl$_3$) δ 12.34 (s, 1H), 10.31 (s, 1H), 7.70 (dd, J = 8.0,1.0 Hz, 1H), 7.38 (td, J = 7.4, 1.1 Hz, 1H), 7.34-7.26 (m, 4H), 7.21 (td, J = 7.8, 1.7 Hz, 3H), 6.01 (s, 1H), 4.56 (d, J = 11.3 Hz, 1H), 4.37 (s, 2H), 4.19 (d, J = 11.3 Hz, 1H), 1.98 (s, 3H).<br>¹³C NMR (101 MHz, CDCl$_3$) δ 197.02, 149.57, 143.11, 139.29, 137.65, 134.25, 132.80, 131.80, 130.87, 129.46, 128.94, 128.51, 127.95, 127.91, 127.59, 125.04, 116.37, 72.87, 65.72, 14.00.<br>HR-MS (ESI) calcd. for (C$_{22}$H$_{19}$BrO$_4$ + Na)$^+$ 449.0359, found: 449.0363. |
| I-34 | I-34 ¹H NMR (400 MHz, CDCl$_3$) δ 12.25 (s, 1H), 10.22 (s, 1H), 7.50 (d, J = 8.3 Hz, 2H), 7.34-7.27 (m, 3H), 7.24-7.15 (m, 2H), 6.99 (d, J = 8.3 Hz, 2H), 5.95 (s, 1H), 4.36 (s, 2H), 4.34 (s, 2H), 1.96 (s, 3H).<br>¹³C NMR (101 MHz, CDCl$_3$) δ 196.95, 149.29, 143.07, 137.45, 137.37, 134.27, 131.73, 131.65, 130.69, 128.77, 128.60, 128.13, 128.09, 121.76, 116.32, 72.90, 65.31, 14.58.<br>HR-MS (ESI) calcd. for (C$_{22}$H$_{19}$BrO$_4$ + Na)$^+$ 449.0359, found: 449.0362. |
| I-35 | I-35 ¹H NMR (400 MHz, CDCl$_3$) δ 12.24 (s, 1H), 10.25 (s, 1H), 7.31-7.22 (m, 6H), 7.20-7.14 (m, 2H), 7.01 (d, J = 7.3 Hz, 1H), 5.90 (s, 1H), 4.41 (d, J = 10.9 Hz, 1H), 4.31 (q, J = 11.7 Hz, 2H), 4.25 (d, J = 10.9 Hz, 1H), 1.97 (s, 3H), 1.91 (s, 3H).<br>¹³C NMR (101 MHz, CDCl$_3$) δ 197.15, 149.07, 143.11, 138.00, 137.71, 136.90, 134.59, 130.89, 130.13, 130.05, 128.78, 128.53, 127.97, 127.92, 126.04, 116.47, 72.97, 65.80, 19.91, 14.03.<br>HR-MS (ESI) calcd. for (C$_{23}$H$_{22}$O$_4$ + Na)$^+$ 385.1410, found: 385.1412. |
| I-36 | I-36 ¹H NMR (400 MHz, CDCl$_3$) δ 12.24 (s, 1H), 10.25 (s, 1H), 7.32-7.24 (m, 4H), 7.22-7.16 (m, 3H), 6.98-6.90 (m, 2H), 5.90 (s, 1H), 4.40 (s, 2H), 4.34 (s, 2H), 2.38 (s, 3H), 1.99 (s, 3H).<br>¹³C NMR (101 MHz, CDCl$_3$) δ 197.16, 149.05, 142.89, 138.43, 138.05, 137.80, 135.80, 131.05, 130.71, 128.87, 128.53, 128.32, 128.22, 127.96, 127.92, 127.09, 116.24, 72.69, 65.82, 21.61, 14.63.<br>HR-MS (ESI) calcd. for (C$_{23}$H$_{22}$O$_4$ + Na)$^+$ 385.1410, found: 385.1413. |

| Structure and number | Characterization data ¹HNMR, ¹³CNMR, Mass |
|---|---|
| I-37 | I-37 ¹H NMR (400 MHz, CDCl₃) δ 12.24 (s, 1H), 10.25 (s, 1H), 7.32-7.25 (m, 3H), 7.23-7.16 (m, 4H), 7.01 (d, J = 8.0 Hz, 2H), 5.87 (s, 1H), 4.40 (s, 2H), 4.34 (s, 2H), 2.42 (s, 3H), 1.98 (s, 3H). ¹³C NMR (101 MHz, CDCl₃) δ 197.19, 149.05, 142.89, 137.79, 137.10, 135.66, 135.44, 131.18, 129.90, 129.16, 129.03, 128.53, 128.05, 127.90, 116.27, 72.69, 65.74, 21.39, 14.63. HR-MS (ESI) calcd. for (C$_{23}$H$_{22}$O$_4$ + Na)$^+$ 385.1410, found: 385.1415. |
| I-38 | I-38 ¹H NMR (400 MHz, CDCl₃) δ 11.49 (s, 1H), 10.10 (s, 1H), 7.25 (dd, J = 8.2, 6.5 Hz, 2H), 7.17 (t, J = 7.3 Hz, 1H), 7.01 (d, J = 7.1 Hz, 2H), 5.57 (s, 1H), 4.42 (dd, J = 9.0, 2.5 Hz, 1H), 3.33-3.08 (m, 2H), 2.65 (dq, J = 12.9, 9.1 Hz, 1H), 2.51 (tt, J = 15.0, 7.5 Hz, 1H), 2.41-2.22 (m, 1H), 2.18-2.00 (m, 1H), 0.84 (t, J = 7.5 Hz, 3H). ¹³C NMR (101 MHz, CDCl₃) δ 195.10, 148.38, 145.88, 141.86, 138.01, 136.75, 136.56, 128.69, 127.36, 126.43, 114.67, 49.34, 35.88, 28.38, 21.55, 12.64. HR-MS (ESI) calcd. for (C$_{18}$H$_{18}$O$_3$ + H)$^+$ 283.1329, found: 283.1333. |
| I-39 | I-39 ¹H NMR (400 MHz, CDCl₃) δ 12.16 (s, 1H), 10.18 (s, 1H), 7.42-7.29 (m, 5H), 5.82 (s, 1H), 4.73 (s, 2H), 4.59 (s, 2H), 2.25 (s, 3H), 2.19 (s, 3H). ¹³C NMR (101 MHz, CDCl₃) δ 196.62, 148.00, 142.90, 137.82, 131.72, 128.79, 128.70, 128.18, 128.15, 116.53, 72.74, 63.88, 14.77, 13.34. HR-MS (ESI) calcd. for (C$_{17}$H$_{18}$O$_4$ + Na)$^+$ 309.1097, found: 309.1096. |
| I-40 | I-40 ¹H NMR (400 MHz, CDCl₃) δ 12.39 (s, 1H), 10.27 (s, 1H), 7.01 (t, J = 8.7 Hz, 2H), 6.95 (dd, J = 8.4, 5.8 Hz, 2H), 5.95 (s, 2H), 5.75 (s, 1H), 3.89 (s, 2H), 3.75 (s, 3H), 3.52 (s, 6H), 1.89 (s, 3H). ¹³C NMR (101 MHz, CDCl₃) δ 197.88, 163.17, 160.74, 159.96, 158.53, 148.62, 140.64, 135.80, 135.76, 135.00, 133.94, 132.09, 132.01, 131.15, 116.54, 115.05, 114.83, 110.69, 90.56, 55.39, 22.87, 14.62. ¹⁹F NMR (376 MHz, CDCl₃) δ −116.47. HR-MS (ESI) calcd. for (C$_{24}$H$_{23}$FO$_6$ + Na)$^+$ 449.1371, found: 449.1374. |
| I-41 | I-41 ¹H NMR (400 MHz, CDCl₃) δ 12.41 (s, 1H), 10.33 (s, 1H), 7.43 (d, J = 8.2 Hz, 2H), 6.84 (d, J = 8.2 Hz, 2H), 5.93 (s, 2H), 5.74 (s, 1H), 3.89 (s, 2H), 3.75 (s, 3H), 3.51 (s, 6H), 1.88 (s, 3H). ¹³C NMR (101 MHz, CDCl₃) δ 197.81, 159.99, 158.57, 148.66, 140.68, 138.83, 134.65, 133.71, 132.25, 131.21, 130.79, 120.96, 116.59, 110.28, 90.43, 55.41, 22.61, 14.59. HR-MS (ESI) calcd. for (C$_{24}$H$_{23}$BrO$_6$ + Na)$^+$ 509.0570, found: 509.0563. |

| Structure and number | Characterization data ¹HNMR, ¹³CNMR, Mass |
|---|---|
| I-42 | I-42 ¹H NMR (400 MHz, CDCl₃) δ 12.45 (s, 1H), 10.35 (s, 1H), 8.17 (d, J = 8.6 Hz, 2H), 7.16 (d, J = 8.6 Hz, 2H), 5.92 (s, 2H), 5.84 (s, 1H), 3.87 (s, 2H), 3.75 (s, 3H), 3.48 (s, 6H), 1.87 (s, 3H). ¹³C NMR (101 MHz, CDCl₃) δ 197.60, 160.20, 158.50, 149.05, 147.33, 147.03, 140.91, 134.23, 132.61, 131.61, 129.96, 123.21, 116.63, 109.72, 90.46, 55.41, 55.27, 22.58, 14.50. HR-MS (ESI) calcd. for (C₂₄H₂₃NO₈ + Na)⁺ 476.1316, found: 476.1308. |
| I-43 | I-43 ¹H NMR (400 MHz, CDCl₃) δ 12.49 (s, 1H), 10.39 (s, 1H), 7.63 (d, J = 7.7 Hz, 1H), 7.52 (t, J = 7.6 Hz, 1H), 7.39 (t, J = 7.6 Hz, 1H), 7.12 (d, J = 7.7 Hz, 1H), 5.91 (s, 2H), 5.76 (s, 1H), 4.10 (d, J = 16.0 Hz, 1H), 3.75 (s, 2H), 3.74 (d, J = 16.0 Hz, 2H), 3.48 (s, 6H), 1.86 (s, 3H). ¹³C NMR (101 MHz, CDCl₃) δ 197.58, 160.19, 158.62, 149.45, 143.87, 141.04, 135.03, 132.46, 132.20, 131.80, 130.64, 130.56, 127.43, 117.74, 116.78, 114.57, 109.44, 90.52, 55.46, 55.36, 22.38, 14.09. HR-MS (ESI) calcd. for (C₂₅H₂₃NO₆ + Na)⁺ 456.1418, found: 456.1418. |
| I-44 | I-44 ¹H NMR (400 MHz, CDCl₃) δ 12.30 (s, 1H), 10.17 (s, 1H), 7.36-7.27 (m, 3H), 7.08 (d, J = 6.9 Hz, 2H), 5.96 (s, 2H), 5.67 (s, 1H), 3.87 (s, 2H), 3.74 (s, 3H), 3.53 (s, 6H), 2.35 (q, J = 7.4 Hz, 2H), 0.95 (t, J = 7.4 Hz, 3H). ¹³C NMR (101 MHz, CDCl₃) δ 197.95, 159.89, 158.44, 148.61, 140.32, 139.68, 137.09, 135.38, 134.47, 130.70, 127.83, 126.77, 116.52, 111.48, 90.73, 55.47, 55.39, 23.42, 21.92, 13.78. HR-MS (ESI) calcd. for (C₂₅H₂₆O₆ + Na)⁺ 445.1622, found: 445.1619. |
| I-45 | I-45 ¹H NMR (400 MHz, CDCl₃) δ 12.24 (s, 1H), 10.25 (s, 1H), 7.32-7.23 (m, 3H), 7.22-7.17 (m, 2H), 7.00 (s, 1H), 6.75 (s, 2H), 5.91 (s, 1H), 4.41 (s, 2H), 4.34 (s, 2H), 2.34 (s, 7H), 1.99 (s, 3H). ¹³C NMR (101 MHz, CDCl₃) δ 197.17, 148.96, 142.83, 138.33, 137.85, 135.94, 131.08, 129.04, 128.83, 128.50, 127.91, 127.89, 127.78, 116.21, 72.62, 65.90, 21.48, 14.64. HR-MS (ESI) calcd. for (C₂₄H₂₄O₄ + Na)⁺ 399.1567, found: 399.1572. |

| Structure and number | Characterization data $^1$HNMR, $^{13}$CNMR, Mass |
|---|---|
| I-46 | $^1$H NMR (400 MHz, CDCl$_3$) δ 12.26 (s, 1H), 10.26 (s, 1H), 7.38 (d, J = 8.3 Hz, 2H), 7.30-7.23 (m, 3H), 7.22-7.16 (m, 2H), 7.04 (d, J = 8.3 Hz, 2H), 5.91 (s, 1H), 4.40 (s, 2H), 4.35 (s, 2H), 1.99 (s, 3H), 1.37 (s, 9H).<br>$^{13}$C NMR (101 MHz, CDCl$_3$) δ 197.24, 150.31, 149.06, 142.87, 137.81, 135.63, 135.31, 131.27, 129.65, 129.05, 128.51, 128.02, 127.91, 125.24, 116.25, 72.57, 65.71, 34.73, 31.56, 14.72.<br>HR-MS (ESI) calcd. for (C$_{26}$H$_{28}$O$_4$ + Na)$^+$ 427.1880, found: 427.1882. |
| I-47 | $^1$H NMR (400 MHz, CDCl$_3$) δ 12.34 (s, 1H), 10.29 (s, 1H), 7.91 (dd, J = 12.1, 8.3 Hz, 2H), 7.50 (ddd, J = 8.3, 6.3, 2.1 Hz, 2H), 7.41-7.34 (m, 2H), 7.26 (dd, J = 7.0, 1.0 Hz, 1H), 7.19 (dd, J = 6.6, 3.6 Hz, 3H), 7.04-6.96 (m, 2H), 5.95 (s, 1H), 4.34 (d, J = 11.1 Hz, 1H), 4.19-4.11 (m, 3H), 1.84 (s, 3H).<br>$^{13}$C NMR (101 MHz, CDCl$_3$) δ 197.23, 149.41, 143.07, 137.60, 135.98, 133.71, 133.12, 132.76, 131.82, 130.00, 128.50, 128.42, 128.20, 127.86, 127.83, 127.81, 126.56, 126.23, 125.78, 125.49, 116.53, 72.73, 65.95, 14.19.<br>HR-MS (ESI) calcd. for (C$_{26}$H$_{22}$O$_4$ + Na)$^+$ 421.1410, found: 421.1416. |
| I-48 | $^1$H NMR (400 MHz, CDCl$_3$) δ 12.28 (s, 1H), 10.26 (s, 1H), 7.42 (dd, J = 4.9, 3.0 Hz, 1H), 7.37-7.29 (m, 3H), 7.28-7.22 (m, 2H), 7.09 (dd, J = 3.0, 1.2 Hz, 1H), 6.94 (dd, J = 4.9, 1.2 Hz, 1H), 5.88 (s, 1H), 4.41 (s, 3H), 2.06 (s, 3H).<br>$^{13}$C NMR (101 MHz, CDCl$_3$) δ 197.03, 149.28, 143.00, 138.20, 137.72, 131.71, 130.43, 129.80, 129.57, 128.61, 128.08, 128.03, 125.68, 124.07, 116.34, 72.84, 65.68, 14.49. HR-MS (ESI) calcd. for (C$_{20}$H$_{18}$O$_4$S + Na)$^+$ 377.0818, found:377.0814. |
| I-49 | $^1$H NMR (400 MHz, CDCl$_3$) δ 12.40 (s, 1H), 10.27 (s, 1H), 8.00 (d, J = 8.3 Hz, 2H), 7.10 (d, J = 8.3 Hz, 2H), 5.93 (s, 2H), 5.78 (s, 1H), 3.94 (s, 3H), 3.88 (s, 2H), 3.75 (s, 3H), 3.49 (s, 6H), 1.88 (s, 3H).<br>$^{13}$C NMR (101 MHz, CDCl$_3$) δ 197.83, 167.28, 160.04, 158.48, 148.77, 145.20, 140.76, 134.45, 133.97, 130.70, 130.44, 129.37, 128.71, 116.58, 110.54, 90.58, 55.35, 52.23, 22.93, 14.54.<br>HR-MS (ESI) calcd. for (C$_{26}$H$_{26}$O$_8$ + Na)$^+$ 489.1520, found: 489.1521. |
| I-50 | $^1$H NMR (400 MHz, CDCl$_3$) δ 11.50 (s, 1H), 10.09 (s, 1H), 7.27-7.24 (m, 2H), 7.20-7.14 (m, 1H), 7.01-6.94 (m, 2H), 5.59 (s, 1H), 4.46 (dd, J = 9.1, 1.9 Hz, 1H), 3.24-3.12 (m, 2H), 2.83 (dt, J = 14.0, 7.0 Hz, 1H), 2.63 (dq, J = 12.8, 9.3 Hz, 1H), 2.15-2.05 (m, 1H), 1.28 (d, J = 7.0 Hz, 3H), 0.90 (d, J = 7.0 Hz, 3H).<br>$^{13}$C NMR (101 MHz, CDCl$_3$) δ 195.08, 148.88, 145.98, 142.77, 139.61, 137.74, 136.27, 128.60, 127.30, 126.34, 114.56, 49.70, 35.57, 31.36, 28.31, 20.06, 19.06.<br>HR-MS (ESI) calcd. for (C$_{19}$H$_{20}$O$_3$ + Na)$^+$ 319.1305, found: 319.1302. |

| Structure and number | Characterization data ¹HNMR, ¹³CNMR, Mass |
|---|---|
| I-51 | ¹H NMR (400 MHz, CDCl$_3$) δ 12.24 (s, 1H), 10.51 (s, 1H), 6.76 (s, 1H), 6.12 (s, 2H), 5.62 (s, 1H), 4.11 (s, 2H), 3.79 (s, 3H), 3.78 (s, 6H), 3.27 (hept, J = 6.9 Hz, 1H), 1.18 (d, J = 6.9 Hz, 6H). <br> ¹³C NMR (101 MHz, CDCl$_3$) δ 197.26, 160.12, 158.63, 149.11, 142.08, 139.77, 136.50, 119.06, 116.23, 109.63, 90.82, 55.61, 55.44, 27.73, 23.83, 22.05. <br> HR-MS (ESI) calcd. for (C$_{20}$H$_{24}$O$_6$ + Na)$^+$ 383.1465, found: 383.1463. |
| I-52 | ¹H NMR (400 MHz, CDCl$_3$) δ 12.23 (s, 1H), 10.52 (s, 1H), 6.60 (s, 1H), 6.13 (s, 2H), 5.51 (s, 1H), 4.12 (s, 2H), 3.80 (s, 3H), 3.78 (s, 6H), 2.60 (q, J = 7.5 Hz, 2H), 1.16 (t, J = 7.6 Hz, 3H). <br> ¹³C NMR (101 MHz, CDCl$_3$) δ 197.04, 160.17, 158.75, 149.16, 140.30, 138.10, 136.46, 121.45, 116.38, 109.43, 90.87, 55.69, 23.64, 23.49, 13.62. <br> HR-MS (ESI) calcd. for (C$_{19}$H$_{22}$O$_6$ + Na)$^+$ 369.1309, found: 369.1305. |
| I-53 | ¹H NMR (400 MHz, CDCl$_3$) δ 12.18 (s, 1H), 10.28 (s, 1H), 7.44-7.31 (m, 5H), 6.74 (s, 1H), 5.90 (s, 1H), 4.73 (s, 2H), 4.59 (s, 2H), 3.40 (hept, J = 6.9 Hz, 1H), 1.28 (d, J = 6.9 Hz, 6H). <br> ¹³C NMR (101 MHz, CDCl$_3$) δ 196.24, 150.11, 142.28, 141.56, 137.65, 131.20, 128.64, 128.15, 128.07, 119.40, 116.21, 72.38, 69.73, 27.70, 21.99. <br> HR-MS (ESI) calcd. for (C$_{18}$H$_{20}$O$_4$ + Na)$^+$ 323.1254, found: 323.1251. |
| I-54 | ¹H NMR (400 MHz, DMSO) δ 10.37 (s, 1H), 10.20 (s, 1H), 8.82 (s, 1H), 7.58 (d, J = 5.0 Hz, 1H), 7.41 (d, J = 5.0 Hz, 1H), 4.06 (s, 2H), 2.49 (s, 3H). <br> ¹³C NMR (101 MHz, DMSO) δ 192.85, 147.35, 145.65, 142.58, 142.43, 138.74, 130.77, 128.88, 125.39, 120.00, 117.43, 33.55, 13.35. <br> HR-MS (ESI) calcd. for (C$_{13}$H$_{10}$O$_3$S + Na)$^+$ 269.0243, found: 269.0237. |
| I-55 | ¹H NMR (400 MHz, CDCl$_3$) δ 12.23 (s, 1H), 10.22 (s, 1H), 7.42-7.36 (m, 3H), 7.32-7.26 (m, 3H), 7.21-7.16 (m, 2H), 7.16-7.11 (m, 2H), 5.93 (s, 1H), 4.31 (s, 2H), 4.30 (s, 2H), 2.73-2.59 (m, 1H), 1.23 (s, 3H), 1.22 (s, 3H). <br> ¹³C NMR (101 MHz, CDCl$_3$) δ 197.07, 149.64, 143.88, 139.83, 139.13, 137.71, 134.85, 129.84, 128.96, 128.55, 128.33, 128.04, 127.96, 127.43, 116.16, 72.86, 65.86, 31.36, 19.81. |
| I-A1 | ¹H NMR (400 MHz, CDCl$_3$) δ 13.15 (s, 1H), 7.26-7.22 (m, 2H), 7.18 (t, J = 7.1 Hz, 1H), 7.00 (d, J = 7.4 Hz, 2H), 6.16 (s, 1H), 4.60 (dd, J = 9.1, 2.8 Hz, 1H), 4.55 (d, J = 11.0 Hz, 1H), 4.14 (d, J = 11.0 Hz, 1H), 3.98 (qd, J = 15.7, 2.2 Hz, 2H), 3.27 (dt, J = 16.4, 8.3 Hz, 1H), 3.15 (ddd, J = 16.0, 9.0, 3.2 Hz, 1H), 2.69 (s, 3H), 2.66-2.57 (m, 1H), 2.40 (s, 1H), 2.06 (ddd, J = 11.6, 7.1, 3.0 Hz, 1H). <br> ¹³C NMR (101 MHz, CDCl$_3$) δ 205.75, 150.51, 145.69, 143.87, 137.05, 135.40, 128.68, 127.36, 126.43, 124.96, 117.33, 79.68, 74.75, 63.94, 57.83, 49.04, 35.74, 34.28, 32.20. <br> HR-MS (ESI) calcd. for (C$_{21}$H$_{20}$O$_4$ + Na)$^+$ 359.1254, found: 359.1260. |
| I-A2 | ¹H NMR (400 MHz, CDCl$_3$) δ 12.29 (s, 1H), 10.32 (s, 1H), 7.49-7.35 (m, 3H), 7.15 (d, J = 6.7 Hz, 2H), 5.97 (s, 1H), 4.45 (s, 2H), 4.00 (s, 2H), 2.34 (s, 1H), 1.98 (s, 3H). <br> ¹³C NMR (101 MHz, CDCl$_3$) δ 197.21, 149.13, 143.10, 138.37, 135.83, 131.01, 130.06, 128.50, 128.06, 127.54, 116.15, 79.13, 75.13, 65.13, 57.61, 14.62. <br> HR-MS (ESI) calcd. for (C$_{18}$H$_{16}$O$_4$ + Na)$^+$ 319.0941, found: 319.0942. |

| Structure and number | Characterization data ¹HNMR, ¹³CNMR, Mass |
|---|---|
| 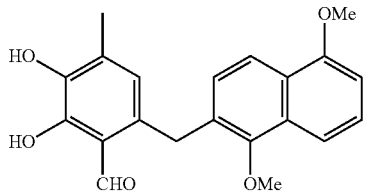 | I-A3 $^1$H NMR (400 MHz, CDCl$_3$) δ 12.31 (s, 1H), 10.59 (s, 1H), 7.78 (d, J = 8.9 Hz, 1H), 7.73 (d, J = 8.9 Hz, 1H), 7.19 (d, J = 9.0 Hz, 1H), 7.09 (s, 1H), 7.03 (dd, J = 8.9, 2.2 Hz, 1H), 6.26 (s, 1H), 5.58 (s, 1H), 4.66 (s, 1H), 3.95 (s, 1H), 3.81 (s, 1H), 2.12 (s, 1H).<br>$^{13}$C NMR (101 MHz, CDCl$_3$) δ 195.84, 158.56, 155.36, 149.84, 141.17, 134.92, 134.87, 132.68, 130.30, 128.81, 124.93, 122.13, 119.14, 116.49, 116.10, 110.70, 102.38, 56.51, 55.35, 26.38, 16.47.<br>HR-MS (ESI) calcd. for (C$_{21}$H$_{20}$O$_5$ + Na)$^+$ 375.1203, found: 375.1208. |
| 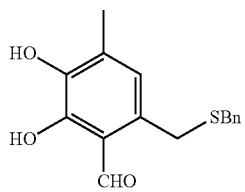 | I-A4 $^1$H NMR (400 MHz, CDCl$_3$) δ 12.11 (s, 1H), 10.12 (s, 1H), 7.34-7.27 (m, 5H), 6.47 (s, 1H), 5.71 (s, 1H), 3.75 (s, 2H), 3.69 (s, 2H), 2.25 (s, 3H).<br>$^{13}$C NMR (101 MHz, CDCl$_3$) δ 195.05, 150.20, 142.60, 137.77, 131.87, 131.08, 129.02, 128.73, 127.38, 124.05, 115.56, 36.71, 31.82, 16.24.<br>HR-MS (ESI) calcd. for (C$_{16}$H$_{16}$O$_3$S + Na)$^+$ 311.0712, found: 311.0711. |
| 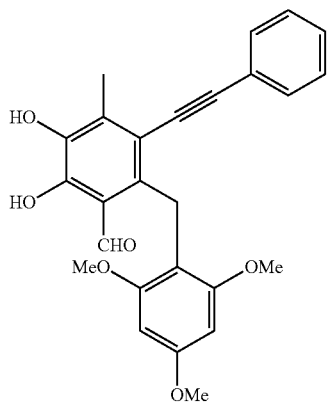 [SMILES: COc1cc(OC)c(Cc2c(C#Cc3ccccc3)c(C)c(O)c(O)c2C=O)c(OC)c1] | I-A5 $^1$H NMR (400 MHz, CDCl$_3$) δ 12.46 (s, 1H), 10.20 (s, 1H), 7.55-7.45 (m, 2H), 7.37-7.28 (m, 3H), 6.07 (s, 2H), 5.64 (s, 1H), 4.49 (s, 2H), 3.77 (s, 3H), 3.67 (s, 6H), 2.52 (s, 3H).<br>$^{13}$C NMR (101 MHz, CDCl$_3$) δ 198.47, 160.17, 158.61, 149.57, 140.80, 140.04, 133.45, 131.42, 128.44, 128.04, 124.17, 117.39, 116.72, 111.20, 96.32, 91.02, 87.17, 55.74, 55.46, 24.63, 15.17.<br>HR-MS (ESI) calcd. for (C$_{26}$H$_{24}$O$_6$ + Na)$^+$ 455.1465, found: 455.1469. |
| 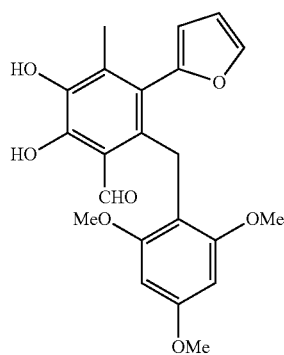 [SMILES: COc1cc(OC)c(Cc2c(C=O)c(O)c(O)c(C)c2-c2ccco2)c(OC)c1] | I-A6 $^1$H NMR (400 MHz, CDCl$_3$) δ 12.44 (s, 1H), 10.14 (s, 1H), 7.48 (s, 1H), 6.44 (s, 1H), 6.24 (d, J = 3.1 Hz, 1H), 6.01 (s, 2H), 5.64 (s, 1H), 4.04 (s, 2H), 3.75 (s, 3H), 3.63 (s, 6H), 2.04 (s, 3H).<br>$^{13}$C NMR (101 MHz, CDCl$_3$) δ 198.28, 160.03, 158.33, 151.61, 149.87, 141.82, 140.67, 138.39, 133.23, 124.89, 116.39, 111.51, 110.47, 110.40, 90.86, 55.56, 55.42, 23.42, 14.15.<br>HR-MS (ESI) calcd. for (C$_{22}$H$_{22}$O$_7$ + Na)$^+$ 421.1258, found: 421.1263. |
| 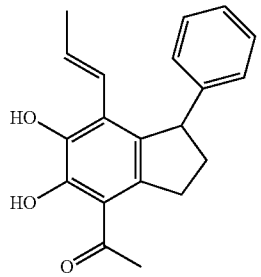 [SMILES: C/C=C/c1c(O)c(O)c(C(C)=O)c2c1C(c1ccccc1)CC2] | I-A7 $^1$H NMR (400 MHz, CDCl$_3$) δ 13.46 (s, 1H), 7.28-7.22 (m, 2H), 7.16 (dd, J = 8.4, 6.2 Hz, 1H), 6.97 (d, J = 7.1 Hz, 2H), 6.64 (dq, J = 15.9, 6.7 Hz, 1H), 6.20-6.06 (m, 2H), 4.50 (dd, J = 9.0, 1.8 Hz, 1H), 3.26-3.06 (m, 2H), 2.66 (s, 3H), 2.56 (dq, J = 12.6, 9.2 Hz, 1H), 2.08 (ddt, J = 12.4, 7.6, 2.3 Hz, 1H), 1.73 (dd, J = 6.7, 1.6 Hz, 3H).<br>$^{13}$C NMR (101 MHz, CDCl$_3$) δ 205.27, 150.45, 145.49, 142.19, 135.28, 135.17, 135.13, 128.64, 127.33, 126.42, 126.25, 124.88, 115.50, 49.49, 35.79, 34.11, 31.93, 20.00.<br>HR-MS (ESI) calcd. for (C$_{20}$H$_{20}$O$_3$ + Na)$^+$ 331.1305, found: 331.1309. |

| Structure and number | Characterization data ¹HNMR, ¹³CNMR, Mass |
|---|---|
| 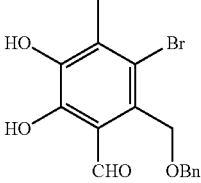 I-A8 | I-A8 ¹H NMR (400 MHz, CDCl$_3$) δ 12.22 (s, 1H), 10.22 (s, 1H), 7.41-7.27 (m, 5H), 5.98 (s, 1H), 5.00 (s, 2H), 4.60 (s, 2H), 2.42 (s, 3H).<br>¹³C NMR (101 MHz, CDCl$_3$) δ 196.57, 149.07, 144.00, 137.68, 132.24, 129.97, 128.65, 128.12, 119.47, 117.26, 72.71, 67.84, 17.52.<br>HR-MS (ESI) calcd. for (C$_{16}$H$_{15}$BrO$_4$ + Na)$^+$ 373.0046, found: 373.0040. |
| 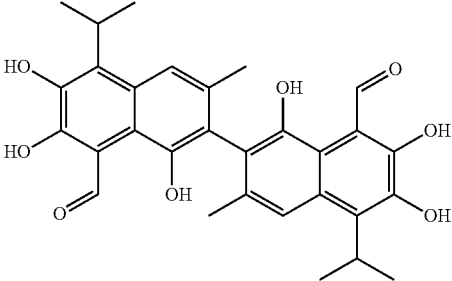 I-A9 | I-A9 ¹H NMR (400 MHz, CDCl$_3$) δ 15.16 (s, 1H), 11.13 (s, 1H), 7.79 (s, 1H), 6.43 (s, 1H), 5.84 (s, 1H), 4.00-3.77 (m, 1H), 2.16 (s, 3H), 1.56 (d, J = 6.9 Hz, 6H).<br>¹³C NMR (101 MHz, CDCl$_3$) δ 199.50, 156.25, 150.54, 143.62, 134.22, 133.82, 129.85, 118.29, 115.90, 114.78, 111.94, 27.99, 20.45, 20.37.<br>HR-MS (ESI) calcd. for (C$_{30}$H$_{30}$O$_8$ + H)$^+$ 519.2013, found: 519.2007. |
| 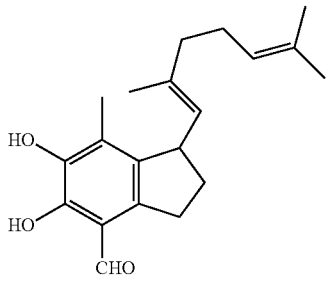 I-65 | I-65 ¹H NMR (400 MHz, CDCl$_3$) δ 11.39 (s, 1H), 10.03 (s, 1H), 5.51 (s, 1H), 5.10-5.02 (m, 2H), 3.96 (td, J = 9.2, 3.7 Hz, 1H), 3.20 (dt, J = 16.3, 8.2 Hz, 1H), 3.08 (ddd, J = 15.9, 9.1, 4.5 Hz, 1H), 2.38 (dq, J = 12.8, 8.5 Hz, 1H), 2.16 (s, 3H), 2.08 (dd, J = 14.3, 7.2 Hz, 2H), 2.00 (dd, J = 11.1, 4.5 Hz, 2H), 1.86 (ddd, J = 16.8, 8.4, 4.1 Hz, 1H), 1.77 (d, J = 1.0 Hz, 3H), 1.66 (s, 3H), 1.58 (s, 3H).<br>¹³C NMR (101 MHz, CDCl$_3$) δ 194.94, 147.49, 141.46, 138.03, 136.74, 134.08, 131.48, 130.42, 127.60, 124.14, 114.51, 42.50, 39.64, 33.10, 28.36, 26.50, 25.68, 17.69, 16.24, 12.65.<br>HR-MS (ESI) calcd. for (C$_{20}$H$_{26}$O$_3$ + Na)$^+$ 337.1774, found: 337.1779. |
| 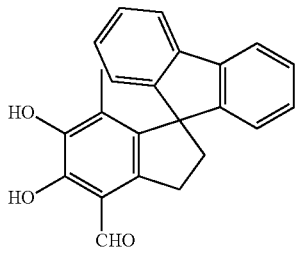 I-66 | I-66 ¹H NMR (400 MHz, CDCl$_3$) δ 11.57 (s, 1H), 10.21 (s, 1H), 7.77 (d, J = 7.5 Hz, 2H), 7.37 (t, J = 7.4 Hz, 2H), 7.24 (t, J = 7.4 Hz, 2H), 7.16 (d, J = 7.5 Hz, 2H), 5.50 (s, 1H), 3.52 (t, J = 7.3 Hz, 2H), 2.59 (t, J = 7.3 Hz, 2H), 1.17 (s, 2H).<br>¹³C NMR (101 MHz, CDCl$_3$) δ 194.94, 151.50, 148.55, 142.11, 140.03, 138.60, 137.32, 130.95, 127.89, 127.63, 123.68, 120.21, 114.67, 62.88, 41.32, 28.70, 10.97.<br>HR-MS (ESI) calcd. for (C$_{23}$H$_{18}$O$_3$ + H)$^+$ 343.1329, found: 343.1327. |
| 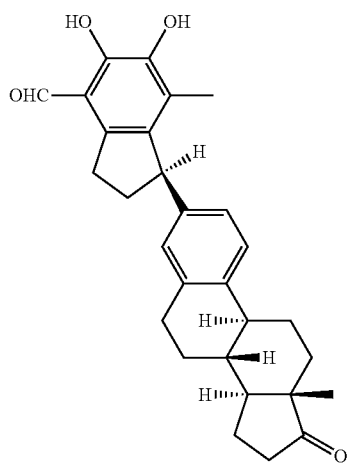 I-67 | I-67 ¹H NMR (400 MHz, CDCl$_3$) δ 11.50 (s, 1H), 10.09 (s, 1H), 7.15 (d, J = 7.8 Hz, 1H), 6.75 (d, J = 7.7 Hz, 1H), 6.74 (s, 1H), 5.59 (s, 1H), 4.32 (dd, J = 8.8, 2.4 Hz, 1H), 3.29-3.09 (m, 2H), 2.87-2.80 (m, 2H), 2.69-2.59 (m, 1H), 2.53-2.45 (m, 1H), 2.42-2.35 (m, 1H), 2.32-2.26 (m, 1H), 2.17-2.01 (m, 4H), 1.97 (s, 3H), 1.65-1.42 (m, 7H), 0.91 (s, 3H).<br>¹³C NMR (101 MHz, CDCl$_3$) δ 195.12, 148.09, 142.65, 141.85, 137.79, 137.20, 136.72, 130.72, 127.86, 125.62, 124.70, 114.59, 50.72, 49.16, 48.14, 44.46, 38.30, 35.99, 31.77, 29.61, 28.48, 26.70, 25.79, 21.73, 14.02, 13.51.<br>HR-MS (ESI) calcd. for (C$_{29}$H$_{32}$O$_4$ + H)$^+$ 445.2373, found: 445.2371. |

-continued

| Structure and number | Characterization data $^1$HNMR, $^{13}$CNMR, Mass |
|---|---|
| 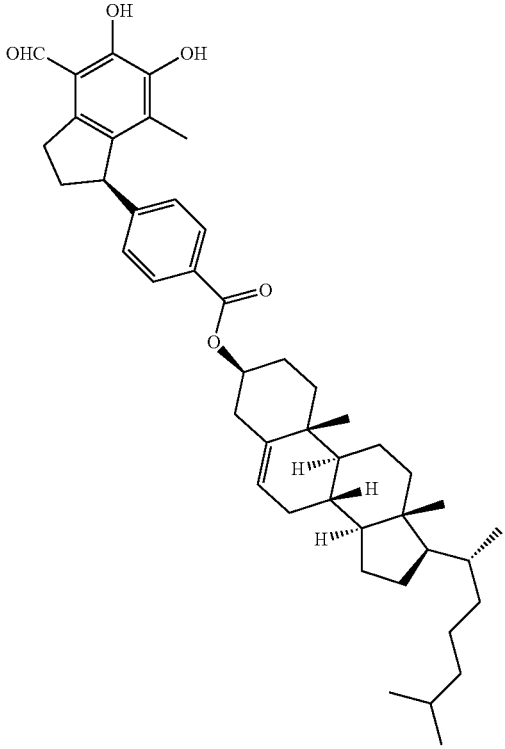<br>I-68 | I-68 $^1$H NMR (400 MHz, CDCl$_3$) δ 11.52 (s, 1H), 10.10 (s, 1H), 7.93 (d, J = 8.1 Hz, 2H), 7.07 (d, J = 8.1 Hz, 2H), 5.60 (s, 1H), 5.41 (d, J = 4.1 Hz, 1H), 4.88-4.79 (m, 1H), 4.43 (dd, J = 9.0, 3.1 Hz, 1H), 3.33-3.10 (m, 2H), 2.77-2.63 (m, 1H), 2.44 (d, J = 7.8 Hz, 2H), 2.10-1.95 (m, 4H), 1.92 (s, 3H), 1.87-1.80 (m, 1H), 1.77-1.65 (m, 2H), 1.60-1.44 (m, 6H), 1.33 (t, J = 9.3 Hz, 3H), 1.26 (t, J = 10.6 Hz, 2H), 1.22-1.08 (m, 6H), 1.06 (s, 3H), 1.04-0.96 (m, 3H), 0.92 (d, J = 6.4 Hz, 3H), 0.88 (s, 3H), 0.86 (s, 3H), 0.69 (s, 3H).<br>$^{13}$C NMR (101 MHz, CDCl$_3$) δ 195.01, 166.01, 150.62, 148.38, 142.12, 139.83, 137.70, 136.45, 130.44, 130.15, 129.21, 127.27, 122.92, 114.61, 74.66, 56.87, 56.32, 50.22, 49.74, 42.49, 39.91, 39.68, 38.39, 37.20, 36.81, 36.35, 35.95, 35.82, 32.09, 32.05, 28.54, 28.38, 28.16, 28.05, 24.45, 23.99, 22.96, 22.71, 21.21, 19.52, 18.88, 13.45, 12.02. |
| 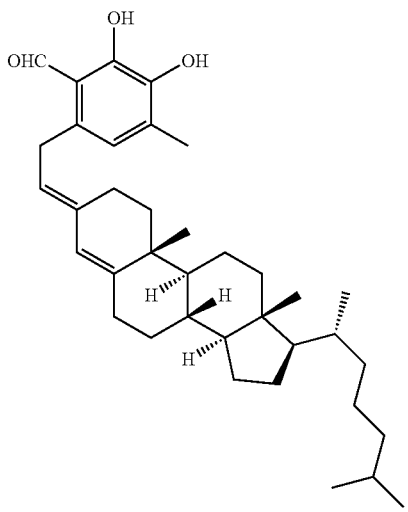<br>I-69 | I-69 $^1$H NMR (400 MHz, CDCl$_3$) δ 12.22 (s, 1H), 10.15 (s, 1H), 6.45 (s, 1H), 6.13 (s, 1H), 5.60 (s, 1H), 3.65 (dd, J = 46.3, 15.5 Hz, 2H), 2.26 (s, 3H), 2.20-2.08 (m, 1H), 2.02 (dd, J = 13.6, 9.6 Hz, 2H), 1.92-1.82 (m, 2H), 1.78 (s, 3H), 1.61-1.28 (m, 10H), 1.24-0.98 (m, 9H), 0.97-0.84 (m, 14H), 0.67 (s, 3H).<br>$^{13}$C NMR (101 MHz, CDCl$_3$) δ 195.86, 149.75, 141.12, 136.08, 136.00, 134.59, 132.37, 126.57, 122.82, 119.00, 116.69, 56.81, 56.08, 48.37, 42.33, 39.78, 39.52, 36.17, 36.13, 35.77, 35.33, 34.25, 33.77, 31.46, 28.20, 28.02, 27.92, 24.11, 23.97, 23.80, 22.80, 22.55, 21.15, 18.70, 18.64, 16.43, 11.98.<br>HR-MS (ESI) calcd. for (C$_{37}$H$_{54}$O$_3$ + Na)$^+$ 569.3965, found: 569.3971. |
| 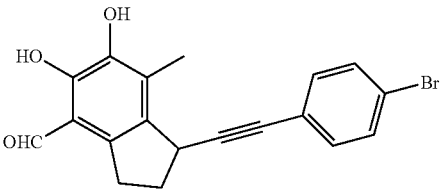 [SMILES: Cc1c(O)c(O)c(C=O)c2c1C(C#Cc1ccc(Br)cc1)CC2]<br>I-70 | I-70 $^1$H NMR (400 MHz, CDCl$_3$) δ 11.47 (s, 1H), 10.03 (s, 1H), 7.39 (d, J = 8.2 Hz, 2H), 7.21 (d, J = 8.2 Hz, 2H), 5.62 (s, 1H), 4.16 (dd, J = 8.5, 3.4 Hz, 1H), 3.34 (m, 1H), 3.24-3.12 (m, 1H), 2.59-2.49 (m, 1H), 2.42 (s, 3H), 2.41-2.35 (m, 1H).<br>$^{13}$C NMR (101 MHz, CDCl$_3$) δ 194.79, 148.42, 142.04, 136.35, 134.10, 133.10, 131.55, 130.18, 122.61, 122.07, 114.64, 92.18, 80.97, 35.05, 33.33, 28.62, 13.19.<br>HR-MS (ESI) calcd. for (C$_{19}$H$_{15}$BrO$_3$ + Na)$^+$ 393.0097, found: 393.0096. |

| Structure and number | Characterization data ¹HNMR, ¹³CNMR, Mass |
|---|---|
| I-71 | ¹H NMR (400 MHz, CDCl$_3$) δ 12.45 (s, 1H), 10.43 (s, 1H), 7.93 (dd, J = 7.7, 1.4 Hz, 1H), 7.39 (dtd, J = 24.4, 7.5, 1.5 Hz, 2H), 6.95 (dd, J = 7.5, 1.2 Hz, 1H), 5.87 (s, 2H), 5.67 (s, 1H), 4.03 (d, J = 15.9 Hz, 1H), 3.74 (s, 3H), 3.68 (d, J = 15.9 Hz, 1H), 3.55 (s, 3H), 3.43 (s, 6H), 1.77 (s, 3H). <br> ¹³C NMR (101 MHz, CDCl$_3$) δ 197.62, 166.53, 159.79, 158.64, 148.40, 140.91, 140.33, 134.07, 133.12, 132.24, 131.61, 130.75, 130.51, 130.05, 126.97, 116.45, 109.50, 90.20, 55.27, 55.16, 51.62, 22.02, 14.08. <br> HR-MS (ESI) calcd. for (C$_{26}$H$_{26}$O$_8$ + Na)$^+$ 489.1520, found: 489.1521. |
| I-72 | ¹H NMR (400 MHz, CDCl$_3$) δ 12.15 (s, 1H), 10.31 (s, 1H), 6.65 (s, 1H), 5.91 (s, 1H), 5.87 (bro, 1H), 5.66 (s, 1H), 4.69 (s, 2H), 4.13 (s, 2H), 2.30 (s, 3H). <br> ¹³C NMR (101 MHz, CDCl$_3$) δ 196.19, 150.16, 143.46, 131.63, 130.15, 129.10, 123.92, 118.91, 116.40, 74.11, 69.44, 16.23. <br> HR-MS (ESI) calcd. for (C$_{12}$H$_{13}$BrO$_4$ + Na)$^+$ 322.9889, found: 322.9885. |
| I-73 | ¹H NMR (400 MHz, CDCl$_3$) δ 10.45 (s, 1H), 6.75 (s, 1H), 6.14 (s, 1H), 6.10 (s, 2H), 3.94 (s, 2H), 3.84 (s, 3H), 3.79 (s, 3H), 3.73 (s, 2H), 3.64 (s, 6H), 2.71 (s, 3H). <br> ¹³C NMR (101 MHz, CDCl$_3$) δ 205.98, 159.80, 158.95, 147.17, 140.35, 131.72, 130.72, 121.71, 120.62, 109.49, 108.25, 90.76, 55.63, 55.35, 33.24, 26.81, 22.88. |
| I-74 | ¹H NMR (400 MHz, CDCl$_3$) δ 12.26 (s, 1H), 10.27 (s, 1H), 7.44-7.39 (m, 3H), 7.34-7.28 (m, 3H), 7.25-7.17 (m, 4H), 5.91 (s, 1H), 4.38 (s, 2H), 4.35 (s, 2H), 2.45 (q, J = 7.5 Hz, 2H), 0.99 (t, J = 7.5 Hz, 3H) <br> ¹³C NMR (101 MHz, CDCl$_3$) δ 197.12, 149.26, 142.75, 138.24, 137.72, 136.95, 135.13, 130.17, 129.20, 128.55, 128.24, 128.03, 127.96, 127.52, 116.33, 72.81, 65.70, 21.86, 13.61. <br> HR-MS (ESI) calcd. for (C$_{23}$H$_{22}$O$_4$ + Na)$^+$ 385.1410, found: 385.1413. |
| I-75 | ¹H NMR (400 MHz, CDCl$_3$) δ 12.25 (s, 1H), 10.23 (s, 1H), 8.02 (dd, J = 7.8, 1.2 Hz, 1H), 7.59-7.41 (m, 2H), 7.32-7.22 (m, 3H), 7.16 (d, J = 6.3 Hz, 3H), 5.85 (s, 1H), 4.37 (d, J = 11.2 Hz, 1H), 4.28 (d, J = 4.3 Hz, 2H), 4.17 (d, J = 11.2 Hz, 1H), 3.62 (s, 3H), 1.90 (s, 3H). <br> ¹³C NMR (101 MHz, CDCl$_3$) δ 196.89, 167.02, 149.02, 142.62, 140.90, 139.52, 137.62, 134.56, 132.01, 131.61, 130.82, 130.61, 130.36, 128.57, 128.37, 128.08, 127.82, 127.76, 127.66, 126.99, 72.64, 67.76, 65.76, 52.03, 14.20. <br> HR-MS (ESI) calcd. for (C$_{26}$H$_{22}$O$_6$ + Na)$^+$ 429.1309, found: 429.1307. |
| I-76 | ¹H NMR (400 MHz, CDCl$_3$) δ 12.24 (s, 1H), 10.16 (s, 1H), 7.67 (d, J = 7.6 Hz, 2H), 7.12-6.91 (m, 7H), 6.28 (s, 1H), 4.32 (s, 2H), 4.22 (s, 2H), 2.29 (s, 3H). |

| Structure and number | Characterization data ¹HNMR, ¹³CNMR, Mass |
|---|---|
| I-77 | I-77 ¹H NMR (400 MHz, CDCl$_3$) δ 12.26 (s, 1H), 10.23 (s, 1H), 8.07 (d, J = 8.4 Hz, 2H), 7.34-7.14 (m, 7H), 5.96 (s, 1H), 4.34 (s, 2H), 4.32 (s, 2H), 3.98 (s, 3H), 1.96 (s, 3H). ¹³C NMR (101 MHz, CDCl$_3$) δ 196.93, 166.99, 149.37, 143.51, 143.13, 137.44, 134.53, 130.40, 130.21, 129.75, 129.47, 128.59, 128.56, 128.12, 128.08, 116.32, 72.92, 65.40, 52.38, 14.53. HR-MS (ESI) calcd. for (C$_{26}$H$_{22}$O$_6$ + Na)$^+$ 429.1309, found: 429.1308. |
| I-78 | I-78 ¹H NMR (400 MHz, CDCl$_3$) δ 12.15 (s, 1H), 10.13 (s, 1H), 7.28 (d, J = 8.5 Hz, 2H), 6.90 (d, J = 8.5 Hz, 2H), 5.99-5.91 (m, 1H), 5.90 (s, 1H), 5.04 (dd, J = 10.2, 1.5 Hz, 1H), 4.70 (dd, J = 17.2, 1.6 Hz, 1H), 4.58 (s, 2H), 4.53 (s, 2H), 3.81 (s, 3H), 3.41-3.36 (m, 2H), 3.21-3.09 (m, 1H), 1.34 (d, J = 7.0 Hz, 6H). ¹³C NMR (101 MHz, CDCl$_3$) δ 196.73, 159.67, 148.84, 144.13, 140.85, 136.96, 129.91, 129.79, 129.24, 128.60, 116.66, 115.95, 114.10, 72.80, 63.77, 55.45, 32.38, 29.88, 19.91. HR-MS (ESI) calcd. for (C$_{22}$H$_{26}$O$_5$ + Na)$^+$ 393.1672, found: 392.1675. |
| I-79 | I-79 ¹H NMR (400 MHz, CDCl$_3$) δ 12.28 (s, 1H), 10.38 (s, 1H), 7.49-7.38 (m, 3H), 7.21 (d, J = 6.8 Hz, 2H), 5.87 (s, 1H), 3.62 (s, 2H), 2.34 (t, J = 6.3 Hz, 2H), 1.95 (s, 3H), 1.52 (heptet, J = 7.1 Hz, 1H), 1.24 (q, J = 7.1 Hz, 2H), 0.81 (s, 3H), 0.79 (s, 3H). ¹³C NMR (101 MHz, CDCl$_3$) δ 196.17, 149.24, 142.20, 138.49, 134.92, 131.60, 130.00, 129.40, 128.53, 127.59, 115.45, 38.26, 31.67, 30.02, 27.33, 22.30, 14.75. HR-MS (ESI) calcd. for (C$_{20}$H$_{24}$O$_3$S + Na)$^+$ 367.1338, found: 367.1343. |
| I-80 | I-80 ¹H NMR (400 MHz, CDCl$_3$) δ 12.16 (s, 1H), 10.36 (s, 1H), 6.57 (s, 1H), 5.72 (s, 1H), 3.90 (s, 2H), 2.49 (t, J = 7.1 Hz, 2H), 2.29 (s, 3H), 1.66 (heptet, J = 6.6 Hz, 2H), 1.48 (q, J = 7.1 Hz, 2H), 0.91 (s, 3H), 0.89 (s, 3H). ¹³C NMR (101 MHz, CDCl$_3$) δ 195.12, 150.30, 142.58, 131.85, 131.79, 123.82, 115.50, 38.45, 32.54, 30.17, 27.65, 22.41, 16.25. HR-MS (ESI) calcd. for (C$_{14}$H$_{20}$O$_3$S + H)$^+$ 269.1206, found: 269.1206. |
| I-81 | I-81 ¹H NMR (400 MHz, CDCl$_3$) δ 12.11 (s, 1H), 10.24 (s, 1H), 6.64 (s, 1H), 5.85 (s, 1H), 4.62 (s, 2H), 3.49 (t, J = 6.7 Hz, 2H), 2.28 (s, 3H), 1.67 (heptet, J = 6.7 Hz, 1H), 1.47 (q, J = 6.8 Hz, 2H), 0.88 (s, 3H), 0.86 (s, 3H). ¹³C NMR (101 MHz, CDCl$_3$) δ 196.33, 150.02, 143.09, 131.64, 131.44, 123.53, 116.38, 70.42, 68.94, 38.59, 25.12, 22.66, 16.23. HR-MS (ESI) calcd. for (C$_{14}$H$_{20}$O$_4$ + Na)$^+$ 275.1254, found: 275.1259. |
| I-82 | I-82 ¹H NMR (400 MHz, CDCl$_3$) δ 12.25 (s, 1H), 10.27 (s, 1H), 7.50-7.33 (m, 3H), 7.15 (d, J = 7.4 Hz, 2H), 5.99 (s, 1H), 4.32 (s, 2H), 3.28 (t, J = 6.6 Hz, 2H), 1.98 (s, 3H), 1.62 (heptet, J = 6.7 Hz, 1H), 1.36 (q, J = 6.7 Hz, 2H), 0.84 (s, 3H), 0.82 (s, 3H). ¹³C NMR (101 MHz, CDCl$_3$) δ 197.24, 149.12, 142.78, 138.62, 135.33, 130.95, 130.05, 129.22, 128.41, 127.46, 116.23, 68.79, 66.17, 38.52, 24.98, 22.60, 14.60. HR-MS (ESI) calcd. for (C$_{20}$H$_{24}$O$_4$ + Na)$^+$ 351.1567, found: 351.1571. |

| Structure and number | Characterization data ¹HNMR, ¹³CNMR, Mass |
|---|---|
| I-83 | I-83 ¹H NMR (400 MHz, CDCl$_3$) δ 12.10 (s, 1H), 10.27 (s, 1H), 6.65 (s, 1H), 5.78 (s, 1H), 5.38 (d, J = 4.8 Hz, 1H), 4.68 (s, 2H), 3.38-3.22 (m, 1H), 2.52-2.36 (m, 2H), 2.28 (s, 3H), 2.32-2.20 (m, 1H), 2.16-2.04 (m, 2H), 2.00-1.82 (m, 4H), 1.73-1.63 (m, 3H), 1.59-1.45 (m, 3H), 1.34-1.23 (m, 2H), 1.12-0.96 (m, 2H), 1.03 (s, 3H), 0.89 (s, 3H).<br>¹³C NMR (101 MHz, CDCl$_3$) δ 196.38, 150.06, 143.14, 140.97, 131.73, 131.56, 123.51, 121.27, 116.37, 78.78, 67.54, 51.91, 50.40, 47.68, 39.21, 37.22, 37.14, 35.97, 31.61, 31.57, 30.95, 28.42, 22.01, 20.49, 19.52, 16.25, 13.68.<br>HR-MS (ESI) calcd. for (C$_{28}$H$_{36}$O$_5$ + Na)$^+$ 475.2455, found: 475.2460. |
| I-84 | I-84 ¹H NMR (400 MHz, CDCl$_3$) δ 12.25 (s, 1H), 10.32 (s, 1H), 7.46-7.38 (m, 3H), 7.17-7.12 (m, 2H), 5.90 (s, 1H), 5.28 (d, J = 4.7 Hz, 1H), 4.39 (s, 2H), 3.09-2.97 (m, 1H), 2.48-2.41 (m, 1H), 2.17-2.04 (m, 4H), 1.99 (s, 3H), 1.95-1.88 (m, 1H), 1.87-1.76 (m, 2H), 1.71-1.59 (m, 4H), 1.57-1.33 (m, 3H), 1.32-1.21 (m, 2H), 0.98 (s, 3H), 0.97-0.91 (m, 2H), 0.87 (s, 3H).<br>¹³C NMR (101 MHz, CDCl$_3$) δ 197.30, 149.19, 142.86, 141.05, 138.61, 135.35, 131.00, 130.06, 129.27, 128.44, 127.55, 121.08, 116.23, 78.45, 63.34, 51.92, 50.39, 47.67, 39.10, 37.19, 37.09, 35.97, 31.61, 31.58, 30.93, 28.35, 22.01, 20.47, 19.50, 14.61, 13.68.<br>HR-MS (ESI) calcd. for (C$_{34}$H$_{40}$O$_5$ + Na)$^+$ 551.2768, found: 551.2776. |
| I-85 | I-85 ¹H NMR (400 MHz, CDCl$_3$) δ 12.12 (s, 1H), 10.26 (s, 1H), 6.64 (s, 1H), 5.83 (s, 1H), 5.35 (t, J = 6.5 Hz, 1H), 5.09 (t, J = 6.6 Hz, 1H), 4.62 (s, 2H), 4.03 (d, J = 6.9 Hz, 2H), 2.28 (s, 3H), 2.15-2.01 (m, 4H), 1.67 (s, 3H), 1.65 (s, 3H), 1.60 (s, 3H).<br>¹³C NMR (101 MHz, CDCl$_3$) δ 196.36, 150.01, 143.12, 141.35, 131.89, 131.61, 131.40, 124.00, 123.72, 120.37, 116.42, 69.11, 66.63, 39.70, 26.45, 25.81, 17.81, 16.59, 16.21.<br>HR-MS (ESI) calcd. for (C$_{19}$H$_{26}$O$_4$ + Na)$^+$ 341.1723, found: 341.1729. |
| I-86 | I-86 ¹H NMR (400 MHz, CDCl$_3$) δ 12.28 (s, 1H), 10.27 (s, 1H), 10.10 (s, 1H), 7.97 (d, J = 8.1 Hz, 2H), 7.36 (d, J = 8.0 Hz, 2H), 6.02 (s, 1H), 4.28 (s, 2H), 3.29 (t, J = 6.6 Hz, 2H), 1.97 (s, 3H), 1.69 - 1.54 (m, 1H), 1.37 (q, J = 6.7 Hz, 2H), 0.83 (d, J = 6.6 Hz, 6H).<br>¹³C NMR (101 MHz, CDCl$_3$) δ 196.99, 191.97, 149.48, 145.40, 143.10, 135.67, 133.95, 130.97, 130.15, 129.82, 128.88, 116.36, 69.07, 66.10, 38.52, 25.03, 22.60, 14.54.<br>HR-MS (ESI) calcd. for (C$_{21}$H$_{24}$O$_5$ + Na)$^+$ 379.1516, found: 375.1520. |
| I-87 | I-87 ¹H NMR (400 MHz, CDCl$_3$) δ 12.11 (s, 1H), 10.21 (s, 1H), 7.24 (d, J = 8.6 Hz, 2H), 6.88 (d, J = 8.6 Hz, 2H), 6.63 (s, 1H), 5.85 (s, 1H), 4.63 (s, 2H), 4.47 (s, 2H), 3.80 (s, 3H), 2.28 (s, 3H).<br>¹³C NMR (101 MHz, CDCl$_3$) δ 196.26, 159.55, 150.05, 143.19, 131.66, 131.11, 129.77, 129.71, 123.78, 116.40, 114.05, 72.04, 69.10, 55.41, 16.21.<br>HR-MS (ESI) calcd. for (C$_{17}$H$_{18}$O$_5$ + H)$^+$ 303.1227, found: 303.1225. |

| Structure and number | Characterization data ¹HNMR, ¹³CNMR, Mass |
|---|---|
| I-88 | I-88 ¹H NMR (400 MHz, CDCl₃) δ 12.24 (s, 1H), 10.22 (s, 1H), 7.46-7.03 (m, 10H), 5.94 (s, 1H), 5.82 (ddd, J = 17.1, 10.5, 6.7 Hz, 1H), 5.14-5.04 (m, 2H), 4.54 (d, J = 6.6 Hz, 1H), 4.30 (dd, J = 24.4, 10.8 Hz, 2H), 2.01-1.92 (m, 3H). |
| I-89 | I-89 ¹H NMR (400 MHz, CDCl₃) δ 12.30 (s, 1H), 10.25 (s, 1H), 7.42-7.32 (m, 5H), 5.91 (s, 1H), 4.83 (s, 2H), 4.67 (s, 2H), 4.62 (s, 2H), 2.39 (s, 3H), 0.92 (s, 9H), 0.10 (s, 6H). <br> ¹H NMR (400 MHz, CDCl₃) δ 12.30, 10.25, 7.41, 7.39, 7.37, 7.36, 7.34, 5.91, 4.83, 4.67, 4.62, 2.39, 0.92, 0.10. <br> HR-MS (ESI) calcd. for (C₂₃H₃₂O₅Si + Na)⁺ 439.1911, found: 439.1919. |
| I-90 | I-90 ¹H NMR (400 MHz, CDCl₃) δ 12.21 (s, 1H), 10.23 (s, 1H), 7.44-7.31 (m, 5H), 6.04-5.81 (m, 2H), 5.03 (d, J = 10.2 Hz, 1H), 4.75 (d, J = 17.2 Hz, 1H), 4.68 (s, 2H), 4.61 (s, 2H), 3.41 (d, J = 4.3 Hz, 2H), 2.28 (s, 3H). <br> ¹³C NMR (101 MHz, CDCl₃) δ 196.75, 148.40, 143.19, 137.73, 136.05, 131.77, 129.78, 129.06, 128.68, 128.23, 128.17, 116.69, 115.69, 72.98, 63.90, 32.42, 12.76. <br> HR-MS (ESI) calcd. for (C₁₉H₂₀O₄ + Na)⁺ 335.1254, found: 335.1260. |
| I-91 | I-91 ¹H NMR (400 MHz, CDCl₃) δ 12.16 (s, 1H), 10.15 (s, 1H), 7.38-7.30 (m, 5H), 5.99-5.91 (m, 1H), 5.90 (s, 1H), 5.03 (dd, J = 10.2, 1.6 Hz, 1H), 4.70 (dd, J = 17.2, 1.6 Hz, 1H), 4.61 (s, 2H), 4.59 (s, 2H), 3.43-3.36 (m, 2H), 3.21-3.10 (m, 1H), 1.34 (d, J = 7.0 Hz, 6H). <br> ¹³C NMR (101 MHz, CDCl₃) δ 196.69, 148.87, 144.19, 140.85, 137.68, 136.93, 129.12, 128.70, 128.63, 128.32, 128.23, 116.68, 115.98, 73.16, 64.12, 32.39, 29.92, 19.92. <br> HR-MS (ESI) calcd. for (C₂₁H₂₄O₄ + Na)⁺ 363.1567, found: 363.1573. |
| I-92 | I-92 ¹H NMR (400 MHz, CDCl₃) δ 10.45 (s, 1H), 7.46-7.22 (m, 6H), 4.88 (s, 2H), 4.67 (s, 2H), 3.97 (s, 3H), 3.84 (s, 3H), 2.33 (s, 3H). <br> ¹³C NMR (101 MHz, CDCl₃) δ 191.87, 157.40, 150.32, 139.91, 138.49, 136.75, 128.55, 127.88, 127.77, 125.35, 124.78, 73.20, 69.96, 62.21, 60.38, 16.77. |
| I-93 | I-93 ¹H NMR (400 MHz, CDCl₃) δ 7.44-7.36 (m, 4H), 7.36-7.30 (m, 1H), 7.04 (s, 1H), 4.62 (s, 2H), 4.58 (s, 2H), 4.52 (s, 2H), 3.89 (s, 3H), 3.85 (s, 3H), 3.36 (s, 3H), 2.29 (s, 3H). <br> 13C NMR (101 MHz, CDCl₃) δ 152.29, 151.06, 138.44, 133.58, 132.33, 128.51, 128.24, 128.09, 127.78, 127.08, 72.73, 69.67, 65.52, 61.43, 60.13, 58.31, 15.97. |
| I-94 | I-94 1H NMR (400 MHz, CDCl₃) δ 6.97 (s, 1H), 4.61 (s, 2H), 4.56 (d, J = 5.7 Hz, 2H), 3.85 (s, 3H), 3.82 (s, 3H), 3.43 (s, 3H), 3.33 (t, J = 6.1 Hz, 1H), 2.26 (s, 3H). <br> ¹³C NMR (101 MHz, CDCl₃) δ 152.10, 150.99, 137.22, 132.82, 127.77, 127.50, 64.01, 61.47, 60.18, 58.25, 15.90. <br> HR-MS (ESI) calcd. for (C₁₂H₁₈O₄ + Na)⁺ 249.1097, found: 249.1098. |

| Structure and number | Characterization data $^1$HNMR, $^{13}$CNMR, Mass |
|---|---|
| I-95 | $^1$H NMR (400 MHz, CDCl$_3$) δ 12.11 (s, 1H), 10.19 (s, 1H), 7.29 (dd, J = 10.0, 5.8 Hz, 3H), 7.13 (dt, J = 7.4, 4.3 Hz, 1H), 5.62 (s, 1H), 4.01 (s, 2H), 3.11 (s, 2H), 2.29 (s, 3H), 2.16 (s, 3H). $^{13}$C NMR (101 MHz, CDCl$_3$) δ 195.21, 149.97, 146.80, 142.54, 141.73, 140.18, 134.41, 133.44, 132.93, 126.45, 124.54, 123.55, 123.39, 118.84, 116.32, 40.32, 30.93, 16.43, 10.64. HR-MS (ESI) calcd. for (C$_{19}$H$_{18}$O$_3$ + Na)$^+$ 317.1148, found: 317.1147.6.43, 10.64. |
| I-96 | $^1$H NMR (400 MHz, CDCl$_3$) δ 7.93 (br, 1H), 7.93-7.30 (m, 5H), 6.59 (s, 1H), 5.86 (br, 1H), 4.84 (s, 2H), 4.48 (s, 2H), 4.40 (s, 2H), 3.03 (br, 1H), 2.20 (s, 3H). $^{13}$C NMR (101 MHz, CDCl$_3$) δ 143.80, 143.44, 137.88, 128.64, 128.17, 128.02, 126.00, 124.27, 123.26, 122.21, 72.13, 71.21, 60.11, 15.47. |
| I-97 | $^1$H NMR (400 MHz, CDCl$_3$) δ 7.75 (s, 1H), 6.35 (s, 1H), 6.16 (s, 2H), 5.46 (s, 1H), 5.08 (s, 2H), 3.82 (s, 3H), 3.77 (s, 6H), 3.75 (s, 2H), 2.44 (br, 1H), 2.12 (s, 3H). $^{13}$C NMR (101 MHz, CDCl$_3$) δ 159.82, 158.91, 142.77, 141.16, 129.72, 123.34, 122.21, 120.57, 109.94, 91.00, 60.68, 55.91, 55.47, 24.25, 15.69. |
| I-98 | $^1$H NMR (400 MHz, CDCl$_3$) δ 7.76 (br, 1H), 7.23 (t, J = 7.2 Hz, 2H), 7.18-7.10 (m, 1H), 7.00 (d, J = 6.9 Hz, 2H), 5.49 (br, 1H), 4.94 (s, 1H), 4.81 (s, 1H), 4.46-4.25 (m, 2H), 2.89-2.79 (m 1H), 2.74-2.65 (m, 1H), 2.60-2.50 (m, 1H), 2.00-1.95 (m, 1H), 1.87 (s, 3H), 1.78-1.52 (m, 1H). $^{13}$C NMR (101 MHz, CDCl$_3$) δ 146.14, 142.27, 142.00, 136.57, 132.29, 128.48, 127.38, 125.99, 120.71, 117.11, 61.93, 50.12, 35.92, 29.25, 12.35. |
| I-99 | HR-MS (ESI) calcd. for (C$_{17}$H$_{18}$O$_6$ + Na)$^+$ 341.0996, found: 341.0999. |
| I-100 | HR-MS (ESI) calcd. for (C$_{20}$H$_{24}$O$_6$ + Na)$^+$ 383.1465, found: 383.1461. |

Example 29

Determination of Effects of Compounds I-26, I-39, I-49, I-50, I-96 and I-97 on the Proliferation of Human Gastric Cancer Cells MKN45

(1) Cell Culture

The original culture medium for human gastric cancer cells MKN45 was removed, and human gastric cancer cells MKN45 were rinsed with 2 mL of phosphate buffer saline (PBS), digested with 0.5 mL of pancreatic enzyme for 3 min. 2 mL of culture medium was added to the cells and the mixture was transferred to a centrifuge tube. The mixture was centrifuged (200 g) for 5 min. The supernatant was removed. 2 mL of culture medium was sprayed five times to the remaining solution. 0.5 mL of cell suspension was transferred to an Eppendorf (EP) tube and the cells were counted. The cells were cultured on a 96-well plate, each well having 2000 cells, 3 wells for each compound. The numbers of the required cells and wells and the amount of culture medium were calculated. The cells were diluted by the culture medium. 100 µL culture medium was added to each well and were evenly dispersed, each well containing 2000 cells. The cells were transferred to the wells using a pipette, and cultured in an incubator.

(2) Adding Compounds to Culture Medium

The original culture medium was discarded, and the mother liquor of each compound was diluted to final concentrations of 0, 5, 15, 30, 45 and 60 µM, respectively. Each diluent was uniformized. To each head of a multichannel pipette, 100 µL of the diluent was introduced. Three heads were employed. The diluents were added to 3 marked wells (the cells were undamaged) of a tilted 96-well plate, respectively. Different concentrations of diluents were added to three different marked wells and evenly mixed by alternately sucking and blowing with the multichannel pipette 3 times. The 96-well plate was shaken slightly twice, and cultured in a $CO_2$ incubator.

(3) MTT Assay

The cells were cultured in different compounds for 48 h and were then detected. Specifically, a clean bench was turned on for 15 min, and phosphate buffer saline (PBS) was pre-heated in a warm water bath for 15 min. MTT was taken out of a refrigerator at −20 degrees, protected from light and thawed (MTT stock solution was 5 mg/mL). MTT and a culture medium were mixed evenly in a V-shaped groove to yield a mixture comprising 500 µg/mL MTT and a culture medium (a volume ratio thereof being 1:10). 100 µL of the prepared MTT mixture was added to each well of the 96-well plate using the multichannel pipette, and then incubated at 37° C. for an appropriate time (1 h), thereby reducing the MTT to formazan (purple crystals formed in the cells under a microscope, which were different in medicated cells and unmedicated cells). The upper liquid was removed with a white pipette tip attached to a vacuum pump. For each concentration of the compounds, 3 pipette tips were employed. After the incubation, the MTT mixture was discarded, and then 100 µL of DMSO was added to each well using the multichannel pipette. The 96-well plate was shaken in a shaker for 10 min (until the purple crystals were dissolved in the cells under the microscope).

The absorbance value of the cells was measured at a wavelength of 550 nm with a microplate reader. The survival rate of the cells treated with different concentrations of compounds was calculated to make a scatter plot. The $IC_{50}$ results of each compound on the proliferation of human gastric cancer cells MKN45 were shown in Table 1, where Gossypol I-A9 is a control sample.

TABLE 1

$IC_{50}$ results of each compound on the proliferation of human gastric cancer cells MKN45

| Cancer cell | Compound number | $IC_{50}$ (µM) |
|---|---|---|
| MKN45 | I-26 | 16.78 |
|  | I-39 | 6.62 |
|  | I-49 | 3.117 |
|  | I-50 | 12.34 |
|  | I-A9 | 15.408 |

Table 1 showed that Compounds I-26, I-39, I-49, I-50, I-96 and I-97 had significant inhibitory effects on human gastric cancer cells MKN45, of which Compounds I-39, I-49 and I-50 was better than the control gossypol I-A9.

Example 30

Determination of Effects of Compounds I-49, I-A2, I-A3 and I-A5 on the Proliferation of Human Ovarian Cancer Cells SKOV3

(1) Cell Culture

The original culture medium for human ovarian cancer cells SKOV3 was removed, and human ovarian cancer cells SKOV3 were rinsed with 2 mL of phosphate buffer saline (PBS), digested with 0.5 mL of pancreatic enzyme for 3 min. 2 mL of culture medium was added to the cells and the mixture was transferred to a centrifuge tube. The mixture was centrifuged (200 g) for 5 min. The supernatant was removed. 2 mL of culture medium was sprayed five times to the remaining solution. 0.5 mL of cell suspension was transferred to an Eppendorf (EP) tube and the cells were counted. The cells were cultured on a 96-well plate, each well having 2000 cells, 3 wells for each compound. The numbers of the required cells and wells and the amount of culture medium were calculated. The cells were diluted by the culture medium. 100 µL culture medium was added to each well and were evenly dispersed, each well containing 2000 cells. The cells were transferred to the wells using a pipette, and cultured in an incubator.

(2) Adding Compounds to Culture Medium

The original culture medium was discarded, and the mother liquor of each compound was diluted to final concentrations of 0, 1, 2, 4, 8 and 16 µM, respectively. Each diluent was uniformized. To each head of a multichannel pipette, 100 µL of the diluent was introduced. Three heads were employed. The diluents were added to 3 marked wells (the cells were undamaged) of a tilted 96-well plate, respectively. Different concentrations of diluents were added to three different marked wells and evenly mixed by alternately sucking and blowing with the multichannel pipette 3 times. The 96-well plate was shaken slightly twice, and cultured in a $CO_2$ incubator.

(3) MTT Assay

The cells were cultured in different compounds for 48 h and were then detected. Specifically, a clean bench was turned on for 15 min, and phosphate buffer saline (PBS) was pre-heated in a warm water bath for 15 min. MTT was taken out of a refrigerator at −20 degrees, protected from light and thawed (MTT stock solution was 5 mg/mL). MTT and a culture medium were mixed evenly in a V-shaped groove to yield a mixture comprising 500 µg/mL MTT and a culture medium (a volume ratio thereof being 1:10). 100 μL of the prepared MTT mixture was added to each well of the 96-well plate using the multichannel pipette, and then incubated at 37° C. for an appropriate time (1 h), thereby reducing the MTT to formazan (purple crystals formed in the cells under a microscope, which were different in medicated cells and unmedicated cells). The upper liquid was removed with a white pipette tip attached to a vacuum pump. For each concentration of the compounds, 3 pipette tips were employed. After the incubation, the MTT mixture was discarded, and then 100 μL of DMSO was added to each well using the multichannel pipette. The 96-well plate was shaken in a shaker for 10 min (until the purple crystals were dissolved in the cells under the microscope).

The absorbance value of the resulting solution was detected at a wavelength of 550 nm with a microplate reader. The survival rate of cells treated with different concentrations of drugs was calculated in accordance with the requirements to make a scatter plot. The $IC_{50}$ results of each compound on the proliferation of human ovarian cancer cells SKOV3 were shown in Table 2, wherein Gossypol I-A9 is a control sample.

TABLE 2

IC$_{50}$ results of each compound on the proliferation of human ovarian cancer cells SKOV3

| Cancer cell | Compound number | IC$_{50}$ (μM) |
|---|---|---|
| SKOV3 | I-49 | 5.922 |
| | I-A2 | 11.52 |
| | I-A3 | 6.454 |
| | I-A5 | 9.79 |
| | I-97 | 35 |
| | I-A9 | 9.553 |

Table 2 showed that Compounds I-49, I-A2, I-A3 and I-A5 had significant inhibitory effects on human ovarian cancer cells SKOV3, of which the effects of Compounds I-49 and I-A3 were superior to that of the gossypol I-A9 as a control sample, while the effects of the compounds I-A2 and I-A5 were similar to that of the gossypol I-A9.

Example 31

Determination of Effects of Compounds I-28, I-29, I-45 and I-A4 on the Proliferation of Human Lung Cancer Cells A549

(1) Cell Culture

The original culture medium for human lung cancer cells A549 was removed, and human lung cancer cells A549 were rinsed with 2 mL of phosphate buffer saline (PBS), digested with 0.5 mL of pancreatic enzyme for 3 min. 2 mL of culture medium was added to the cells and the mixture was transferred to a centrifuge tube. The mixture was centrifuged (200 g) for 5 min. The supernatant was removed. 2 mL of culture medium was sprayed five times to the remaining solution. 0.5 mL of cell suspension was transferred to an Eppendorf (EP) tube and the cells were counted. The cells were cultured on a 96-well plate, each well having 2000 cells, 3 wells for each compound. The numbers of the required cells and wells and the amount of culture medium were calculated. The cells were diluted by the culture medium. 100 μL culture medium was added to each well and were evenly dispersed, each well containing 2000 cells. The cells were transferred to the wells using a pipette, and cultured in an incubator.

(2) Adding Compounds to Culture Medium

The original culture medium was discarded, and the mother liquor of each compound was diluted to final concentrations of 0, 5, 10, 20, 30, 60 and 80 μM, respectively. Each diluent was uniformized. To each head of a multichannel pipette, 100 μL of the diluent was introduced. Three heads were employed. The diluents were added to 3 marked wells (the cells were undamaged) of a tilted 96-well plate, respectively. Different concentrations of diluents were added to three different marked wells and evenly mixed by alternately sucking and blowing with the multichannel pipette 3 times. The 96-well plate was shaken slightly twice, and cultured in a $CO_2$ incubator.

(3) MTT Assay

The cells were cultured in different compounds for 48 h and were then detected. Specifically, a clean bench was turned on for 15 min, and phosphate buffer saline (PBS) was pre-heated in a warm water bath for 15 min. MTT was taken out of a refrigerator at −20 degrees, protected from light and thawed (MTT stock solution was 5 mg/mL). MTT and a culture medium were mixed evenly in a V-shaped groove to yield a mixture comprising 500 μg/mL MTT and a culture medium (a volume ratio thereof being 1:10). 100 μL of the prepared MTT mixture was added to each well of the 96-well plate using the multichannel pipette, and then incubated at 37° C. for an appropriate time (1 h), thereby reducing the MTT to formazan (purple crystals formed in the cells under a microscope, which were different in medicated cells and unmedicated cells). The upper liquid was removed with a white pipette tip attached to a vacuum pump. For each concentration of the compounds, 3 pipette tips were employed. After the incubation, the MTT mixture was discarded, and then 100 μL of DMSO was added to each well using the multichannel pipette. The 96-well plate was shaken in a shaker for 10 min (until the purple crystals were dissolved in the cells under the microscope).

The absorbance value of the resulting solution was detected at a wavelength of 550 nm with a microplate reader. The survival rate of cells treated with different concentrations of drugs was calculated in accordance with the requirements to make a scatter plot. The $IC_{50}$ results of each compound on the proliferation of human lung cancer cells A549 were shown in Table 3, where Gossypol I-A9 is a control sample.

TABLE 3

IC$_{50}$ results of each compound on the proliferation of human lung cancer cells A5499

| Cancer cell | Compound number | IC$_{50}$ (μM) |
|---|---|---|
| A549 | I-28 | 67.59 |
| | I-29 | 42.07 |
| | I-45 | 26.04 |
| | I-A4 | 58.87 |
| | I-A9 | 18.06 |

Table 3 showed that Compounds I-28, I-29, I-45 and I-A4 had inhibitory effects on human lung cancer cells A549, but were slightly inferior to that of the Gossypol I-A9 as a control sample.

Example 32

Determination of Effects of Compounds I-5, I-21, I-24, I-25, I-26, I-29, I-31, I-41, I-42, I-43, I-44, I-45, I-46, I-47, I-48, I-49, I-50, I-51, I-53, I-55, I-100, I-A2, I-A3, I-A5, I-A6 and I-A8 on the Proliferation of Human Prostate Cancer Cells PC3

(1) Cell Culture

The original culture medium for human prostate cancer cells PC3 was removed, and human prostate cancer cells PC3 were rinsed with 2 mL of phosphate buffer saline (PBS), digested with 0.5 mL of pancreatic enzyme for 3 min. 2 mL of culture medium was added to the cells and the mixture was transferred to a centrifuge tube. The mixture was centrifuged (200 g) for 5 min. The supernatant was removed. 2 mL of culture medium was sprayed five times to the remaining solution. 0.5 mL of cell suspension was transferred to an Eppendorf (EP) tube and the cells were counted. The cells were cultured on a 96-well plate, each well having 2000 cells, 3 wells for each compound. The numbers of the required cells and wells and the amount of culture medium were calculated. The cells were diluted by the culture medium. 100 µL culture medium was added to each well and were evenly dispersed, each well containing 2000 cells. The cells were transferred to the wells using a multichannel pipette, and cultured in an incubator.

(2) Adding Compounds to Culture Medium

The original culture medium was discarded, and the mother liquor of each compound was diluted to final concentrations of 0, 2, 4, 8, 16 and 32 µM, respectively. Each diluent was uniformized. To each head of a multichannel pipette, 100 µL of the diluent was introduced. Three heads were employed. The diluents were added to 3 marked wells (the cells were undamaged) of a tilted 96-well plate, respectively. Different concentrations of diluents were added to three different marked wells and evenly mixed by alternately sucking and blowing with the multichannel pipette 3 times. The 96-well plate was shaken slightly twice, and cultured in a $CO_2$ incubator.

(3) MTT Assay

The cells were cultured in different compounds for 48 h and were then detected. Specifically, a clean bench was turned on for 15 min, and phosphate buffer saline (PBS) was pre-heated in a warm water bath for 15 min. MTT was taken out of a refrigerator at −20 degrees, protected from light and thawed (MTT stock solution was 5 mg/mL). MTT and a culture medium were mixed evenly in a V-shaped groove to yield a mixture comprising 500 µg/mL MTT and a culture medium (a volume ratio thereof being 1:10). 100 µL of the prepared MTT mixture was added to each well of the 96-well plate using the multichannel pipette, and then incubated at 37° C. for an appropriate time (1 h), thereby reducing the MTT to formazan (purple crystals formed in the cells under a microscope, which were different in medicated cells and unmedicated cells). The upper liquid was removed with a white pipette tip attached to a vacuum pump. For each concentration of the compounds, 3 pipette tips were employed. After the incubation, the MTT mixture was discarded, and then 100 µL of DMSO was added to each well using the multichannel pipette. The 96-well plate was shaken in a shaker for 10 min (until the purple crystals were dissolved in the cells under the microscope).

The absorbance value of the resulting solution was detected at a wavelength of 550 nm with a microplate reader. The survival rate of cells treated with different concentrations of drugs was calculated in accordance with the requirements to make a scatter plot. The $IC_{50}$ results of each compound on the proliferation of human lung cancer cells A549 were shown in Table 4, where Gossypol I-A9 is a control sample.

TABLE 4

$IC_{50}$ results of each compound on the proliferation of human prostate cancer cells PC3

| Cancer cell | Compound number | $IC_{50}$ (µM) |
|---|---|---|
| PC3 | I-5 | 7.091 |
| | I-21 | 8.085 |
| | I-24 | 7.24 |
| | I-25 | 8.322 |
| | I-26 | 10.114 |
| | I-29 | 4.258 |
| | I-31 | 7.25 |
| | I-41 | 1.759 |
| | I-42 | 2.801 |
| | I-43 | 9.644 |
| | I-44 | 2.913 |
| | I-45 | 6.571 |
| | I-46 | 6.405 |
| | I-47 | 8.119 |
| | I-48 | 22.392 |
| | I-49 | 13.097 |
| | I-50 | 2.882 |
| | I-51 | 5.272 |
| | I-53 | 6.647 |
| | I-55 | 2.049 |
| | I-A2 | 4.998 |
| | I-A3 | 6.544 |
| | I-A5 | 4.185 |
| | I-A6 | 3.453 |
| | I-A8 | 2.371 |
| | I-A9 | 10.049 |

Table 4 showed that Compounds I-5, I-21, I-24, I-25, I-26, I-29, I-31, I-41, I-42, I-43, I-44, I-45, I-46, I-47, I-48, I-49, I-50, I-51, I-53, I-55, I-100, I-A2, I-A3, I-A5, I-A6 and I-A8 had significant inhibitory effects on human prostate cancer cells PC3, most of which including I-5, I-21, I-24, I-25, I-29, I-31, I-41, I-42, I-43, I-44, I-45, I-46, I-47, I-50, I-51, I-53, I-55, I-A2, I-A3, I-A5, I-A6 and I-A8 were superior than the gossypol I-A9 as a control sample.

The experimental results showed that the polysubstituted benzene compounds having biological activity provided by the disclosure can inhibit the proliferation of cancer cells, thus revealing their potential for drug development, and using as lead compounds for further development of new anti-cancer drugs.

It will be obvious to those skilled in the art that changes and modifications may be made, and therefore, the aim in the appended claims is to cover all such changes and modifications.

What is claimed is:

1. A compound, having a formula I or I':

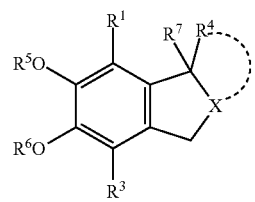

I

-continued

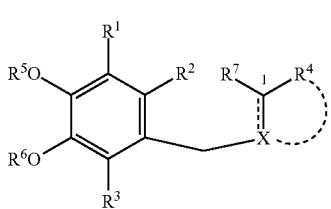

(I')

wherein:
X represents carbon, sulfur, or oxygen;
$R^1$ represents a $C_{1-16}$ alkyl, $C_{2-16}$ alkenyl, or $C_{2-10}$ alkynyl;
$R^2$ represents hydrogen, halogen, $C_{1-16}$ alkyl, $C_{2-16}$ alkenyl, or $C_{2-10}$ alkynyl; or an aryl group or a substituted aryl group by 1-5 groups selected from halogen, $C_{1-26}$ alkyl, $C_{1-3}$ halogenated alkyl, O—$C_{1-3}$ alkyl, hydroxyl, amino, nitro, cyano group, aldehyde group and ester group; or a heteroaryl group or a substituted heteroaryl group by 1-5 groups selected from halogen, $C_{1-26}$ alkyl, $C_{1-3}$ halogenated alkyl, O—$C_{1-3}$ alkyl, hydroxyl, amino, nitro, cyano group, aldehyde group and ester group;
the heteroaryl group is a 3-10-membered heteroaryl group comprising N, S, O, or a combination thereof;
$R^3$ represents $C_{1-6}$ aldehyde group, $C_{2-6}$ acyl group, —COOH, hydroxyl-substituted $C_{1-6}$ alkyl, —$CH_2O$—$C_{1-6}$ alkyl or —$CO_2$—$C_{1-6}$ alkyl;
$R^4$ and $R^7$, at each occurrence, represent hydrogen, a $C_{1-20}$ alkyl, $C_{2-36}$ alkenyl, or $C_{2-10}$ alkynyl; or an aryl group or a substituted aryl group by 1-5 groups selected from halogen, $C_{1-3}$ halogenated alkyl, O—$C_{1-3}$ alkyl, $C_{1-25}$ alkyl, hydroxyl, amino, nitro, cyano group, aldehyde group and ester group;
$R^5$ and $R^6$, at each occurrence, represent hydrogen, $C_{1-6}$ alkyl or $C_{1-6}$ silicon;
wherein the dotted line in formula I optionally comprises a carbon chain connecting $R^4$ to X; and
wherein the dotted line in formula I' optionally comprises a carbon chain connecting $R^4$ to X.

2. The compound of claim 1, wherein:
X represents carbon, sulfur, or oxygen;
$R^1$ represents a $C_{1-4}$ alkyl, $C_{2-4}$ alkenyl, or $C_{3-7}$ alkynyl;
$R^2$ represents hydrogen, halogen, $C_{1-4}$ alkyl, $C_{2-4}$ alkenyl, or $C_{3-7}$ alkynyl; or an aryl group or a substituted aryl group by 1-5 groups selected from halogen, $C_{1-26}$ alkyl, $C_{1-3}$ halogenated alkyl, O—$C_{1-3}$ alkyl, hydroxyl, amino, nitro, cyano group, aldehyde group and ester group; or a heteroaryl group or a substituted heteroaryl group by 1-5 groups selected from halogen, $C_{1-6}$ alkyl, $C_{1-3}$ halogenated alkyl, O—$C_{1-3}$ alkyl, hydroxyl, amino, nitro, cyano group, aldehyde group and ester group;
$R^3$ represents $C_{1-6}$ aldehyde group, $C_{2-6}$ acyl group, —COOH, hydroxyl-substituted $C_{1-4}$ alkyl, —$CH_2O$—$C_{1-4}$ alkyl or —$CO_2$—$C_{1-6}$ alkyl;
$R^4$ and $R^7$, at each occurrence, represent hydrogen, $C_{1-20}$ alkyl, $C_{2-36}$ alkenyl, or $C_{2-10}$ alkynyl; or an aryl group or a substituted aryl group by 1-5 groups selected from halogen, $C_{1-3}$ halogenated alkyl, O—$C_{1-3}$ alkyl, $C_{1-25}$ alkyl, hydroxyl, amino, nitro, cyano group, aldehyde group and ester group; and
$R^5$ and $R^6$, at each occurrence, represent hydrogen or $C_{1-4}$ alkyl.

3. The compound of claim 1, wherein:
X represents carbon, sulfur, or oxygen;
$R^1$ represents a $C_{1-3}$ alkyl, allyl, or $C_{3-4}$ alkynyl;
$R^2$ represents hydrogen, halogen, $C_{1-4}$ alkyl, allyl, or $C_{3-7}$ alkynyl; or an aryl group or a substituted aryl group by 1-5 groups selected from halogen, methyl, methoxyl, $C_{2-26}$ alkyl, hydroxyl, nitro, cyano group, aldehyde group and ester group; or a heteroaryl group or a substituted heteroaryl group by 1-5 groups selected from halogen, $C_{1-6}$ alkyl, $C_{1-3}$ halogenated alkyl, O—$C_{1-3}$ alkyl, hydroxyl, nitro, cyano group, aldehyde group and ester group;
the heteroaryl group is a 5-6-membered heteroaryl group comprising N, S, O, or a combination thereof;
$R^3$ represents $C_{1-3}$ aldehyde group, $C_{2-4}$ acyl group, —COOH, hydroxyl-substituted $C_{1-4}$ alkyl, —$CH_2O$—$C_{1-4}$ alkyl or —$CO_2$—$C_{1-4}$ alkyl;
$R^4$ and $R^7$, at each occurrence, represent hydrogen, a $C_{1-17}$ alkyl, $C_{2-36}$ alkenyl, or $C_{2-10}$ alkynyl; or an aryl group or a substituted aryl group by 1-5 groups selected from halogen, methoxyl, $C_{1-25}$ alkyl, hydroxyl, nitro, cyano group, aldehyde group and ester group; and
$R^5$ and $R^6$, at each occurrence, represent hydrogen or methyl.

4. The compound of claim 1, wherein:
X represents carbon, sulfur, or oxygen;
$R^1$ represents a $C_{1-3}$ alkyl, allyl, or $C_{3-4}$ alkynyl;
$R^2$ represents hydrogen, halogen, $C_{1-4}$ alkyl, allyl, or $C_{3-7}$ alkynyl; or an aryl group or a substituted aryl group by 1-5 groups selected from halogen, methyl, methoxyl, $C_{2-26}$ alkyl, hydroxyl, nitro, cyano group, aldehyde group and ester group;
$R^3$ represents $C_{1-3}$ aldehyde group, acetyl group, —COOH, hydroxyl-substituted $C_{1-4}$ alkyl, —$CH_2O$—$C_{1-4}$ alkyl or —$CO_2$—$C_{1-4}$ alkyl;
$R^4$ and $R^7$, at each occurrence, represent hydrogen, $C_{1-17}$ alkyl, $C_{2-36}$ alkenyl, or $C_{2-10}$ alkynyl; or an aryl group or a substituted aryl group by 1-5 groups selected from halogen, methoxyl, $C_{1-25}$ alkyl, hydroxyl, nitro, cyano group, aldehyde group and ester group; and
$R^5$ and $R^6$, at each occurrence, represent hydrogen or methyl.

5. The compound of claim 1, wherein
X represents carbon, sulfur, or oxygen;
$R^1$ represents a $C_{1-3}$ alkyl, allyl, or $C_{3-4}$ alkynyl;
$R^2$ represents hydrogen, halogen, $C_{1-4}$ alkyl, allyl, or $C_{3-7}$ alkynyl; or an aryl group or a substituted aryl group by 1-5 groups selected from halogen, methyl, methoxyl, $C_{2-26}$ alkyl, hydroxyl, nitro, cyano group, aldehyde group and ester group; or a heteroaryl group or a substituted heteroaryl group by 1-5 groups selected from halogen, $C_{1-6}$ alkyl, $C_{1-3}$ halogenated alkyl, O—$C_{1-3}$ alkyl, hydroxyl, nitro, cyano group, aldehyde group and ester group;
the heteroaryl group is a 5-6-membered heteroaryl group comprising N, S, O, or a combination thereof;
$R^3$ represents formyl, acetyl, —COOH, hydroxyl-substituted $C_{1-2}$ alkyl, —$CH_2O$—$C_{1-2}$ alkyl or —$CO_2$—$C_{1-4}$ alkyl;
$R^4$ and $R^7$, at each occurrence, represent hydrogen, $C_{1-17}$ alkyl, $C_{2-36}$ alkenyl, or $C_{2-10}$ alkynyl; or an aryl group or a substituted aryl group by 1-5 groups selected from halogen, methoxyl, $C_{1-25}$ alkyl, hydroxyl, nitro, cyano group, aldehyde group and an ester group; and
$R^5$ and $R^6$, at each occurrence, represent hydrogen or methyl.

6. The compound of claim 1, wherein the compound has one of the following formulas:
I-1
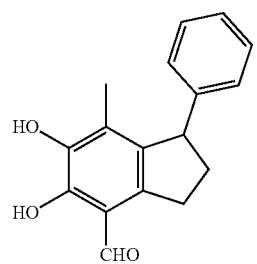
I-2
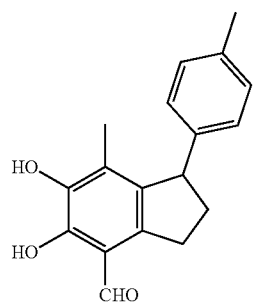
I-3
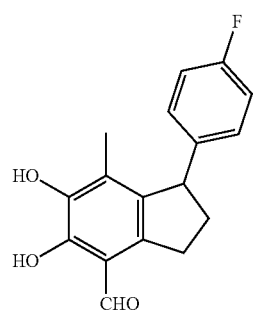
I-4
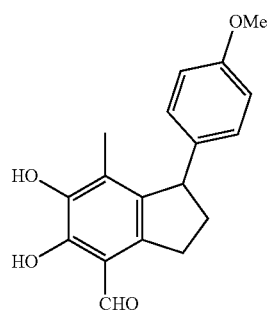
I-5
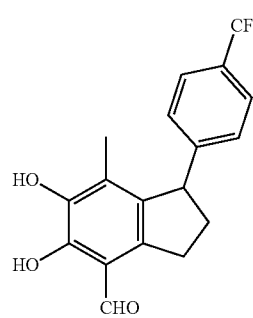
I-6
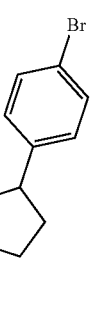
I-7
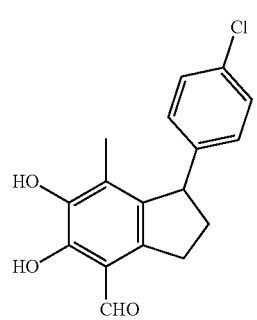
I-8
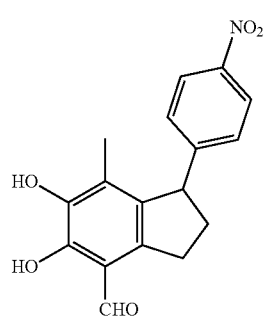
I-9
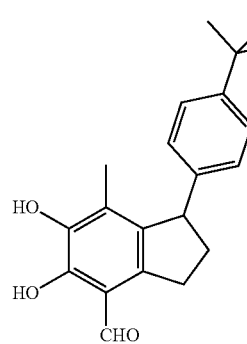
I-10
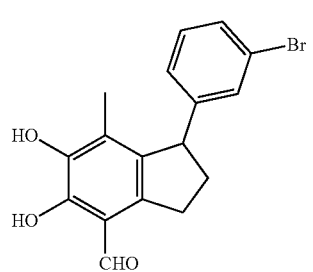

-continued
I-11
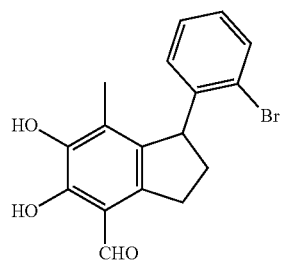
I-12
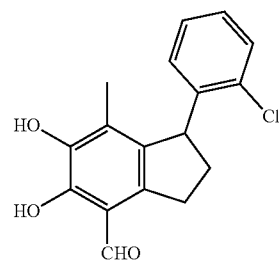
I-13
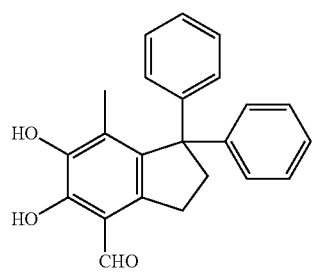
I-14
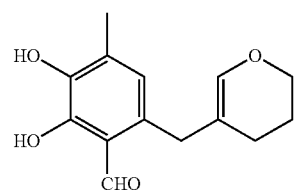
I-15
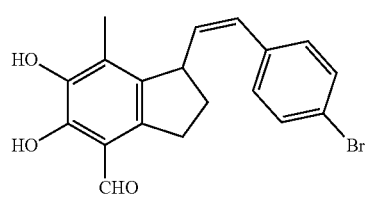
I-16
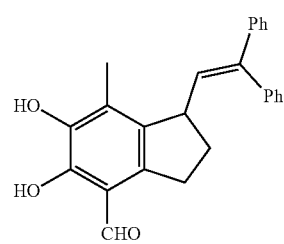
I-17
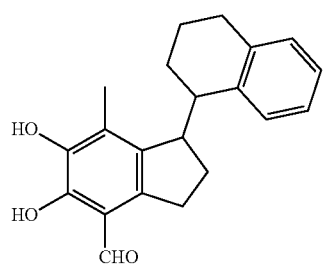
I-18
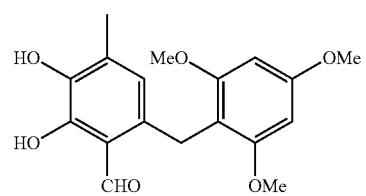
I-19
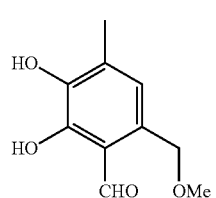
I-20
I-21
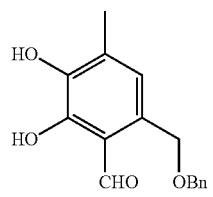
I-22
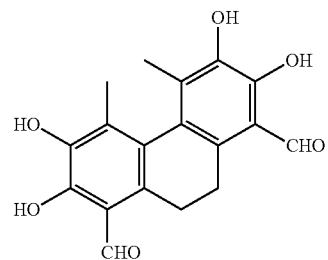

-continued
I-23
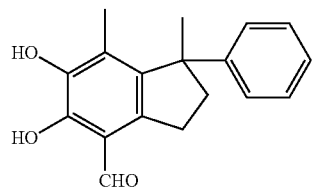
I-24
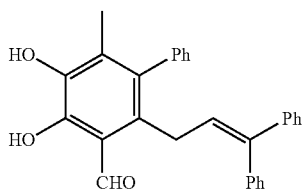
I-25
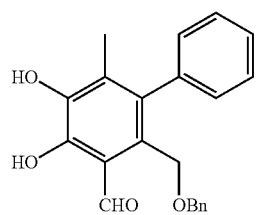
I-26
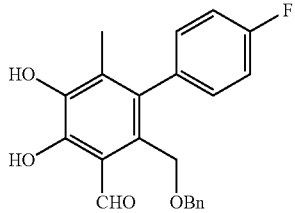
I-27
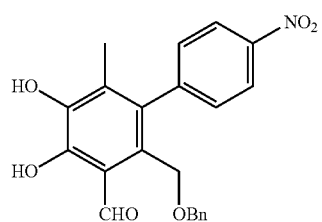
I-28
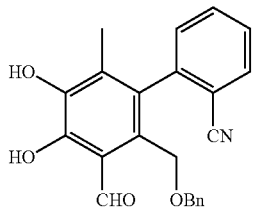
I-29
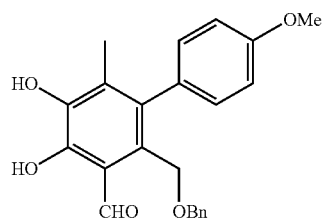
I-30
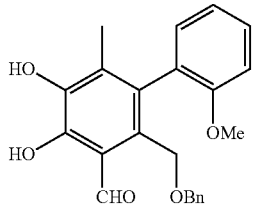
I-31
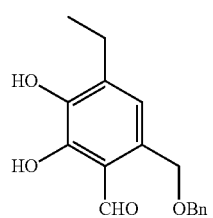
I-32
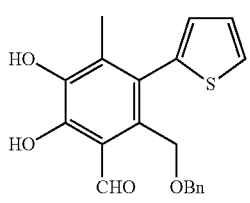
I-33
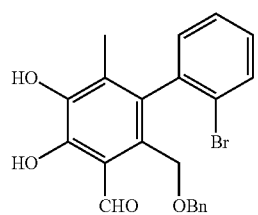
I-34
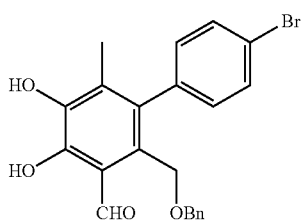
I-35
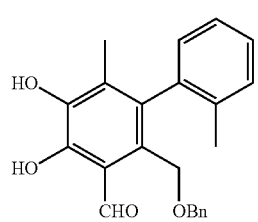
I-36
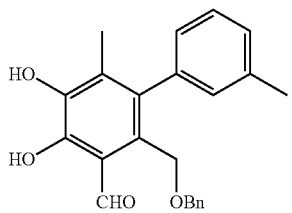

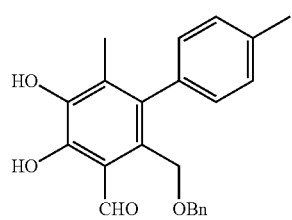
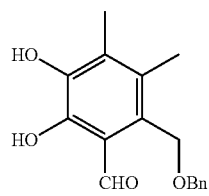
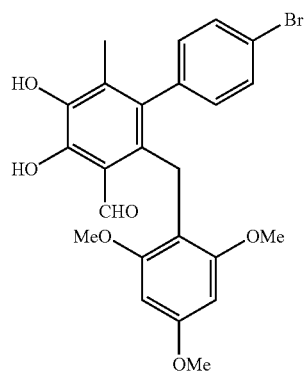
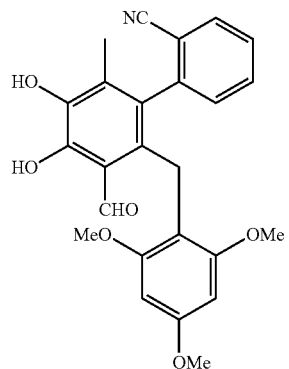
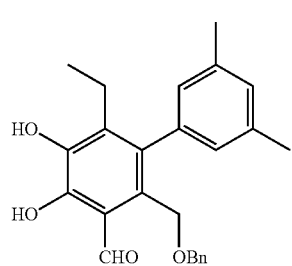
-continued
I-37
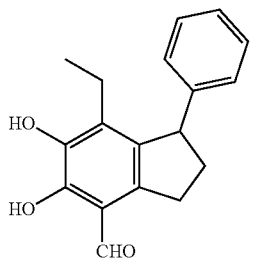
I-38
I-39
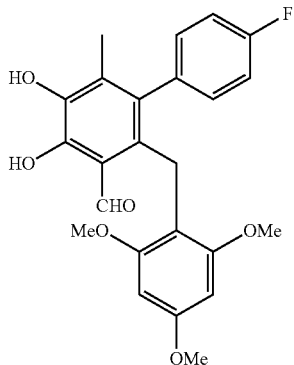
I-40
I-41
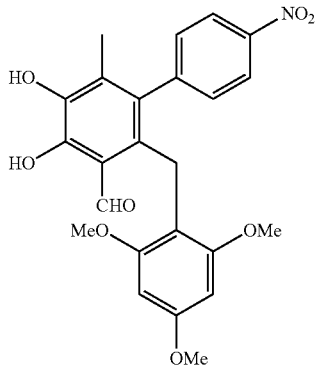
I-42
I-43
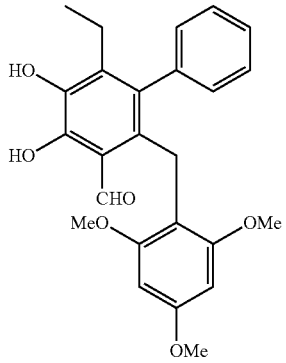
I-44
I-45
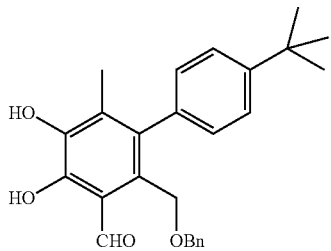
I-46

-continued
I-47
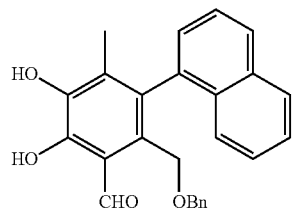
I-48
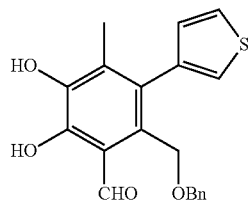
I-49
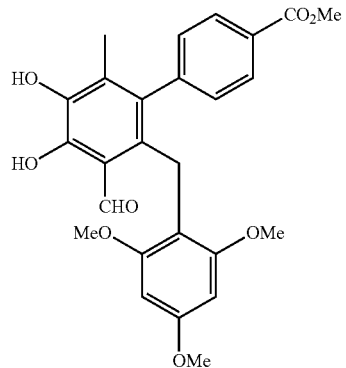
I-50
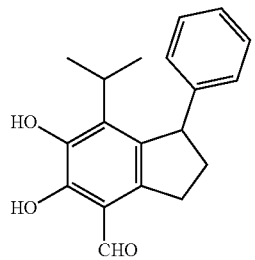
I-51
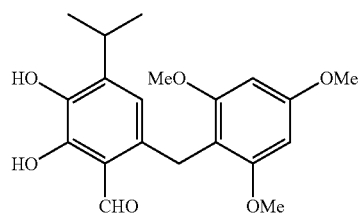
I-52
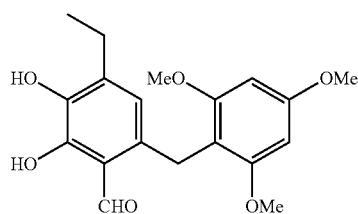
I-53
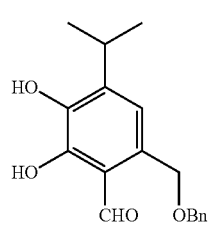
I-54
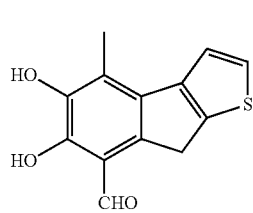
I-55
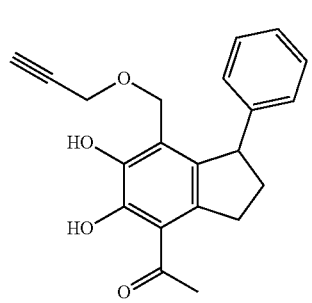
I-A1
I-A2
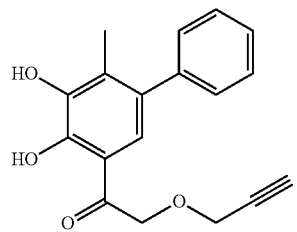
I-A3
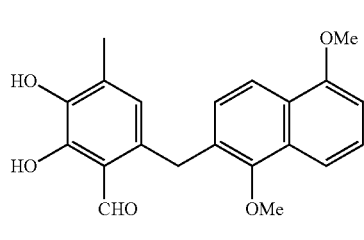

-continued
| | |
|---|---|
| I-A4 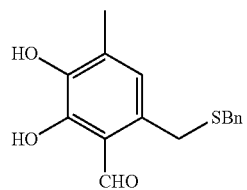 | I-A5 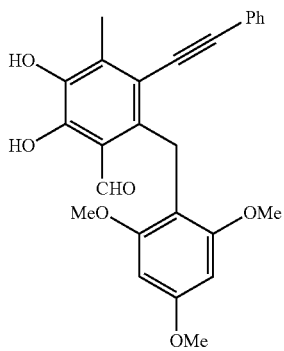 |
| I-A6 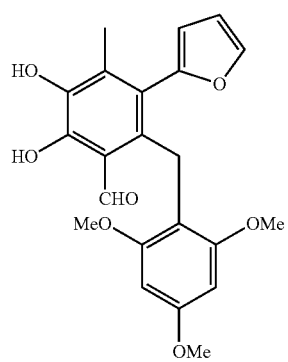 | I-A7 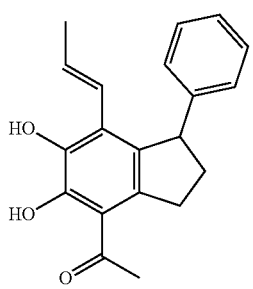 |
| I-A8 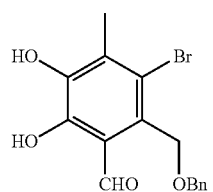 | I-65 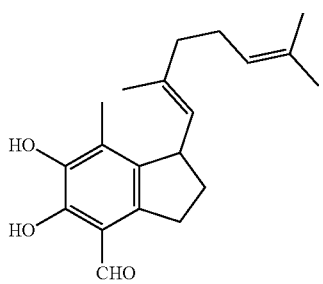 |
| I-66 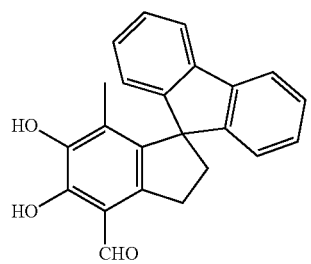 | I-67 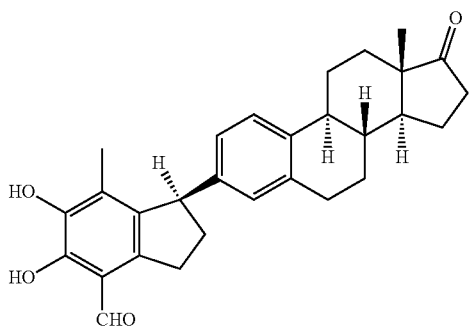 |

-continued
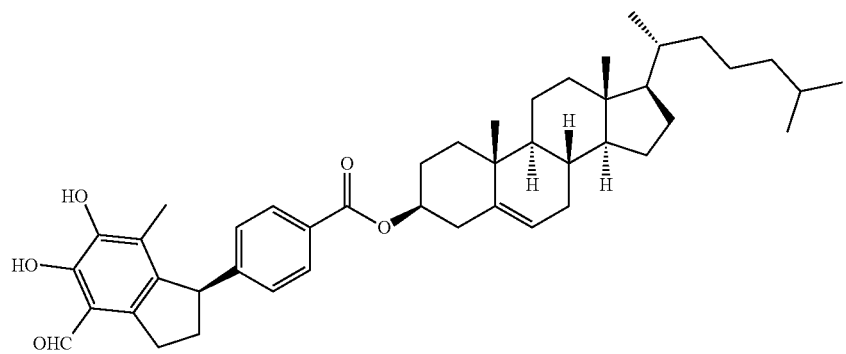
I-68
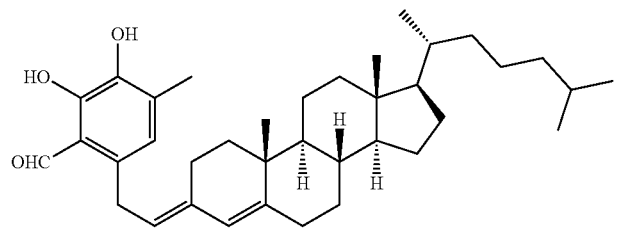
I-69
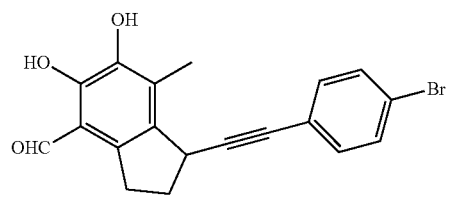
I-70
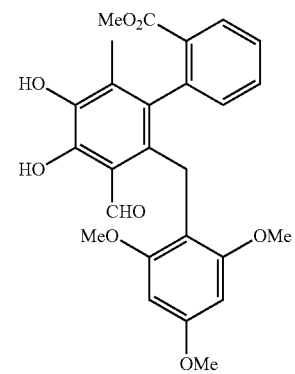 [SMILES: COC(=O)c1ccccc1-c1c(C)c(O)c(O)c(C=O)c1Cc1c(OC)cc(OC)cc1OC]
I-71
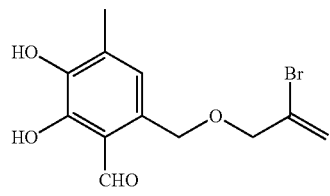 [SMILES: C=C(Br)COCc1cc(C)c(O)c(O)c1C=O]
I-72
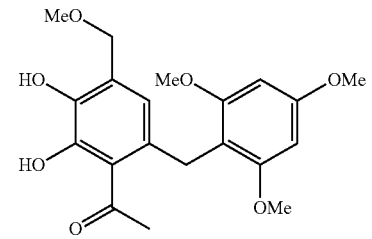 [SMILES: COCc1cc(Cc2c(OC)cc(OC)cc2OC)c(C(C)=O)c(O)c1O]
I-73
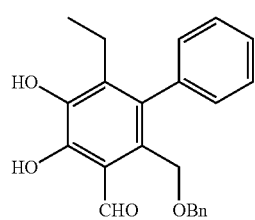 [SMILES: CCc1c(O)c(O)c(C=O)c(COCc2ccccc2)c1-c1ccccc1]
I-74
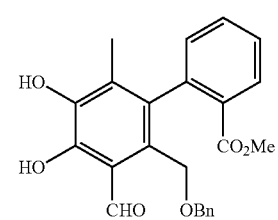 [SMILES: COC(=O)c1ccccc1-c1c(C)c(O)c(O)c(C=O)c1COCc1ccccc1]
I-75
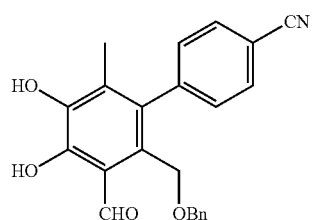
I-76
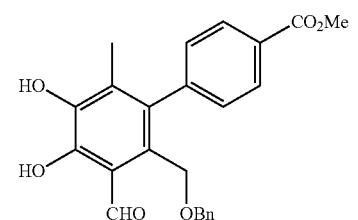 [SMILES: COC(=O)c1ccc(-c2c(C)c(O)c(O)c(C=O)c2COCc2ccccc2)cc1]
I-77

I-78 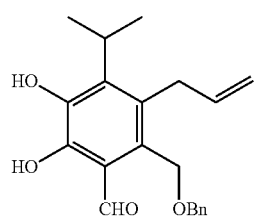 I-79 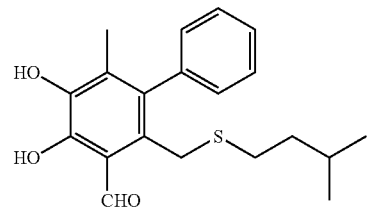
I-80 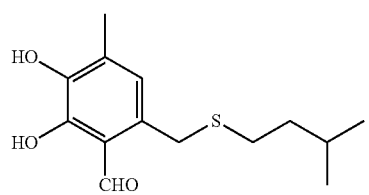 I-81 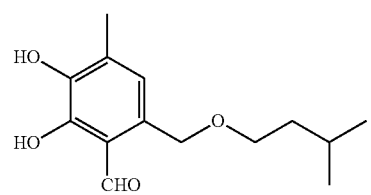 [SMILES: Cc1cc(COCCC(C)C)c(C=O)c(O)c1O]
I-82 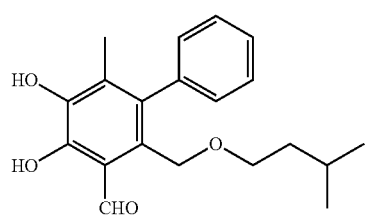 [SMILES: Cc1c(O)c(O)c(C=O)c(COCCC(C)C)c1-c1ccccc1] I-83 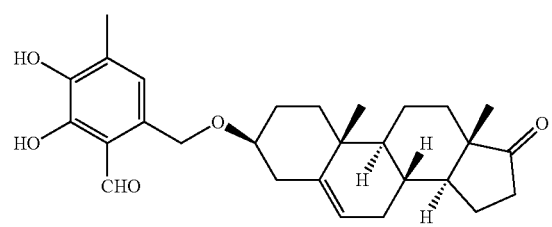
I-84 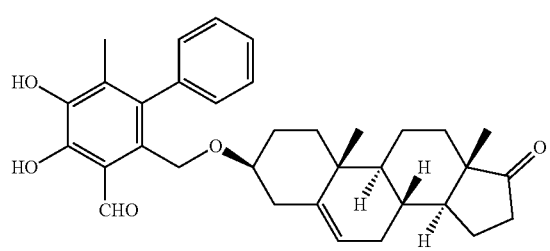 I-85 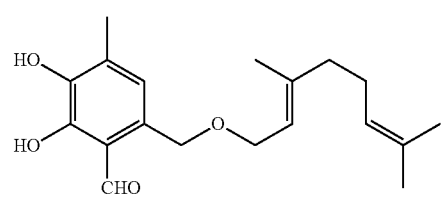 [SMILES: CC(C)=CCC/C(C)=C/COCc1cc(C)c(O)c(O)c1C=O]
I-86 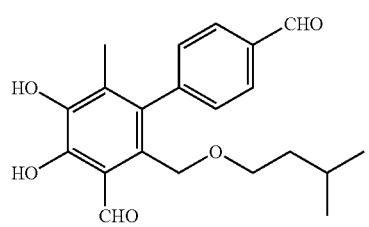 [SMILES: Cc1c(O)c(O)c(C=O)c(COCCC(C)C)c1-c1ccc(C=O)cc1] I-87 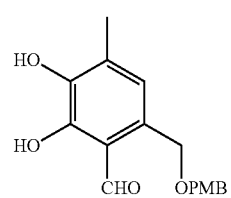
I-88 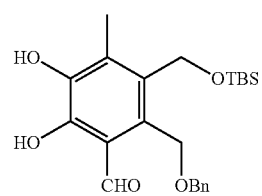
I-89 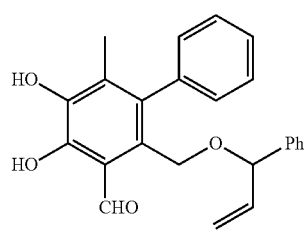 [SMILES: C=CC(OCc1c(C=O)c(O)c(O)c(C)c1-c1ccccc1)c1ccccc1]
I-90 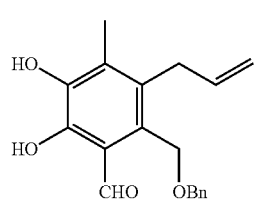 [SMILES: C=CCc1c(C)c(O)c(O)c(C=O)c1COCc1ccccc1] I-91 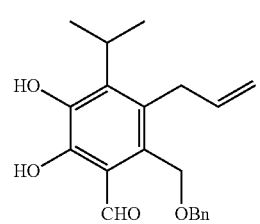 [SMILES: C=CCc1c(COCc2ccccc2)c(C=O)c(O)c(O)c1C(C)C]

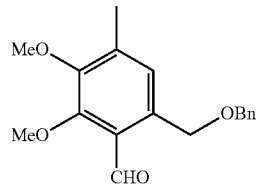 [SMILES: COc1c(C)cc(COCc2ccccc2)c(C=O)c1OC]
I-92
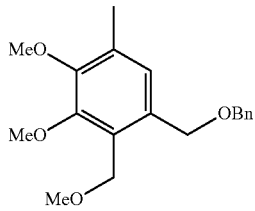 [SMILES: COCc1c(COCc2ccccc2)cc(C)c(OC)c1OC]
I-93
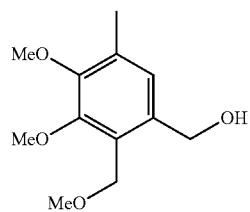
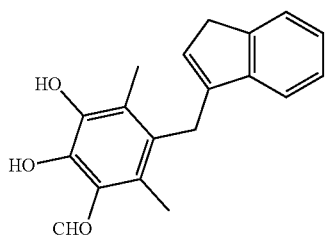
I-94
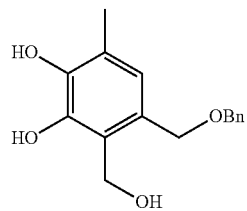 [SMILES: Cc1cc(COCc2ccccc2)c(CO)c(O)c1O]
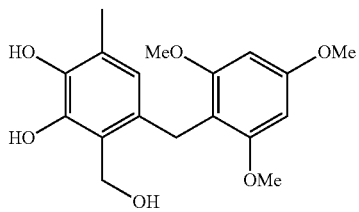 [SMILES: COc1cc(OC)c(Cc2cc(C)c(O)c(O)c2CO)c(OC)c1]
I-95
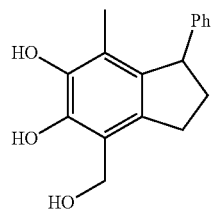
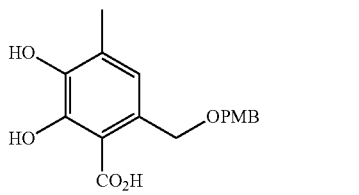
I-96
I-97
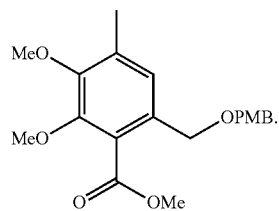
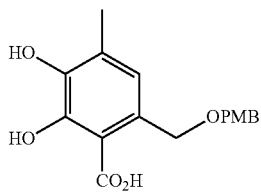
I-98
I-99
I-100
7. A pharmaceutical composition, comprising the compound of claim 1 and a pharmaceutically acceptable excipient.
* * * * *